US010233235B2

(12) United States Patent
Thurman et al.

(10) Patent No.: US 10,233,235 B2
(45) Date of Patent: Mar. 19, 2019

(54) MODULATING THE ALTERNATIVE COMPLEMENT PATHWAY

(71) Applicant: The Regents of the University of Colorado, a body corporate, Denver, CO (US)

(72) Inventors: Joshua M. Thurman, Greenwood Village, CO (US); V. Michael Holers, Denver, CO (US)

(73) Assignee: The Regents of the University of Colorado, A Body Corporate, Denver, CO (US)

( * ) Notice: Subject to any disclaimer, the term of this patent is extended or adjusted under 35 U.S.C. 154(b) by 362 days.

(21) Appl. No.: 14/571,102

(22) Filed: Dec. 15, 2014

(65) Prior Publication Data

US 2015/0147323 A1 May 28, 2015

Related U.S. Application Data

(63) Continuation of application No. 13/120,125, filed as application No. PCT/US2009/057919 on Sep. 22, 2009, now Pat. No. 8,937,046.

(60) Provisional application No. 61/099,173, filed on Sep. 22, 2008.

(51) Int. Cl.

| | |
|---|---|
| ***C07K 16/18*** | (2006.01) |
| ***A61K 38/17*** | (2006.01) |
| ***C07K 14/47*** | (2006.01) |
| ***C12N 9/88*** | (2006.01) |
| *A61K 38/00* | (2006.01) |

(52) U.S. Cl.

CPC ............ *C07K 16/18* (2013.01); *A61K 38/177* (2013.01); *A61K 38/1709* (2013.01); *C07K 14/4721* (2013.01); *C12N 9/88* (2013.01); *A61K 38/00* (2013.01); *C07K 2317/54* (2013.01); *C07K 2317/55* (2013.01); *C07K 2319/70* (2013.01); *C12Y 402/01002* (2013.01)

(58) Field of Classification Search

None

See application file for complete search history.

(56) References Cited

U.S. PATENT DOCUMENTS

| | | | |
|---|---|---|---|
| 4,816,567 | A | 3/1989 | Cabilly et al. |
| 4,943,529 | A | 7/1990 | Van den Berg et al. |
| 5,580,723 | A | 12/1996 | Wells et al. |
| 6,214,966 | B1 | 4/2001 | Harris |
| 6,458,360 | B1 | 10/2002 | Fearon et al. |
| 8,937,046 | B2 | 1/2015 | Thurman et al. |
| 2001/0018051 | A1 | 8/2001 | White et al. |
| 2003/0143223 | A1 | 7/2003 | Cabezas et al. |
| 2006/0105952 | A1 | 5/2006 | Allison |
| 2007/0065433 | A1 | 3/2007 | Mollnes et al. |
| 2007/0154897 | A1 | 7/2007 | Yen et al. |
| 2011/0014270 | A1 | 1/2011 | Holers et al. |
| 2012/0122107 | A1 | 5/2012 | Thiel et al. |
| 2013/0344073 | A1 | 12/2013 | Schwaeble et al. |
| 2017/0209549 | A1 | 7/2017 | Holers et al. |

FOREIGN PATENT DOCUMENTS

| | | | |
|---|---|---|---|
| EP | 0 139 383 | | 5/1985 |
| EP | 0 183 070 | | 6/1986 |
| EP | 0 244 234 | A2 | 11/1987 |
| EP | 0 394 538 | A1 | 10/1990 |
| EP | 0 402 226 | A1 | 12/1990 |
| WO | WO 91/00357 | | 1/1991 |
| WO | WO 91/09967 | | 7/1991 |
| WO | WO 91/09968 | | 7/1991 |
| WO | WO-9802454 | A2 | 1/1998 |
| WO | WO 0129054 | A2 | 4/2001 |
| WO | WO-2005027965 | A1 | 3/2005 |
| WO | WO-2010034015 | A2 | 3/2010 |
| WO | WO-2015187992 | A2 | 12/2015 |

OTHER PUBLICATIONS

Garnett "Targeted drug conjugates: priniciples and progress" Advanced Drug Delivery Reviews 53 (2001) 171-216.*

Suzawa et al. "Synthesis of a novel duocarmycin derivative DU-257 and its application to immunoconjugate using poly(ethylene glycol)-dipeptidyl linker capable of tumor specific activation" Bioorganic & Medicinal Chemistry 8 (2000) 2175-2184.*

Alexander, J.J. et al., "The simple design of complement factor H: Looks can be deceiving," *Molecular Immunology* (2007) 44:123-132.

Atkinson, C. et al. "Targeted complement inhibition by C3d recognition ameliorates tissue injury without apparent increase in susceptibility to infection," *The Journal of Clinical Investigation* (Sep. 2005) 115(9):2444-2453.

Ballance, D.J. et al., "Transformation of *Aspergillus nidulans* by the Orotidine-5'-Phosphate Decarboxylase Gene of *Neurospora crassa,*" *Biochemical and Biophysical Research Communications* (Apr. 15, 1983) 112(1):284-289.

Beach, D. et al., "High-frequency transformation of the fission yeast *Schizosaccharomyces pombe,*" *Nature* (Mar. 12, 1981) 290:140-142.

Carter et al., "Mendelian inheritance of familial prostate cancer," *Proc. Nat'l Acad. Sci. USA*(Apr. 1992) 89: 3367-3371.

Cheng, C-W. et al., "Calcium-binding proteins annexin A2 and S100A6 are sensors of tubular injury and recovery in acute renal failure," *Kidney International* (2005) 68:2694-2703.

Co, M.S. et al., "Chimeric and Humanized antibodies with specificity for the CD33 antigen," *The Journal of Immunology* (Feb. 15, 1992) 148:1149-1154.

(Continued)

*Primary Examiner* — Daniel E Kolker

*Assistant Examiner* — James Rogers

(74) *Attorney, Agent, or Firm* — Wilson Sonsini, Goodrich & Rosati

(57) ABSTRACT

Provided herein are compositions, including pharmaceutical compositions, and methods for modulating, i.e., stimulating or inhibiting, activity of the alternative complement pathway, and methods of identifying factor H-binding proteins.

41 Claims, 11 Drawing Sheets

Specification includes a Sequence Listing.

(56) References Cited

OTHER PUBLICATIONS

Cunningham, B.C. et al., "High-Resolution Epitope Mapping of hGH-Receptor Interactions by Alanine-Scanning Mutagenesis," *Science* (Jun. 2, 1989) 244(4908):1081-1085.

Edwards A.O. et al., " Compliment Factor H Polymorphism and Age-Related Macular Degeneration" *Science* ( Apr. 15, 2005) 308 (5720) 421-424.

Ferreira et al., " Critical Role of C- Terminal Domains of Factor H in Regulating Complement Activation at Cell Surfaces" *The Journal of Immunology* (2006) 177:6308-6316.

Fleer, R. et al., "Stable Multicopy Vectors for High-Level Secretion of Recombinant Human Serum Albumin by *Kluyveromyces* Yeasts," *Nature BioTechnology* (Oct. 1991) 9:968-975.

Friedman et al., "Novel Mechanism of Antibody-Independent Complement Neutralization of Herpes Simplex Virus Type 1," *The Journal of Immunology* (2000) 165:4528-4536.

ATCC Deposit No. ATCC _16045.

ATCC Deposit No. ATCC _24178.

ATCC Deposit No. ATCC _27325.

ATCC Deposit No. ATCC _31449.

ATCC Deposit No. ATCC_12424.

ATCC Deposit No. ATCC _31537.

ATCC Deposit No. ATCC _36906.

ATCC Deposit No. ATCC _56500.

Gerke, V. et al., "Annexins: from structure to function," *Physiol. Rev.* (2002) 82:331-371.

Hageman, G.S. et al., "A common haplotype in the complement regulatory gene factor H (HF1/CFH) predisposes individuals to age-related macular degeneration," *Proc. Nat'l Acad. Sci. USA* (2005) 102(20):7227-7232.

Haines, J.L. et al., "Complement Factor H Variant Increases the Risk of Age-Related Macular Degeneration," *Science* (Apr. 15, 2005) 308:419-421.

Hajjar, K.A. et al., "An endothelial cell receptor for plasminogen/ tissue plasminogen activator," *The Journal of Biological Chemistry* (1994) 269(33):21191-21197.

Havliš, J. et al., "Fast-Response Proteomics by Accelerated In-Gel Digestion of Proteins," *Anal. Chem.* (2003) 75:1300-1306.

Ishi et al., "Recombinant annexin-2 inhibits the progress of diabetic mouse model via recovery of hypercoagulability," *Thromb Haemost* (2007) 97:124-128.

Jimenez, C.R. et al., "In-Gel Digestion of Proteins for MALDI-MS Fingerprint Mapping," *Current Protocols in Protein Science* (1998) Supplement 14, 16.4.1-16.4.5.

Kelly et al., "Transformation of *Apergillus niger* by the amdS gene of *Aspergillus nidulans" The EMBO Journal* (1985) 4 (2) 475-479.

Kirshnek et al., Annexin II is a novel receptor for Pseudomonas aeruginosa, *Biochemical and Physical Research Communications* (2005) 327:900-906.

Klein, R.J. et al., "Complement Factor H Polymorphism in Age-Related Macular Degeneration," *Science* (Apr. 15, 2005) 308:385-389.

Kohler, G. et al., "Continuous cultures of fused cells secreting antibody of predefined specificity," *Nature* (Aug. 7, 1975) 256:495-497.

Kraiczy et al., "Complement escape of human pathogenic baceteria by acquisition of complement regulators," *Molecular Immunology* (2006) 43:31-44.

Lovencourt et al., "Transformation of *Kluyveromyces lactis* by Killer Plasmid DNA" *Journal of Bacteriology* (May 1983) 154 (2): 737-742.

Mandel, M. et al., "Calcium-dependent Bacteriophage DNA Infection," *J. Mol. Biol.* (1970) 53:159-162.

Meri, S. et al., "Discrimination between activators and nonactivators of the alternative pathway of complement: regulation via a sialic acid/polyanioni binding site on factor H," *Proc. Nat'l Acad. Sci. USA* (1990) 87-:3982-3986.

Morrison, S.L. et al., "Chimeric hman antibody molecules: mouse antigen-binding domains with human constant region domains," *Proc. Nat'l Acad. Sci. USA* (Nov. 1984) 81:6851-55.

Ogelsby, T.J. et al., "Membrane cofactor protein (CD46) protects cells from complement-mediated attack by an intrinsic mechanism," *J. Exp. Med.* (Jun. 1992) 175:1547-1551.

Pickering, M.C. et al., "Translational mini-review series on complement factor H: renal diseases associated with complement factor H: novel insights from humans and animals," *Clinical and Experimental Immunology* (2008) 151:210-230.

Pickering, M.C. et al., "Uncontrolled C3 activation causes membranoproliferative glomerulonephritis in mice deficient in complement factor H," *Nature Genetics* (Aug. 2002) 31:424-428.

Raghava, S. et al., "Periocular routes for retinal drug delivery," *Expert Opinion on Drug Delivery* (2004) 1(1):99-114.

Rescher, U. et al., "Annexins-unique membrane binding proteins with diverse functions," *Journal of Cell Science* (2004) 117:2631-2639.

Routledge, E.G. et al., "A humanized monovalent CD3 antibody which can activate homologous complement," *Eur. J. Immunol.* (1991) 21: 2717-2725.

Sanger et al., "DNA Sequencing with chain-terminating inhibitors" *Proc. Nat'l Acad. Sci. USA* (1977) 74 (12): 5463-5467.

Sjoberg, A.P. et al., "The factor H variant associated with age-related macular degernation (His-384) and the non-disease-associated from bind differentially to C-reactive protein, fibromodulin, DNA, and necrotic cells," *The Journal of Biological Chemistry* (Apr. 13, 2007) 282(15):10894-10900.

Smith et al., "New Approaches to the Treatment of Dense Deposit Disease" *Journal of the American Society of Nephrology* (2007) 18: 2447-2456.

Song, H. et al., "Complement receptor 2-mediated targeting of complement inhibitors to sites of complement activation," *The Journal of Clinical Investigation* (Jun. 2003) 111(12):1875-1885.

Sreekrishna, K. et al., "High level expression of heterologous proteins in methylotrophic yeast *Pichia pastoris," J. Basic Microbiol.* (1988) 28(4):265-278.

Studier, F.W. et al., "Use of T7 RNA Polymerase to Direct Expression of Cloned Genes," *Methods in Enzymology* (1990) 185:60-89.

Tilburn, J. et al., "Transformation by integration in *Aspergillus nidulans," Gene* (1983) 26:205-221.

Tran et al., "Cloning, purification and crystallization of full-length human annexin 2," *Acta Cryst.* (2002) D58:1854-1857.

Umeda, S. et al., "Molecular composition of drusen and possible involvement of anti-retinal autoimmunity in two different forms of macular degeneration in cynomolgus monkey monkey (*Macaca fascicularis*)," *The FASEB Journal* (Oct. 2005) 19(12):1683-1685.

UnitProtKB/Swiss-Prot. Accession No. P06909, (Sep. 2, 2008).

UnitProtKB/Swiss-Prot. Accession No. P08173, (Jul. 22, 2008).

UnitProtKB/Swiss-Prot. Accession No. P08603, (Jul. 22, 2008).

UnitProtKB/Swiss-Prot. Accession No. P13987, (Jul. 22, 2008).

UnitProtKB/Swiss-Prot. Accession No. P15529, (Sep. 2, 2008).

UnitProtKB/Swiss-Prot. Accession No. P17927, (Jul. 22, 2008).

Van Den Berg, J.A. et al., "*Kluyveromyces* as a host for heterologous gene expression: expression and secretion of prochymosin," *Nature BioTechnology* (Feb. 1990) 8:135-139.

Whittle, N. et al., "Expression in COS cells of a mouse—human chimaeric B72.3," *Protein Engineering* 1987) 1(6):499-505.

Yelton et al., "Transformation of *Aspergillus nidulans* by using a trpC plasmid" *Proc. Nat'l Acad. Sci. USA* (1984) 81: 1470-1474.

Zhou et al., "Predominant role for C5b-9 in renal ischemia/ reperfusion injury" The Journal of Clinical Investifation (May 2000) 105 (10) :1363-1371.

Zipfel, P.F. "Complement Factor H: Physiology and Pathophysiology," Seminars in Thrombosis and Hemostasis (2001), 27(3):191-199.

International Preliminary Report on Patentability for International Application No. PCT/US2009/057912 dated Mar. 22, 2011, 1 page.

International Search Report for International Application No. PCT/ US2009/057912 dated May 27, 2010, 3 pages.

Written Opinion of the International Searching Authority for International Application No. PCT/US2009/057912 dated May 27, 2010, 5 pages.

(56) References Cited

OTHER PUBLICATIONS

Alexander, et al. Administration of the soluble complement inhibitor, Crry-Ig, reduces inflammation and aquaporin 4 expression in lupus cerebritis. Biochim Biophys Acta. Nov. 20, 2003;1639(3):169-76.
Aslam, et al. The extended multidomain solution structures of the complement protein Crry and its chimeric conjugate Crry-Ig by scattering, analytical ultracentrifugation and constrained modelling: implications for function and therapy. J Mol Biol. Jun. 6, 2003;329(3):525-50.
Banda, et al. Essential role for the lectin pathway in collagen antibody-induced arthritis revealed through use of adenovirus programming complement inhibitor MAp44 expression. J Immunol. Sep. 1, 2014;193(5):2455-68.
Chan, et al. Attenuation of skeletal muscle reperfusion injury with intravenous 12 amino acid peptides that bind to pathogenic IgM. Surgery. Feb. 2006;139(2):236-43.
Co-pending U.S. Appl. No. 16/015,019, filed Jun. 21, 2018.
Co-pending U.S. Appl. No. 16/015,071, filed Jun. 21, 2018.
Degn, et al. Co-complexes of MASP-1 and MASP-2 associated with the soluble pattern-recognition molecules drive lectin pathway activation in a manner inhibitable by MAp44. J Immunol. Aug. 1, 2013;191(3):1334-45.
Degn, et al. MAp44, a human protein associated with pattern recognition molecules of the complement system and regulating the lectin pathway of complement activation. J Immunol. Dec. 1, 2009;183(11):7371-8.
European search report and search opinion dated Dec. 14, 2017 for EP Patent Application No. 15802708.6.
Fodor, et al. A novel bifunctional chimeric complement inhibitor that regulates C3 convertase and formation of the membrane attack complex.J Immunol. Nov. 1, 1995;155(9):4135-8.
Haas, et al. Blockade of self-reactive IgM significantly reduces injury in a murine model of acute myocardial infarction. Cardiovasc Res. Sep. 1, 2010; 87(4): 618-627.
International search report and written opinion dated Dec. 17, 2015 for PCT Application No. PCT/US15/34270.
Kim, et al. I-PLA(2) activation during apoptosis promotes the exposure of membrane lysophosphatidylcholine leading to binding by natural immunoglobulin M antibodies and complement activation. J Exp Med. Sep. 2, 2002;196(5):655-65.
Linton, et al. Therapeutic efficacy of a novel membrane-targeted complement regulator in antigen-induced arthritis in the rat. Arthritis Rheum. Nov. 2000;43(11):2590-7.
Notice of Allowance dated Sep. 16, 2014 for U.S. Appl. No. 13/120,125.
Office action dated May 9, 2014 for U.S. Appl. No. 13/120,125.
Office action dated Dec. 19, 2013 for U.S. Appl. No. 13/120,125.
Quigg, et al. Blockade of antibody-induced glomerulonephritis with Crry-Ig, a soluble murine complement inhibitor. J Immunol. May 1, 1998;160(9):4553-60.
Rittershaus, et al. Recombinant glycoproteins that inhibit complement activation and also bind the selectin adhesion molecules. J Biol Chem. Apr. 16, 1999;274(16):11237-44.
Schmid, et al. TP20 is superior to TP10 in reducing ischemia/reperfusion injury in rat lung grafts. Transplant Proc. Feb.-Mar. 2001;33(1-2):948-9.
Sihag, et al. Natural IgM Blockade Limits Infarct Expansion and Left Ventricular Dysfunction in a Swine Myocardial Infarct Model. Circ Cardiovasc Interv. Jan. 2016; 9(1): e002547.
Smith, et al. Cell surface engineering using a complement regulatory molecule modified with a synthetic myristoyl-electrostatic switch derivative. Molecular Immunology. 1998; 35, 400.
Smith, et al. Membrane-targeted complement inhibitors. Mol Immunol. Aug. 2001;38(2-3):249-55.
Smith, et al. Targeting anticomplement agents. Biochem Soc Trans. Nov. 2002;30(Pt 6):1037-41.
Spitzer, et al. In vivo correction of complement regulatory protein deficiency with an inhibitor targeting the red blood cell membrane. J Immunol. Dec. 1, 2005;175(11):7763-70.
Spitzer, et al. ScFv-mediated in vivo targeting of DAF to erythrocytes inhibits lysis by complement. Mol Immunol. Feb. 2004;40(13):911-9.
Taube, et al. Inhibition of complement activation decreases airway inflammation and hyperresponsiveness. Am J Respir Crit Care Med. Dec. 1, 2003;168(11):1333-41.
Tuominen, et al. A natural antibody to oxidized cardiolipin binds to oxidized low-density lipoprotein, apoptotic cells, and atherosclerotic lesions. Arterioscler Thromb Vasc Biol. Sep. 2006;26(9):2096-102.
Wang, et al. Amelioration of lupus-like autoimmune disease in NZB/WF1 mice after treatment with a blocking monoclonal antibody specific for complement component C5. Proc Natl Acad Sci U S A. Aug. 6, 1996; 93(16): 8563-8568.
Wang, et al. Anti-C5 monoclonal antibody therapy prevents collagen-induced arthritis and ameliorates established disease. Proc Natl Acad Sci U S A. Sep. 12, 1995; 92(19): 8955-8959.
Wang, et al. Characterization of a natural mouse monoclonal antibody recognizing epitopes shared by oxidized low-density lipoprotein and chaperonin 60 of Aggregatibacter actinomycetemcomitans. Immunol Res. Jun. 2016;64(3):699-710.
Wang, et al. Complement inhibition with an anti-C5 monoclonal antibody prevents hyperacute rejection in a xenograft heart transplantation model. Transplantation. Dec. 15, 1999;68(11):1643-51.
Wang, et al. Natural Monoclonal Antibody to Oxidized Low-Density Lipoprotein and Aggregatibacter actinomycetemcomitans. Methods Mol Biol. 2017;1643:155-167.
Zhang, et al. Identification of a specific self-reactive IgM antibody that initiates intestinal ischemia/reperfusion injury. Proc Natl Acad Sci U S A. Mar. 16, 2004; 101(11): 3886-3891.
Zhang, et al. Targeting of functional antibody-CD59 fusion proteins to a cell surface. J Clin Invest. Jan. 1, 1999; 103(1): 55-61.

* cited by examiner

SEQUENCE LISTING

<160> NUMBER OF SEQ ID NOS: 31

<210> SEQ ID NO 1
<211> LENGTH: 339
<212> TYPE: PRT
<213> ORGANISM: Homo sapiens

<400> SEQUENCE: 1

```
Met Ser Thr Val His Glu Ile Leu Cys Lys Leu Ser Leu Glu Gly Asp
1               5                   10                  15

His Ser Thr Pro Pro Ser Ala Tyr Gly Ser Val Lys Ala Tyr Thr Asn
            20                  25                  30

Phe Asp Ala Glu Arg Asp Ala Leu Asn Ile Glu Thr Ala Ile Lys Thr
        35                  40                  45

Lys Gly Val Asp Glu Val Thr Ile Val Asn Ile Leu Thr Asn Arg Ser
    50                  55                  60

Asn Ala Gln Arg Gln Asp Ile Ala Phe Ala Tyr Gln Arg Arg Thr Lys
65                  70                  75                  80

Lys Glu Leu Ala Ser Ala Leu Lys Ser Ala Leu Ser Gly His Leu Glu
                85                  90                  95

Thr Val Ile Leu Gly Leu Leu Lys Thr Pro Ala Gln Tyr Asp Ala Ser
            100                 105                 110

Glu Leu Lys Ala Ser Met Lys Gly Leu Gly Thr Asp Glu Asp Ser Leu
        115                 120                 125

Ile Glu Ile Ile Cys Ser Arg Thr Asn Gln Glu Leu Gln Glu Ile Asn
    130                 135                 140

Arg Val Tyr Lys Glu Met Tyr Lys Thr Asp Leu Glu Lys Asp Ile Ile
145                 150                 155                 160

Ser Asp Thr Ser Gly Asp Phe Arg Lys Leu Met Val Ala Leu Ala Lys
                165                 170                 175

Gly Arg Arg Ala Glu Asp Gly Ser Val Ile Asp Tyr Glu Leu Ile Asp
            180                 185                 190

Gln Asp Ala Arg Asp Leu Tyr Asp Ala Gly Val Lys Arg Lys Gly Thr
        195                 200                 205

Asp Val Pro Lys Trp Ile Ser Ile Met Thr Glu Arg Ser Val Pro His
    210                 215                 220
```

```
Leu Gln Lys Val Phe Asp Arg Tyr Lys Ser Tyr Ser Pro Tyr Asp Met
225                 230                 235                 240

Leu Glu Ser Ile Arg Lys Glu Val Lys Gly Asp Leu Glu Asn Ala Phe
                245                 250                 255

Leu Asn Leu Val Gln Cys Ile Gln Asn Lys Pro Leu Tyr Phe Ala Asp
            260                 265                 270

Arg Leu Tyr Asp Ser Met Lys Gly Lys Gly Thr Arg Asp Lys Val Leu
        275                 280                 285

Ile Arg Ile Met Val Ser Arg Ser Glu Val Asp Met Leu Lys Ile Arg
    290                 295                 300

Ser Glu Phe Lys Arg Lys Tyr Gly Lys Ser Leu Tyr Tyr Tyr Ile Gln
305                 310                 315                 320

Gln Asp Thr Lys Gly Asp Tyr Gln Lys Ala Leu Leu Tyr Leu Cys Gly
                325                 330                 335

Gly Asp Asp


<210> SEQ ID NO 2
<211> LENGTH: 1020
<212> TYPE: DNA
<213> ORGANISM: Homo sapiens

<400> SEQUENCE: 2

atgtctactg ttcacgaaat cctgtgcaag ctcagcttgg agggtgatca ctctacaccc     60

ccaagtgcat atgggtctgt caaagcctat actaactttg atgctgagcg ggatgctttg    120

aacattgaaa cagccatcaa gaccaaaggt gtggatgagg tcaccattgt caacattttg    180

accaaccgca gcaatgcaca gagacaggat attgccttcg cctaccagag aaggaccaaa    240

aaggaacttg catcagcact gaagtcagcc ttatctggcc acctggagac ggtgattttg    300

ggcctattga agacacctgc tcagtatgac gcttctgagc taaaagcttc catgaagggg    360

ctgggaaccg acgaggactc tctcattgag atcatctgct ccagaaccaa ccaggagctg    420

caggaaatta acagagtcta caaggaaatg tacaagactg atctggagaa ggacattatt    480

tcggacacat ctggtgactt ccgcaagctg atggttgccc tggcaaaggg tagaagagca    540

gaggatggct ctgtcattga ttatgaactg attgaccaag atgctcggga tctctatgac    600

gctggagtga agaggaaagg aactgatgtt cccaagtgga tcagcatcat gaccgagcgg    660

agcgtgcccc acctccagaa agtatttgat aggtacaaga gttacagccc ttatgacatg    720

ttggaaagca tcaggaaaga ggttaaagga gacctggaaa atgctttcct gaacctggtt    780

cagtgcattc agaacaagcc cctgtatttt gctgatcggc tgtatgactc catgaagggc    840

aaggggacgc gagataaggt cctgatcaga atcatggtct cccgcagtga agtggacatg    900

ttgaaaatta ggtctgaatt caagagaaag tacggcaagt ccctgtacta ttatatccag    960

caagacacta agggcgacta ccagaaagcg ctgctgtacc tgtgtggtgg agatgactga   1020


<210> SEQ ID NO 3
<211> LENGTH: 1231
<212> TYPE: PRT
<213> ORGANISM: Homo sapiens

<400> SEQUENCE: 3

Met Arg Leu Leu Ala Lys Ile Ile Cys Leu Met Leu Trp Ala Ile Cys
1               5                   10                  15

Val Ala Glu Asp Cys Asn Glu Leu Pro Pro Arg Arg Asn Thr Glu Ile
            20                  25                  30
```

-continued

```
Leu Thr Gly Ser Trp Ser Asp Gln Thr Tyr Pro Glu Gly Thr Gln Ala
        35                  40                  45

Ile Tyr Lys Cys Arg Pro Gly Tyr Arg Ser Leu Gly Asn Val Ile Met
    50                  55                  60

Val Cys Arg Lys Gly Glu Trp Val Ala Leu Asn Pro Leu Arg Lys Cys
65                  70                  75                  80

Gln Lys Arg Pro Cys Gly His Pro Gly Asp Thr Pro Phe Gly Thr Phe
                85                  90                  95

Thr Leu Thr Gly Gly Asn Val Phe Glu Tyr Gly Val Lys Ala Val Tyr
            100                 105                 110

Thr Cys Asn Glu Gly Tyr Gln Leu Leu Gly Glu Ile Asn Tyr Arg Glu
        115                 120                 125

Cys Asp Thr Asp Gly Trp Thr Asn Asp Ile Pro Ile Cys Glu Val Val
    130                 135                 140

Lys Cys Leu Pro Val Thr Ala Pro Glu Asn Gly Lys Ile Val Ser Ser
145                 150                 155                 160

Ala Met Glu Pro Asp Arg Glu Tyr His Phe Gly Gln Ala Val Arg Phe
                165                 170                 175

Val Cys Asn Ser Gly Tyr Lys Ile Glu Gly Asp Glu Glu Met His Cys
            180                 185                 190

Ser Asp Asp Gly Phe Trp Ser Lys Glu Lys Pro Lys Cys Val Glu Ile
        195                 200                 205

Ser Cys Lys Ser Pro Asp Val Ile Asn Gly Ser Pro Ile Ser Gln Lys
    210                 215                 220

Ile Ile Tyr Lys Glu Asn Glu Arg Phe Gln Tyr Lys Cys Asn Met Gly
225                 230                 235                 240

Tyr Glu Tyr Ser Glu Arg Gly Asp Ala Val Cys Thr Glu Ser Gly Trp
                245                 250                 255

Arg Pro Leu Pro Ser Cys Glu Glu Lys Ser Cys Asp Asn Pro Tyr Ile
            260                 265                 270

Pro Asn Gly Asp Tyr Ser Pro Leu Arg Ile Lys His Arg Thr Gly Asp
        275                 280                 285

Glu Ile Thr Tyr Gln Cys Arg Asn Gly Phe Tyr Pro Ala Thr Arg Gly
    290                 295                 300

Asn Thr Ala Lys Cys Thr Ser Thr Gly Trp Ile Pro Ala Pro Arg Cys
305                 310                 315                 320

Thr Leu Lys Pro Cys Asp Tyr Pro Asp Ile Lys His Gly Gly Leu Tyr
                325                 330                 335

His Glu Asn Met Arg Arg Pro Tyr Phe Pro Val Ala Val Gly Lys Tyr
            340                 345                 350

Tyr Ser Tyr Tyr Cys Asp Glu His Phe Glu Thr Pro Ser Gly Ser Tyr
        355                 360                 365

Trp Asp His Ile His Cys Thr Gln Asp Gly Trp Ser Pro Ala Val Pro
    370                 375                 380

Cys Leu Arg Lys Cys Tyr Phe Pro Tyr Leu Glu Asn Gly Tyr Asn Gln
385                 390                 395                 400

Asn Tyr Gly Arg Lys Phe Val Gln Gly Lys Ser Ile Asp Val Ala Cys
                405                 410                 415

His Pro Gly Tyr Ala Leu Pro Lys Ala Gln Thr Thr Val Thr Cys Met
            420                 425                 430

Glu Asn Gly Trp Ser Pro Thr Pro Arg Cys Ile Arg Val Lys Thr Cys
        435                 440                 445
```

-continued

```
Ser Lys Ser Ser Ile Asp Ile Glu Asn Gly Phe Ile Ser Glu Ser Gln
    450                 455                 460

Tyr Thr Tyr Ala Leu Lys Glu Lys Ala Lys Tyr Gln Cys Lys Leu Gly
465                 470                 475                 480

Tyr Val Thr Ala Asp Gly Glu Thr Ser Gly Ser Ile Thr Cys Gly Lys
                485                 490                 495

Asp Gly Trp Ser Ala Gln Pro Thr Cys Ile Lys Ser Cys Asp Ile Pro
            500                 505                 510

Val Phe Met Asn Ala Arg Thr Lys Asn Asp Phe Thr Trp Phe Lys Leu
        515                 520                 525

Asn Asp Thr Leu Asp Tyr Glu Cys His Asp Gly Tyr Glu Ser Asn Thr
    530                 535                 540

Gly Ser Thr Thr Gly Ser Ile Val Cys Gly Tyr Asn Gly Trp Ser Asp
545                 550                 555                 560

Leu Pro Ile Cys Tyr Glu Arg Glu Cys Glu Leu Pro Lys Ile Asp Val
                565                 570                 575

His Leu Val Pro Asp Arg Lys Lys Asp Gln Tyr Lys Val Gly Glu Val
            580                 585                 590

Leu Lys Phe Ser Cys Lys Pro Gly Phe Thr Ile Val Gly Pro Asn Ser
        595                 600                 605

Val Gln Cys Tyr His Phe Gly Leu Ser Pro Asp Leu Pro Ile Cys Lys
    610                 615                 620

Glu Gln Val Gln Ser Cys Gly Pro Pro Pro Glu Leu Leu Asn Gly Asn
625                 630                 635                 640

Val Lys Glu Lys Thr Lys Glu Glu Tyr Gly His Ser Glu Val Val Glu
                645                 650                 655

Tyr Tyr Cys Asn Pro Arg Phe Leu Met Lys Gly Pro Asn Lys Ile Gln
            660                 665                 670

Cys Val Asp Gly Glu Trp Thr Thr Leu Pro Val Cys Ile Val Glu Glu
        675                 680                 685

Ser Thr Cys Gly Asp Ile Pro Glu Leu Glu His Gly Trp Ala Gln Leu
    690                 695                 700

Ser Ser Pro Pro Tyr Tyr Tyr Gly Asp Ser Val Glu Phe Asn Cys Ser
705                 710                 715                 720

Glu Ser Phe Thr Met Ile Gly His Arg Ser Ile Thr Cys Ile His Gly
                725                 730                 735

Val Trp Thr Gln Leu Pro Gln Cys Val Ala Ile Asp Lys Leu Lys Lys
            740                 745                 750

Cys Lys Ser Ser Asn Leu Ile Ile Leu Glu Glu His Leu Lys Asn Lys
        755                 760                 765

Lys Glu Phe Asp His Asn Ser Asn Ile Arg Tyr Arg Cys Arg Gly Lys
    770                 775                 780

Glu Gly Trp Ile His Thr Val Cys Ile Asn Gly Arg Trp Asp Pro Glu
785                 790                 795                 800

Val Asn Cys Ser Met Ala Gln Ile Gln Leu Cys Pro Pro Pro Pro Gln
                805                 810                 815

Ile Pro Asn Ser His Asn Met Thr Thr Thr Leu Asn Tyr Arg Asp Gly
            820                 825                 830

Glu Lys Val Ser Val Leu Cys Gln Glu Asn Tyr Leu Ile Gln Glu Gly
        835                 840                 845

Glu Glu Ile Thr Cys Lys Asp Gly Arg Trp Gln Ser Ile Pro Leu Cys
    850                 855                 860

Val Glu Lys Ile Pro Cys Ser Gln Pro Pro Gln Ile Glu His Gly Thr
```

-continued

```
865                 870                 875                 880

Ile Asn Ser Ser Arg Ser Ser Gln Glu Ser Tyr Ala His Gly Thr Lys
                885                 890                 895

Leu Ser Tyr Thr Cys Glu Gly Gly Phe Arg Ile Ser Glu Glu Asn Glu
            900                 905                 910

Thr Thr Cys Tyr Met Gly Lys Trp Ser Ser Pro Pro Gln Cys Glu Gly
        915                 920                 925

Leu Pro Cys Lys Ser Pro Pro Glu Ile Ser His Gly Val Val Ala His
    930                 935                 940

Met Ser Asp Ser Tyr Gln Tyr Gly Glu Glu Val Thr Tyr Lys Cys Phe
945                 950                 955                 960

Glu Gly Phe Gly Ile Asp Gly Pro Ala Ile Ala Lys Cys Leu Gly Glu
                965                 970                 975

Lys Trp Ser His Pro Pro Ser Cys Ile Lys Thr Asp Cys Leu Ser Leu
            980                 985                 990

Pro Ser Phe Glu Asn Ala Ile Pro  Met Gly Glu Lys Lys  Asp Val Tyr
        995                 1000                1005

Lys Ala  Gly Glu Gln Val Thr  Tyr Thr Cys Ala Thr  Tyr Tyr Lys
    1010                1015                1020

Met Asp  Gly Ala Ser Asn Val  Thr Cys Ile Asn Ser  Arg Trp Thr
    1025                1030                1035

Gly Arg  Pro Thr Cys Arg Asp  Thr Ser Cys Val Asn  Pro Pro Thr
    1040                1045                1050

Val Gln  Asn Ala Tyr Ile Val  Ser Arg Gln Met Ser  Lys Tyr Pro
    1055                1060                1065

Ser Gly  Glu Arg Val Arg Tyr  Gln Cys Arg Ser Pro  Tyr Glu Met
    1070                1075                1080

Phe Gly  Asp Glu Glu Val Met  Cys Leu Asn Gly Asn  Trp Thr Glu
    1085                1090                1095

Pro Pro  Gln Cys Lys Asp Ser  Thr Gly Lys Cys Gly  Pro Pro Pro
    1100                1105                1110

Pro Ile  Asp Asn Gly Asp Ile  Thr Ser Phe Pro Leu  Ser Val Tyr
    1115                1120                1125

Ala Pro  Ala Ser Ser Val Glu  Tyr Gln Cys Gln Asn  Leu Tyr Gln
    1130                1135                1140

Leu Glu  Gly Asn Lys Arg Ile  Thr Cys Arg Asn Gly  Gln Trp Ser
    1145                1150                1155

Glu Pro  Pro Lys Cys Leu His  Pro Cys Val Ile Ser  Arg Glu Ile
    1160                1165                1170

Met Glu  Asn Tyr Asn Ile Ala  Leu Arg Trp Thr Ala  Lys Gln Lys
    1175                1180                1185

Leu Tyr  Ser Arg Thr Gly Glu  Ser Val Glu Phe Val  Cys Lys Arg
    1190                1195                1200

Gly Tyr  Arg Leu Ser Ser Arg  Ser His Thr Leu Arg  Thr Thr Cys
    1205                1210                1215

Trp Asp  Gly Lys Leu Glu Tyr  Pro Thr Cys Ala Lys  Arg
    1220                1225                1230


<210> SEQ ID NO 4
<211> LENGTH: 3696
<212> TYPE: DNA
<213> ORGANISM: Homo sapiens

<400> SEQUENCE: 4
```

-continued

```
atgagacttc tagcaaagat tatttgcctt atgttatggg ctatttgtgt agcagaagat      60
tgcaatgaac ttcctccaag aagaaataca gaaattctga caggttcctg gtctgaccaa     120
acatatccag aaggcaccca ggctatctat aaatgccgcc ctggatatag atctcttgga     180
aatgtaataa tggtatgcag gaagggagaa tgggttgctc ttaatccatt aaggaaatgt     240
cagaaaaggc cctgtggaca tcctggagat actccttttg gtacttttac ccttacagga     300
ggaaatgtgt ttgaatatgg tgtaaaagct gtgtatacat gtaatgaggg gtatcaattg     360
ctaggtgaga ttaattaccg tgaatgtgac acagatggat ggaccaatga tattcctata     420
tgtgaagttg tgaagtgttt accagtgaca gcaccagaga atggaaaaat tgtcagtagt     480
gcaatggaac cagatcggga ataccatttt ggacaagcag tacggtttgt atgtaactca     540
ggctacaaga ttgaaggaga tgaagaaatg cattgttcag acgatggttt ttggagtaaa     600
gagaaaccaa agtgtgtgga aatttcatgc aaatccccag atgttataaa tggatctcct     660
atatctcaga agattattta taaggagaat gaacgatttc aatataaatg taacatgggt     720
tatgaataca gtgaaagagg agatgctgta tgcactgaat ctggatggcg tccgttgcct     780
tcatgtgaag aaaaatcatg tgataatcct tatattccaa atggtgacta ctcaccttta     840
aggattaaac acagaactgg agatgaaatc acgtaccagt gtagaaatgg tttttatcct     900
gcaacccggg gaaatacagc caaatgcaca agtactggct ggatacctgc tccgagatgt     960
accttgaaac cttgtgatta tccagacatt aaacatggag gtctatatca tgagaatatg    1020
cgtagaccat actttccagt agctgtagga aaatattact cctattactg tgatgaacat    1080
tttgagactc cgtcaggaag ttactgggat cacattcatt gcacacaaga tggatggtcg    1140
ccagcagtac catgcctcag aaaatgttat tttccttatt tggaaaatgg atataatcaa    1200
aatcatggaa gaaagtttgt acagggtaaa tctatagacg ttgcctgcca tcctggctac    1260
gctcttccaa aagcgcagac cacagttaca tgtatggaga atggctggtc tcctactccc    1320
agatgcatcc gtgtcaaaac atgttccaaa tcaagtatag atattgagaa tgggtttatt    1380
tctgaatctc agtatacata tgccttaaaa gaaaaagcga aatatcaatg caaactagga    1440
tatgtaacag cagatggtga aacatcagga tcaattagat gtgggaaaga tggatggtca    1500
gctcaaccca cgtgcattaa atcttgtgat atcccagtat ttatgaatgc cagaactaaa    1560
aatgacttca catggtttaa gctgaatgac acattggact atgaatgcca tgatggttat    1620
gaaagcaata ctggaagcac cactggttcc atagtgtgtg gttacaatgg ttggtctgat    1680
ttacccatat gttatgaaag agaatgcgaa cttcctaaaa tagatgtaca cttagttcct    1740
gatcgcaaga aagaccagta taaagttgga gaggtgttga aattctcctg caaaccagga    1800
tttacaatag ttggacctaa ttccgttcag tgctaccact ttggattgtc tcctgacctc    1860
ccaatatgta aagagcaagt acaatcatgt ggtccacctc ctgaactcct caatgggaat    1920
gttaaggaaa aaacgaaaga agaatatgga cacagtgaag tggtggaata ttattgcaat    1980
cctagatttc taatgaaggg acctaataaa attcaatgtg ttgatggaga gtggacaact    2040
ttaccagtgt gtattgtgga ggagagtacc tgtggagata tacctgaact tgaacatggc    2100
tgggcccagc tttcttcccc tccttattac tatggagatt cagtggaatt caattgctca    2160
gaatcattta caatgattgg acacagatca attacgtgta ttcatggagt atggacccaa    2220
cttccccagt gtgtggcaat agataaactt aagaagtgca aatcatcaaa tttaattata    2280
cttgaggaac atttaaaaaa caagaaggaa ttcgatcata attctaacat aaggtacaga    2340
tgtagaggaa aagaaggatg gatacacaca gtctgcataa atggaagatg ggatccagaa    2400
```

-continued

```
gtgaactgct caatggcaca aatacaatta tgcccacctc cacctcagat tcccaattct   2460

cacaatatga caaccacact gaattatcgg gatggagaaa aagtatctgt tctttgccaa   2520

gaaaattatc taattcagga aggagaagaa attacatgca aagatggaag atggcagtca   2580

ataccactct gtgttgaaaa aattccatgt tcacaaccac ctcagataga acacggaacc   2640

attaattcat ccaggtcttc acaagaaagt tatgcacatg ggactaaatt gagttatact   2700

tgtgagggtg gtttcaggat atctgaagaa aatgaaacaa catgctacat gggaaaatgg   2760

agttctccac ctcagtgtga aggccttcct tgtaaatctc cacctgagat ttctcatggt   2820

gttgtagctc acatgtcaga cagttatcag tatggagaag aagttacgta caaatgtttt   2880

gaaggttttg gaattgatgg gcctgcaatt gcaaaatgct taggagaaaa atggtctcac   2940

cctccatcat gcataaaaac agattgtctc agtttaccta gctttgaaaa tgccataccc   3000

atgggagaga agaaggatgt gtataaggcg ggtgagcaag tgacttacac ttgtgcaaca   3060

tattacaaaa tggatggagc cagtaatgta acatgcatta atagcagatg gacaggaagg   3120

ccaacatgca gagacacctc ctgtgtgaat ccgcccacag tacaaaatgc ttatatagtg   3180

tcgagacaga tgagtaaata tccatctggt gagagagtac gttatcaatg taggagccct   3240

tatgaaatgt ttggggatga agaagtgatg tgtttaaatg gaaactggac ggaaccacct   3300

caatgcaaag attctacagg aaaatgtggg ccccctccac ctattgacaa tggggacatt   3360

acttcattcc cgttgtcagt atatgctcca gcttcatcag ttgagtacca atgccagaac   3420

ttgtatcaac ttgagggtaa caagcgaata acatgtagaa atggacaatg gtcagaacca   3480

ccaaaatgct tacatccgtg tgtaatatcc cgagaaatta tggaaaatta taacatagca   3540

ttaaggtgga cagccaaaca gaagctttat tcgagaacag gtgaatcagt tgaatttgtg   3600

tgtaaacggg gatatcgtct ttcatcacgt tctcacacat tgcgaacaac atgttgggat   3660

gggaaactgg agtatccaac ttgtgcaaaa agatag                              3696

<210> SEQ ID NO 5
<211> LENGTH: 246
<212> TYPE: PRT
<213> ORGANISM: Homo sapiens

<400> SEQUENCE: 5

Glu Asp Cys Asn Glu Leu Pro Pro Arg Arg Asn Thr Glu Ile Leu Thr
1               5                   10                  15

Gly Ser Trp Ser Asp Gln Thr Tyr Pro Glu Gly Thr Gln Ala Ile Tyr
            20                  25                  30

Lys Cys Arg Pro Gly Tyr Arg Ser Leu Gly Asn Val Ile Met Val Cys
        35                  40                  45

Arg Lys Gly Glu Trp Val Ala Leu Asn Pro Leu Arg Lys Cys Gln Lys
    50                  55                  60

Arg Pro Cys Gly His Pro Gly Asp Thr Pro Phe Gly Thr Phe Thr Leu
65                  70                  75                  80

Thr Gly Gly Asn Val Phe Glu Tyr Gly Val Lys Ala Val Tyr Thr Cys
                85                  90                  95

Asn Glu Gly Tyr Gln Leu Leu Gly Glu Ile Asn Tyr Arg Glu Cys Asp
            100                 105                 110

Thr Asp Gly Trp Thr Asn Asp Ile Pro Ile Cys Glu Val Val Lys Cys
        115                 120                 125

Leu Pro Val Thr Ala Pro Glu Asn Gly Lys Ile Val Ser Ser Ala Met
    130                 135                 140
```

```
Glu Pro Asp Arg Glu Tyr His Phe Gly Gln Ala Val Arg Phe Val Cys
145                 150                 155                 160

Asn Ser Gly Tyr Lys Ile Glu Gly Asp Glu Glu Met His Cys Ser Asp
                165                 170                 175

Asp Gly Phe Trp Ser Lys Glu Lys Pro Lys Cys Val Glu Ile Ser Cys
            180                 185                 190

Lys Ser Pro Asp Val Ile Asn Gly Ser Pro Ile Ser Gln Lys Ile Ile
        195                 200                 205

Tyr Lys Glu Asn Glu Arg Phe Gln Tyr Lys Cys Asn Met Gly Tyr Glu
    210                 215                 220

Tyr Ser Glu Arg Gly Asp Ala Val Cys Thr Glu Ser Gly Trp Arg Pro
225                 230                 235                 240

Leu Pro Ser Cys Glu Glu
                245


<210> SEQ ID NO 6
<211> LENGTH: 489
<212> TYPE: PRT
<213> ORGANISM: Homo sapiens

<400> SEQUENCE: 6

Glu Asp Cys Asn Glu Leu Pro Pro Arg Arg Asn Thr Glu Ile Leu Thr
1               5                   10                  15

Gly Ser Trp Ser Asp Gln Thr Tyr Pro Glu Gly Thr Gln Ala Ile Tyr
            20                  25                  30

Lys Cys Arg Pro Gly Tyr Arg Ser Leu Gly Asn Val Ile Met Val Cys
        35                  40                  45

Arg Lys Gly Glu Trp Val Ala Leu Asn Pro Leu Arg Lys Cys Gln Lys
    50                  55                  60

Arg Pro Cys Gly His Pro Gly Asp Thr Pro Phe Gly Thr Phe Thr Leu
65                  70                  75                  80

Thr Gly Gly Asn Val Phe Glu Tyr Gly Val Lys Ala Val Tyr Thr Cys
                85                  90                  95

Asn Glu Gly Tyr Gln Leu Leu Gly Glu Ile Asn Tyr Arg Glu Cys Asp
            100                 105                 110

Thr Asp Gly Trp Thr Asn Asp Ile Pro Ile Cys Glu Val Val Lys Cys
        115                 120                 125

Leu Pro Val Thr Ala Pro Glu Asn Gly Lys Ile Val Ser Ser Ala Met
    130                 135                 140

Glu Pro Asp Arg Glu Tyr His Phe Gly Gln Ala Val Arg Phe Val Cys
145                 150                 155                 160

Asn Ser Gly Tyr Lys Ile Glu Gly Asp Glu Glu Met His Cys Ser Asp
                165                 170                 175

Asp Gly Phe Trp Ser Lys Glu Lys Pro Lys Cys Val Glu Ile Ser Cys
            180                 185                 190

Lys Ser Pro Asp Val Ile Asn Gly Ser Pro Ile Ser Gln Lys Ile Ile
        195                 200                 205

Tyr Lys Glu Asn Glu Arg Phe Gln Tyr Lys Cys Asn Met Gly Tyr Glu
    210                 215                 220

Tyr Ser Glu Arg Gly Asp Ala Val Cys Thr Glu Ser Gly Trp Arg Pro
225                 230                 235                 240

Leu Pro Ser Cys Glu Glu Lys Ser Cys Asp Asn Pro Tyr Ile Pro Asn
                245                 250                 255

Gly Asp Tyr Ser Pro Leu Arg Ile Lys His Arg Thr Gly Asp Glu Ile
```

```
            260                 265                 270

Thr Tyr Gln Cys Arg Asn Gly Phe Tyr Pro Ala Thr Arg Gly Asn Thr
        275                 280                 285

Ala Lys Cys Thr Ser Thr Gly Trp Ile Pro Ala Pro Arg Cys Thr Leu
    290                 295                 300

Lys Pro Cys Asp Tyr Pro Asp Ile Lys His Gly Gly Leu Tyr His Glu
305                 310                 315                 320

Asn Met Arg Arg Pro Tyr Phe Pro Val Ala Val Gly Lys Tyr Tyr Ser
                325                 330                 335

Tyr Tyr Cys Asp Glu His Phe Glu Thr Pro Ser Gly Ser Tyr Trp Asp
            340                 345                 350

His Ile His Cys Thr Gln Asp Gly Trp Ser Pro Ala Val Pro Cys Leu
        355                 360                 365

Arg Lys Cys Tyr Phe Pro Tyr Leu Glu Asn Gly Tyr Asn Gln Asn Tyr
    370                 375                 380

Gly Arg Lys Phe Val Gln Gly Lys Ser Ile Asp Val Ala Cys His Pro
385                 390                 395                 400

Gly Tyr Ala Leu Pro Lys Ala Gln Thr Thr Val Thr Cys Met Glu Asn
                405                 410                 415

Gly Trp Ser Pro Thr Pro Arg Cys Ile Arg Val Lys Thr Cys Ser Lys
            420                 425                 430

Ser Ser Ile Asp Ile Glu Asn Gly Phe Ile Ser Glu Ser Gln Tyr Thr
        435                 440                 445

Tyr Ala Leu Lys Glu Lys Ala Lys Tyr Gln Cys Lys Leu Gly Tyr Val
    450                 455                 460

Thr Ala Asp Gly Glu Thr Ser Gly Ser Ile Thr Cys Gly Lys Asp Gly
465                 470                 475                 480

Trp Ser Ala Gln Pro Thr Cys Ile Lys
                485


<210> SEQ ID NO 7
<211> LENGTH: 1086
<212> TYPE: PRT
<213> ORGANISM: Homo sapiens

<400> SEQUENCE: 7

Glu Asp Cys Asn Glu Leu Pro Pro Arg Arg Asn Thr Glu Ile Leu Thr
1               5                   10                  15

Gly Ser Trp Ser Asp Gln Thr Tyr Pro Glu Gly Thr Gln Ala Ile Tyr
            20                  25                  30

Lys Cys Arg Pro Gly Tyr Arg Ser Leu Gly Asn Val Ile Met Val Cys
        35                  40                  45

Arg Lys Gly Glu Trp Val Ala Leu Asn Pro Leu Arg Lys Cys Gln Lys
    50                  55                  60

Arg Pro Cys Gly His Pro Gly Asp Thr Pro Phe Gly Thr Phe Thr Leu
65                  70                  75                  80

Thr Gly Gly Asn Val Phe Glu Tyr Gly Val Lys Ala Val Tyr Thr Cys
                85                  90                  95

Asn Glu Gly Tyr Gln Leu Leu Gly Glu Ile Asn Tyr Arg Glu Cys Asp
            100                 105                 110

Thr Asp Gly Trp Thr Asn Asp Ile Pro Ile Cys Glu Val Val Lys Cys
        115                 120                 125

Leu Pro Val Thr Ala Pro Glu Asn Gly Lys Ile Val Ser Ser Ala Met
    130                 135                 140
```

-continued

```
Glu Pro Asp Arg Glu Tyr His Phe Gly Gln Ala Val Arg Phe Val Cys
145                 150                 155                 160

Asn Ser Gly Tyr Lys Ile Glu Gly Asp Glu Glu Met His Cys Ser Asp
                165                 170                 175

Asp Gly Phe Trp Ser Lys Glu Lys Pro Lys Cys Val Glu Ile Ser Cys
            180                 185                 190

Lys Ser Pro Asp Val Ile Asn Gly Ser Pro Ile Ser Gln Lys Ile Ile
        195                 200                 205

Tyr Lys Glu Asn Glu Arg Phe Gln Tyr Lys Cys Asn Met Gly Tyr Glu
    210                 215                 220

Tyr Ser Glu Arg Gly Asp Ala Val Cys Thr Glu Ser Gly Trp Arg Pro
225                 230                 235                 240

Leu Pro Ser Cys Glu Glu Lys Ser Cys Asp Asn Pro Tyr Ile Pro Asn
                245                 250                 255

Gly Asp Tyr Ser Pro Leu Arg Ile Lys His Arg Thr Gly Asp Glu Ile
            260                 265                 270

Thr Tyr Gln Cys Arg Asn Gly Phe Tyr Pro Ala Thr Arg Gly Asn Thr
        275                 280                 285

Ala Lys Cys Thr Ser Thr Gly Trp Ile Pro Ala Pro Arg Cys Thr Leu
    290                 295                 300

Lys Pro Cys Asp Tyr Pro Asp Ile Lys His Gly Gly Leu Tyr His Glu
305                 310                 315                 320

Asn Met Arg Arg Pro Tyr Phe Pro Val Ala Val Gly Lys Tyr Tyr Ser
                325                 330                 335

Tyr Tyr Cys Asp Glu His Phe Glu Thr Pro Ser Gly Ser Tyr Trp Asp
            340                 345                 350

His Ile His Cys Thr Gln Asp Gly Trp Ser Pro Ala Val Pro Cys Leu
        355                 360                 365

Arg Lys Cys Tyr Phe Pro Tyr Leu Glu Asn Gly Tyr Asn Gln Asn Tyr
    370                 375                 380

Gly Arg Lys Phe Val Gln Gly Lys Ser Ile Asp Val Ala Cys His Pro
385                 390                 395                 400

Gly Tyr Ala Leu Pro Lys Ala Gln Thr Thr Val Thr Cys Met Glu Asn
                405                 410                 415

Gly Trp Ser Pro Thr Pro Arg Cys Ile Arg Val Lys Thr Cys Ser Lys
            420                 425                 430

Ser Ser Ile Asp Ile Glu Asn Gly Phe Ile Ser Glu Ser Gln Tyr Thr
        435                 440                 445

Tyr Ala Leu Lys Glu Lys Ala Lys Tyr Gln Cys Lys Leu Gly Tyr Val
    450                 455                 460

Thr Ala Asp Gly Glu Thr Ser Gly Ser Ile Thr Cys Gly Lys Asp Gly
465                 470                 475                 480

Trp Ser Ala Gln Pro Thr Cys Ile Lys Ser Cys Asp Ile Pro Val Phe
                485                 490                 495

Met Asn Ala Arg Thr Lys Asn Asp Phe Thr Trp Phe Lys Leu Asn Asp
            500                 505                 510

Thr Leu Asp Tyr Glu Cys His Asp Gly Tyr Glu Ser Asn Thr Gly Ser
        515                 520                 525

Thr Thr Gly Ser Ile Val Cys Gly Tyr Asn Gly Trp Ser Asp Leu Pro
    530                 535                 540

Ile Cys Tyr Glu Arg Glu Cys Glu Leu Pro Lys Ile Asp Val His Leu
545                 550                 555                 560

Val Pro Asp Arg Lys Lys Asp Gln Tyr Lys Val Gly Glu Val Leu Lys
```

-continued

```
                565                 570                 575

Phe Ser Cys Lys Pro Gly Phe Thr Ile Val Gly Pro Asn Ser Val Gln
            580                 585                 590

Cys Tyr His Phe Gly Leu Ser Pro Asp Leu Pro Ile Cys Lys Glu Gln
        595                 600                 605

Val Gln Ser Cys Gly Pro Pro Pro Glu Leu Leu Asn Gly Asn Val Lys
    610                 615                 620

Glu Lys Thr Lys Glu Glu Tyr Gly His Ser Glu Val Val Glu Tyr Tyr
625                 630                 635                 640

Cys Asn Pro Arg Phe Leu Met Lys Gly Pro Asn Lys Ile Gln Cys Val
                645                 650                 655

Asp Gly Glu Trp Thr Thr Leu Pro Val Cys Ile Val Glu Glu Ser Thr
            660                 665                 670

Cys Gly Asp Ile Pro Glu Leu Glu His Gly Trp Ala Gln Leu Ser Ser
        675                 680                 685

Pro Pro Tyr Tyr Tyr Gly Asp Ser Val Glu Phe Asn Cys Ser Glu Ser
    690                 695                 700

Phe Thr Met Ile Gly His Arg Ser Ile Thr Cys Ile His Gly Val Trp
705                 710                 715                 720

Thr Gln Leu Pro Gln Cys Val Ala Ile Asp Lys Leu Lys Lys Cys Lys
                725                 730                 735

Ser Ser Asn Leu Ile Ile Leu Glu Glu His Leu Lys Asn Lys Lys Glu
            740                 745                 750

Phe Asp His Asn Ser Asn Ile Arg Tyr Arg Cys Arg Gly Lys Glu Gly
        755                 760                 765

Trp Ile His Thr Val Cys Ile Asn Gly Arg Trp Asp Pro Glu Val Asn
    770                 775                 780

Cys Ser Met Ala Gln Ile Gln Leu Cys Pro Pro Pro Pro Gln Ile Pro
785                 790                 795                 800

Asn Ser His Asn Met Thr Thr Thr Leu Asn Tyr Arg Asp Gly Glu Lys
                805                 810                 815

Val Ser Val Leu Cys Gln Glu Asn Tyr Leu Ile Gln Glu Gly Glu Glu
            820                 825                 830

Ile Thr Cys Lys Asp Gly Arg Trp Gln Ser Ile Pro Leu Cys Val Glu
        835                 840                 845

Lys Ile Pro Cys Ser Gln Pro Pro Gln Ile Glu His Gly Thr Ile Asn
    850                 855                 860

Ser Ser Arg Ser Ser Gln Glu Ser Tyr Ala His Gly Thr Lys Leu Ser
865                 870                 875                 880

Tyr Thr Cys Glu Gly Gly Phe Arg Ile Ser Glu Glu Asn Glu Thr Thr
                885                 890                 895

Cys Tyr Met Gly Lys Trp Ser Ser Pro Pro Gln Cys Glu Gly Leu Pro
            900                 905                 910

Cys Lys Ser Pro Pro Glu Ile Ser His Gly Val Val Ala His Met Ser
        915                 920                 925

Asp Ser Tyr Gln Tyr Gly Glu Glu Val Thr Tyr Lys Cys Phe Glu Gly
    930                 935                 940

Phe Gly Ile Asp Gly Pro Ala Ile Ala Lys Cys Leu Gly Glu Lys Trp
945                 950                 955                 960

Ser His Pro Pro Ser Cys Ile Lys Thr Asp Cys Leu Ser Leu Pro Ser
                965                 970                 975

Phe Glu Asn Ala Ile Pro Met Gly Glu Lys Lys Asp Val Tyr Lys Ala
            980                 985                 990
```

-continued

```
Gly Glu Gln Val Thr Tyr Thr Cys  Ala Thr Tyr Tyr Lys  Met Asp Gly
        995                 1000                 1005

Ala Ser  Asn Val Thr Cys Ile  Asn Ser Arg Trp Thr  Gly Arg Pro
    1010                 1015                 1020

Thr Cys  Arg Asp Thr Ser Cys  Val Asn Pro Pro Thr  Val Gln Asn
    1025                 1030                 1035

Ala Tyr  Ile Val Ser Arg Gln  Met Ser Lys Tyr Pro  Ser Gly Glu
    1040                 1045                 1050

Arg Val  Arg Tyr Gln Cys Arg  Ser Pro Tyr Glu Met  Phe Gly Asp
    1055                 1060                 1065

Glu Glu  Val Met Cys Leu Asn  Gly Asn Trp Thr Glu  Pro Pro Gln
    1070                 1075                 1080

Cys Lys  Asp
    1085


<210> SEQ ID NO 8
<211> LENGTH: 127
<212> TYPE: PRT
<213> ORGANISM: Homo sapiens

<400> SEQUENCE: 8

Ser Thr Gly Lys Cys Gly Pro Pro Pro Pro Ile Asp Asn Gly Asp Ile
1               5                   10                  15

Thr Ser Phe Pro Leu Ser Val Tyr Ala Pro Ala Ser Ser Val Glu Tyr
            20                  25                  30

Gln Cys Gln Asn Leu Tyr Gln Leu Glu Gly Asn Lys Arg Ile Thr Cys
        35                  40                  45

Arg Asn Gly Gln Trp Ser Glu Pro Pro Lys Cys Leu His Pro Cys Val
    50                  55                  60

Ile Ser Arg Glu Ile Met Glu Asn Tyr Asn Ile Ala Leu Arg Trp Thr
65                  70                  75                  80

Ala Lys Gln Lys Leu Tyr Ser Arg Thr Gly Glu Ser Val Glu Phe Val
                85                  90                  95

Cys Lys Arg Gly Tyr Arg Leu Ser Ser Arg Ser His Thr Leu Arg Thr
            100                 105                 110

Thr Cys Trp Asp Gly Lys Leu Glu Tyr Pro Thr Cys Ala Lys Arg
        115                 120                 125


<210> SEQ ID NO 9
<211> LENGTH: 1234
<212> TYPE: PRT
<213> ORGANISM: Mus musculus

<400> SEQUENCE: 9

Met Arg Leu Ser Ala Arg Ile Ile Trp Leu Ile Leu Trp Thr Val Cys
1               5                   10                  15

Ala Ala Glu Asp Cys Lys Gly Pro Pro Pro Arg Glu Asn Ser Glu Ile
            20                  25                  30

Leu Ser Gly Ser Trp Ser Glu Gln Leu Tyr Pro Glu Gly Thr Gln Ala
        35                  40                  45

Thr Tyr Lys Cys Arg Pro Gly Tyr Arg Thr Leu Gly Thr Ile Val Lys
    50                  55                  60

Val Cys Lys Asn Gly Lys Trp Val Ala Ser Asn Pro Ser Arg Ile Cys
65                  70                  75                  80

Arg Lys Lys Pro Cys Gly His Pro Gly Asp Thr Pro Phe Gly Ser Phe
                85                  90                  95
```

-continued

```
Arg Leu Ala Val Gly Ser Gln Phe Glu Phe Gly Ala Lys Val Val Tyr
            100                 105                 110

Thr Cys Asp Asp Gly Tyr Gln Leu Leu Gly Glu Ile Asp Tyr Arg Glu
        115                 120                 125

Cys Gly Ala Asp Gly Trp Ile Asn Asp Ile Pro Leu Cys Glu Val Val
    130                 135                 140

Lys Cys Leu Pro Val Thr Glu Leu Glu Asn Gly Arg Ile Val Ser Gly
145                 150                 155                 160

Ala Ala Glu Thr Asp Gln Glu Tyr Tyr Phe Gly Gln Val Val Arg Phe
                165                 170                 175

Glu Cys Asn Ser Gly Phe Lys Ile Glu Gly His Lys Glu Ile His Cys
            180                 185                 190

Ser Glu Asn Gly Leu Trp Ser Asn Glu Lys Pro Arg Cys Val Glu Ile
        195                 200                 205

Leu Cys Thr Pro Pro Arg Val Glu Asn Gly Asp Gly Ile Asn Val Lys
    210                 215                 220

Pro Val Tyr Lys Glu Asn Glu Arg Tyr His Tyr Lys Cys Lys His Gly
225                 230                 235                 240

Tyr Val Pro Lys Glu Arg Gly Asp Ala Val Cys Thr Gly Ser Gly Trp
                245                 250                 255

Ser Ser Gln Pro Phe Cys Glu Glu Lys Arg Cys Ser Pro Pro Tyr Ile
            260                 265                 270

Leu Asn Gly Ile Tyr Thr Pro His Arg Ile Ile His Arg Ser Asp Asp
        275                 280                 285

Glu Ile Arg Tyr Glu Cys Asn Tyr Gly Phe Tyr Pro Val Thr Gly Ser
    290                 295                 300

Thr Val Ser Lys Cys Thr Pro Thr Gly Trp Ile Pro Val Pro Arg Cys
305                 310                 315                 320

Thr Leu Lys Pro Cys Glu Phe Pro Gln Phe Lys Tyr Gly Arg Leu Tyr
                325                 330                 335

Tyr Glu Glu Ser Leu Arg Pro Asn Phe Pro Val Ser Ile Gly Asn Lys
            340                 345                 350

Tyr Ser Tyr Lys Cys Asp Asn Gly Phe Ser Pro Pro Ser Gly Tyr Ser
        355                 360                 365

Trp Asp Tyr Leu Arg Cys Thr Ala Gln Gly Trp Glu Pro Glu Val Pro
    370                 375                 380

Cys Val Arg Lys Cys Val Phe His Tyr Val Glu Asn Gly Asp Ser Ala
385                 390                 395                 400

Tyr Trp Glu Lys Val Tyr Val Gln Gly Gln Ser Leu Lys Val Gln Cys
                405                 410                 415

Tyr Asn Gly Tyr Ser Leu Gln Asn Gly Gln Asp Thr Met Thr Cys Thr
            420                 425                 430

Glu Asn Gly Trp Ser Pro Pro Pro Lys Cys Ile Arg Ile Lys Thr Cys
        435                 440                 445

Ser Ala Ser Asp Ile His Ile Asp Asn Gly Phe Leu Ser Glu Ser Ser
    450                 455                 460

Ser Ile Tyr Ala Leu Asn Arg Glu Thr Ser Tyr Arg Cys Lys Gln Gly
465                 470                 475                 480

Tyr Val Thr Asn Thr Gly Glu Ile Ser Gly Ser Ile Thr Cys Leu Gln
                485                 490                 495

Asn Gly Trp Ser Pro Gln Pro Ser Cys Ile Lys Ser Cys Asp Met Pro
            500                 505                 510
```

```
Val Phe Glu Asn Ser Ile Thr Lys Asn Thr Arg Thr Trp Phe Lys Leu
        515                 520                 525

Asn Asp Lys Leu Asp Tyr Glu Cys Leu Val Gly Phe Glu Asn Glu Tyr
    530                 535                 540

Lys His Thr Lys Gly Ser Ile Thr Cys Thr Tyr Tyr Gly Trp Ser Asp
545                 550                 555                 560

Thr Pro Ser Cys Tyr Glu Arg Glu Cys Ser Val Pro Thr Leu Asp Arg
                565                 570                 575

Lys Leu Val Val Ser Pro Arg Lys Glu Lys Tyr Arg Val Gly Asp Leu
            580                 585                 590

Leu Glu Phe Ser Cys His Ser Gly His Arg Val Gly Pro Asp Ser Val
        595                 600                 605

Gln Cys Tyr His Phe Gly Trp Ser Pro Gly Phe Pro Thr Cys Lys Gly
    610                 615                 620

Gln Val Ala Ser Cys Ala Pro Pro Leu Glu Ile Leu Asn Gly Glu Ile
625                 630                 635                 640

Asn Gly Ala Lys Lys Val Glu Tyr Ser His Gly Glu Val Val Lys Tyr
                645                 650                 655

Asp Cys Lys Pro Arg Phe Leu Leu Lys Gly Pro Asn Lys Ile Gln Cys
            660                 665                 670

Val Asp Gly Asn Trp Thr Thr Leu Pro Val Cys Ile Glu Glu Glu Arg
        675                 680                 685

Thr Cys Gly Asp Ile Pro Glu Leu Glu His Gly Ser Ala Lys Cys Ser
    690                 695                 700

Val Pro Pro Tyr His His Gly Asp Ser Val Glu Phe Ile Cys Glu Glu
705                 710                 715                 720

Asn Phe Thr Met Ile Gly His Gly Ser Val Ser Cys Ile Ser Gly Lys
                725                 730                 735

Trp Thr Gln Leu Pro Lys Cys Val Ala Thr Asp Gln Leu Glu Lys Cys
            740                 745                 750

Arg Val Leu Lys Ser Thr Gly Ile Glu Ala Ile Lys Pro Lys Leu Thr
        755                 760                 765

Glu Phe Thr His Asn Ser Thr Met Asp Tyr Lys Cys Arg Asp Lys Gln
    770                 775                 780

Glu Tyr Glu Arg Ser Ile Cys Ile Asn Gly Lys Trp Asp Pro Glu Pro
785                 790                 795                 800

Asn Cys Thr Ser Lys Thr Ser Cys Pro Pro Pro Pro Gln Ile Pro Asn
                805                 810                 815

Thr Gln Val Ile Glu Thr Thr Val Lys Tyr Leu Asp Gly Glu Lys Leu
            820                 825                 830

Ser Val Leu Cys Gln Asp Asn Tyr Leu Thr Gln Asp Ser Glu Glu Met
        835                 840                 845

Val Cys Lys Asp Gly Arg Trp Gln Ser Leu Pro Arg Cys Ile Glu Lys
    850                 855                 860

Ile Pro Cys Ser Gln Pro Pro Thr Ile Glu His Gly Ser Ile Asn Leu
865                 870                 875                 880

Pro Arg Ser Ser Glu Glu Arg Arg Asp Ser Ile Glu Ser Ser Ser His
                885                 890                 895

Glu His Gly Thr Thr Phe Ser Tyr Val Cys Asp Asp Gly Phe Arg Ile
            900                 905                 910

Pro Glu Glu Asn Arg Ile Thr Cys Tyr Met Gly Lys Trp Ser Thr Pro
        915                 920                 925

Pro Arg Cys Val Gly Leu Pro Cys Gly Pro Pro Pro Ser Ile Pro Leu
```

```
    930                 935                 940

Gly Thr Val Ser Leu Glu Leu Glu Ser Tyr Gln His Gly Glu Glu Val
945                 950                 955                 960

Thr Tyr His Cys Ser Thr Gly Phe Gly Ile Asp Gly Pro Ala Phe Ile
                965                 970                 975

Ile Cys Glu Gly Gly Lys Trp Ser Asp Pro Pro Lys Cys Ile Lys Thr
            980                 985                 990

Asp Cys Asp Val Leu Pro Thr Val  Lys Asn Ala Ile Ile  Arg Gly Lys
        995                 1000                1005

Ser Lys  Lys Ser Tyr Arg Thr  Gly Glu Gln Val Thr  Phe Arg Cys
    1010                 1015                1020

Gln Ser  Pro Tyr Gln Met Asn  Gly Ser Asp Thr Val  Thr Cys Val
    1025                 1030                1035

Asn Ser  Arg Trp Ile Gly Gln  Pro Val Cys Lys Asp  Asn Ser Cys
    1040                 1045                1050

Val Asp  Pro Pro His Val Pro  Asn Ala Thr Ile Val  Thr Arg Thr
    1055                 1060                1065

Lys Asn  Lys Tyr Leu His Gly  Asp Arg Val Arg Tyr  Glu Cys Asn
    1070                 1075                1080

Lys Pro  Leu Glu Leu Phe Gly  Gln Val Glu Val Met  Cys Glu Asn
    1085                 1090                1095

Gly Ile  Trp Thr Glu Lys Pro  Lys Cys Arg Asp Ser  Thr Gly Lys
    1100                 1105                1110

Cys Gly  Pro Pro Pro Pro Ile  Asp Asn Gly Asp Ile  Thr Ser Leu
    1115                 1120                1125

Ser Leu  Pro Val Tyr Glu Pro  Leu Ser Ser Val Glu  Tyr Gln Cys
    1130                 1135                1140

Gln Lys  Tyr Tyr Leu Leu Lys  Gly Lys Lys Thr Ile  Thr Cys Thr
    1145                 1150                1155

Asn Gly  Lys Trp Ser Glu Pro  Pro Thr Cys Leu His  Ala Cys Val
    1160                 1165                1170

Ile Pro  Glu Asn Ile Met Glu  Ser His Asn Ile Ile  Leu Lys Trp
    1175                 1180                1185

Arg His  Thr Glu Lys Ile Tyr  Ser His Ser Gly Glu  Asp Ile Glu
    1190                 1195                1200

Phe Gly  Cys Lys Tyr Gly Tyr  Tyr Lys Ala Arg Asp  Ser Pro Pro
    1205                 1210                1215

Phe Arg  Thr Lys Cys Ile Asn  Gly Thr Ile Asn Tyr  Pro Thr Cys
    1220                 1225                1230

Val
```

<210> SEQ ID NO 10
<211> LENGTH: 3705
<212> TYPE: DNA
<213> ORGANISM: Mus musculus

<400> SEQUENCE: 10

```
atgagactgt cagcaagaat tatttggctt atattatgga ctgtttgtgc agcagaagat     60

tgtaaaggtc ctcctccaag agaaaattca gaaattctct caggctcgtg gtcagaacaa    120

ctatatccag aaggcaccca ggctacctac aaatgccgcc ctggataccg aacacttggc    180

actattgtaa aagtatgcaa gaatggaaaa tgggtggcgt ctaacccatc caggatatgt    240

cggaaaaagc cttgtgggca tcccggagac acaccctttg ggtcctttag gctggcagtt    300
```

-continued

```
ggatctcaat ttgagtttgg tgcaaaggtt gtttatacct gtgatgatgg gtatcaacta    360
ttaggtgaaa ttgattaccg tgaatgtggt gcagatggct ggatcaatga tattccacta    420
tgtgaagttg tgaagtgtct acctgtgaca gaactcgaga atggaagaat tgtgagtggt    480
gcagcagaaa cagaccagga atactatttt ggacaggtgg tgcggtttga atgcaattca    540
ggcttcaaga ttgaaggaca taaggaaatt cattgctcag aaaatggcct ttggagcaat    600
gaaaagccac gatgtgtgga aattctctgc acaccaccgc gagtggaaaa tggagatggt    660
ataaatgtga aaccagttta caaggagaat gaaagatacc actataagtg taagcatggt    720
tatgtgccca aagaaagagg ggatgccgtc tgcacaggct ctggatggag ttctcagcct    780
ttctgtgaag aaaagagatg ctcacctcct tatattctaa atggtatcta cacacctcac    840
aggattatac acagaagtga tgatgaaatc agatatgaat gtaattatgg cttctatcct    900
gtaactggat caactgtttc aaagtgtaca cccactggct ggatccctgt tccaagatgt    960
accttgaaac catgtgaatt tccacaattc aaatatggac gtctgtatta tgaagagagc   1020
ctgagaccca acttcccagt atctatagga aataagtaca gctataagtg tgacaacggg   1080
ttttcaccac cttctgggta ttcctgggac taccttcgtt gcacagcaca agggtgggag   1140
cctgaagtcc catgcgtcag gaaatgtgtt ttccattatg tggagaatgg agactctgca   1200
tactgggaaa aagtatatgt gcagggtcag tctttaaaag tccagtgtta caatggctat   1260
agtcttcaaa atggtcaaga cacaatgaca tgtacagaga atggctggtc ccctcctccc   1320
aaatgcatcc gtatcaagac atgttcagca tcagatatac acattgacaa tggatttctt   1380
tctgaatctt cttctatata tgctctaaat agagaaacat cctatagatg taagcaggga   1440
tatgtgacaa atactggaga aatatcagga tcaataactt gccttcaaaa tggatggtca   1500
cctcaaccct catgcattaa gtcttgtgat atgcctgtat ttgagaattc tataactaag   1560
aatactagga catggtttaa gctcaatgac aaattagact atgaatgtct cgttggattt   1620
gaaaatgaat ataaacatac caaaggctct ataacatgta cttattatgg atggtctgat   1680
acaccctcat gttatgaaag agaatgcagt gttcccactc tagaccgaaa actagtcgtt   1740
tcccccagaa aagaaaaata cagagttgga gatttgttgg aattctcctg ccattcagga   1800
cacagagttg ggccagattc agtgcaatgc taccactttg gatggtctcc tggtttccct   1860
acatgtaaag gtcaagtagc atcatgtgca ccacctcttg aaattcttaa tggggaaatt   1920
aatggagcaa aaaaagttga atacagccat ggtgaagtgg tgaaatatga ttgcaaacct   1980
agattcctac tgaagggacc caataaaatc cagtgtgttg atgggaattg gacaaccttg   2040
cctgtatgta ttgaggagga gagaacatgt ggagacattc ctgaacttga acatggctct   2100
gccaagtgtt ctgttcctcc ctaccaccat ggagattcag tggagttcat ttgtgaagaa   2160
aacttcacaa tgattggaca tgggtcagtt tcttgcatta gtggaaaatg gacccagctt   2220
cctaaatgtg ttgcaacaga ccaactggag aagtgtagag tgctgaagtc aactggcata   2280
gaagcaataa aaccaaaatt gactgaattt acgcataact ccaccatgga ttacaaatgt   2340
agagacaagc aggagtacga acgctcaatc tgtatcaatg gaaaatggga tcctgaacca   2400
aactgtacaa gcaaaacatc ctgccctcct ccaccgcaga ttccaaatac ccaagtgatt   2460
gaaaccaccg tgaaatactt ggatggagaa aaattatctg ttctttgcca agacaattac   2520
ctaactcagg actcagaaga aatggtgtgc aaagatggaa ggtggcagtc attacctcgc   2580
tgcattgaaa aaattccatg ttcccagccc cctacaatag aacatggatc tattaattta   2640
cccagatctt cagaagaaag gagagattcc attgagtcca gcagtcatga acatggaact   2700
```

acattcagct atgtctgtga tgatggtttc aggatacctg aagaaaatag gataacctgc 2760
tacatgggaa aatggagcac tccacctcgc tgtgttggac ttccttgtgg acctccacct 2820
tcaattcctc ttggtactgt ttctcttgag ctagagagtt accaacatgg ggaagaggtt 2880
acataccatt gttctacagg ctttggaatt gatggaccag catttattat atgcgaagga 2940
ggaaagtggt ctgacccacc aaaatgcata aaaacggatt gtgacgtttt acccacagtt 3000
aaaaatgcca taataagagg aaagagcaaa aaatcatata ggacaggaga acaagtgaca 3060
ttcagatgtc aatctcctta tcaaatgaat ggctcagaca ctgtgacatg tgttaatagt 3120
cggtggattg gacagccagt atgcaaagat aattcctgtg tggatccacc acatgtgcca 3180
aatgctacta tagtaacaag gaccaagaat aaatatctac atggtgacag agtacgttat 3240
gaatgtaata aacctttgga actatttggg caagtggaag tgatgtgtga aaatgggata 3300
tggacagaaa aaccaaagtg ccgagactca acagggaaat gtgggcctcc tccacctatt 3360
gacaatggag acatcacctc cttgtcatta ccagtatatg aaccattatc atcagttgaa 3420
tatcaatgcc agaagtatta tctccttaag ggaaagaaga caataacatg tacaaatgga 3480
aagtggtctg agccaccaac atgcttacat gcatgtgtaa taccagaaaa cattatggaa 3540
tcacacaata taattctcaa atggagacac actgaaaaga tttattccca ttcaggggag 3600
gatattgaat ttggatgtaa atatggatat tataaagcaa gagattcacc gccatttcgt 3660
acaaagtgca ttaatggcac catcaattat cccacttgtg tataa 3705

<210> SEQ ID NO 11
<211> LENGTH: 21
<212> TYPE: PRT
<213> ORGANISM: Homo sapiens

<400> SEQUENCE: 11

Met Pro Met Gly Ser Leu Gln Pro Leu Ala Thr Leu Tyr Leu Leu Gly
1               5                   10                  15

Met Leu Val Ala Ser
            20

<210> SEQ ID NO 12
<211> LENGTH: 72
<212> TYPE: DNA
<213> ORGANISM: Homo sapiens

<400> SEQUENCE: 12
atgcccatgg ggtctctgca accgctggcc accttgtacc tgctggggat gctggtcgct 60
tcctgcctcg ga 72

<210> SEQ ID NO 13
<211> LENGTH: 17
<212> TYPE: PRT
<213> ORGANISM: Homo sapiens

<400> SEQUENCE: 13

Met Gly Ala Ala Gly Leu Leu Gly Val Phe Leu Ala Leu Val Ala Pro
1               5                   10                  15

Gly

<210> SEQ ID NO 14
<211> LENGTH: 51
<212> TYPE: DNA
<213> ORGANISM: Homo sapiens

<400> SEQUENCE: 14
atgggcgccg cgggcctgct cggggttttc ttggctctcg tcgcaccggg g 51

<210> SEQ ID NO 15
<211> LENGTH: 20
<212> TYPE: PRT
<213> ORGANISM: Homo sapiens

<400> SEQUENCE: 15

Met Gly Ala Ala Gly Leu Leu Gly Val Phe Leu Ala Leu Val Ala Pro
1 5 10 15

Gly Val Leu Gly
20

<210> SEQ ID NO 16
<211> LENGTH: 60
<212> TYPE: DNA
<213> ORGANISM: Homo sapiens

<400> SEQUENCE: 16
atgggagccg ctggtctgct cggcgtgttc ctcgccttgg tggcacctgg cgtcctgggc 60

<210> SEQ ID NO 17
<211> LENGTH: 381
<212> TYPE: PRT
<213> ORGANISM: Homo sapiens

<400> SEQUENCE: 17

Met Thr Val Ala Arg Pro Ser Val Pro Ala Ala Leu Pro Leu Leu Gly
1 5 10 15

Glu Leu Pro Arg Leu Leu Leu Leu Val Leu Leu Cys Leu Pro Ala Val
20 25 30

Trp Gly Asp Cys Gly Leu Pro Pro Asp Val Pro Asn Ala Gln Pro Ala
35 40 45

Leu Glu Gly Arg Thr Ser Phe Pro Glu Asp Thr Val Ile Thr Tyr Lys
50 55 60

Cys Glu Glu Ser Phe Val Lys Ile Pro Gly Glu Lys Asp Ser Val Ile
65 70 75 80

Cys Leu Lys Gly Ser Gln Trp Ser Asp Ile Glu Glu Phe Cys Asn Arg
85 90 95

Ser Cys Glu Val Pro Thr Arg Leu Asn Ser Ala Ser Leu Lys Gln Pro
100 105 110

Tyr Ile Thr Gln Asn Tyr Phe Pro Val Gly Thr Val Val Glu Tyr Glu
115 120 125

Cys Arg Pro Gly Tyr Arg Arg Glu Pro Ser Leu Ser Pro Lys Leu Thr
130 135 140

Cys Leu Gln Asn Leu Lys Trp Ser Thr Ala Val Glu Phe Cys Lys Lys
145 150 155 160

Lys Ser Cys Pro Asn Pro Gly Glu Ile Arg Asn Gly Gln Ile Asp Val
165 170 175

Pro Gly Gly Ile Leu Phe Gly Ala Thr Ile Ser Phe Ser Cys Asn Thr
180 185 190

Gly Tyr Lys Leu Phe Gly Ser Thr Ser Ser Phe Cys Leu Ile Ser Gly
195 200 205

Ser Ser Val Gln Trp Ser Asp Pro Leu Pro Glu Cys Arg Glu Ile Tyr
210 215 220

-continued

```
Cys Pro Ala Pro Pro Gln Ile Asp Asn Gly Ile Ile Gln Gly Glu Arg
225                 230                 235                 240

Asp His Tyr Gly Tyr Arg Gln Ser Val Thr Tyr Ala Cys Asn Lys Gly
                245                 250                 255

Phe Thr Met Ile Gly Glu His Ser Ile Tyr Cys Thr Val Asn Asn Asp
            260                 265                 270

Glu Gly Glu Trp Ser Gly Pro Pro Pro Glu Cys Arg Gly Lys Ser Leu
        275                 280                 285

Thr Ser Lys Val Pro Pro Thr Val Gln Lys Pro Thr Thr Val Asn Val
    290                 295                 300

Pro Thr Thr Glu Val Ser Pro Thr Ser Gln Lys Thr Thr Thr Lys Thr
305                 310                 315                 320

Thr Thr Pro Asn Ala Gln Ala Thr Arg Ser Thr Pro Val Ser Arg Thr
                325                 330                 335

Thr Lys His Phe His Glu Thr Thr Pro Asn Lys Gly Ser Gly Thr Thr
            340                 345                 350

Ser Gly Thr Thr Arg Leu Leu Ser Gly His Thr Cys Phe Thr Leu Thr
        355                 360                 365

Gly Leu Leu Gly Thr Leu Val Thr Met Gly Leu Leu Thr
    370                 375                 380


<210> SEQ ID NO 18
<211> LENGTH: 1146
<212> TYPE: DNA
<213> ORGANISM: Homo sapiens

<400> SEQUENCE: 18

atgaccgtcg cgcggccgag cgtgcccgcg gcgctgcccc tcctcgggga gctgccccgg      60

ctgctgctgc tggtgctgtt gtgcctgccg gccgtgtggg gtgactgtgg ccttccccca     120

gatgtaccta atgcccagcc agctttggaa ggccgtacaa gttttcccga ggatactgta     180

ataacgtaca aatgtgaaga aagctttgtg aaaattcctg gcgagaagga ctcagtgatc     240

tgccttaagg gcagtcaatg gtcagatatt gaagagttct gcaatcgtag ctgcgaggtg     300

ccaacaaggc taaattctgc atccctcaaa cagccttata tcactcagaa ttattttcca     360

gtcggtactg ttgtggaata tgagtgccgt ccaggttaca gaagagaacc ttctctatca     420

ccaaaactaa cttgccttca gaatttaaaa tggtccacag cagtcgaatt ttgtaaaaag     480

aaatcatgcc ctaatccggg agaaatacga aatggtcaga ttgatgtacc aggtggcata     540

ttatttggtg caaccatctc cttctcatgt aacacagggt acaaattatt tggctcgact     600

tctagttttt gtcttatttc aggcagctct gtccagtgga gtgacccgtt gccagagtgc     660

agagaaattt attgtccagc accaccacaa attgacaatg gaataattca aggggaacgt     720

gaccattatg gatatagaca gtctgtaacg tatgcatgta ataaaggatt caccatgatt     780

ggagagcact ctatttattg tactgtgaat aatgatgaag gagagtggag tggcccacca     840

cctgaatgca gaggaaaatc tctaacttcc aaggtcccac caacagttca gaaacctacc     900

acagtaaatg ttccaactac agaagtctca ccaacttctc agaaaaccac cacaaaaacc     960

accacaccaa atgctcaagc aacacggagt acacctgttt ccaggacaac caagcatttt    1020

catgaaacaa ccccaaataa aggaagtgga accacttcag gtactacccg tcttctatct    1080

gggcacacgt gtttcacgtt gacaggtttg cttgggacgc tagtaaccat gggcttgctg    1140

acttag                                                               1146
```

<210> SEQ ID NO 19
<211> LENGTH: 392
<212> TYPE: PRT
<213> ORGANISM: Homo sapiens

<400> SEQUENCE: 19

```
Met Glu Pro Pro Gly Arg Arg Glu Cys Pro Phe Pro Ser Trp Arg Phe
1               5                   10                  15

Pro Gly Leu Leu Leu Ala Ala Met Val Leu Leu Leu Tyr Ser Phe Ser
            20                  25                  30

Asp Ala Cys Glu Glu Pro Pro Thr Phe Glu Ala Met Glu Leu Ile Gly
        35                  40                  45

Lys Pro Lys Pro Tyr Tyr Glu Ile Gly Glu Arg Val Asp Tyr Lys Cys
    50                  55                  60

Lys Lys Gly Tyr Phe Tyr Ile Pro Pro Leu Ala Thr His Thr Ile Cys
65                  70                  75                  80

Asp Arg Asn His Thr Trp Leu Pro Val Ser Asp Asp Ala Cys Tyr Arg
                85                  90                  95

Glu Thr Cys Pro Tyr Ile Arg Asp Pro Leu Asn Gly Gln Ala Val Pro
            100                 105                 110

Ala Asn Gly Thr Tyr Glu Phe Gly Tyr Gln Met His Phe Ile Cys Asn
        115                 120                 125

Glu Gly Tyr Tyr Leu Ile Gly Glu Glu Ile Leu Tyr Cys Glu Leu Lys
    130                 135                 140

Gly Ser Val Ala Ile Trp Ser Gly Lys Pro Pro Ile Cys Glu Lys Val
145                 150                 155                 160

Leu Cys Thr Pro Pro Pro Lys Ile Lys Asn Gly Lys His Thr Phe Ser
                165                 170                 175

Glu Val Glu Val Phe Glu Tyr Leu Asp Ala Val Thr Tyr Ser Cys Asp
            180                 185                 190

Pro Ala Pro Gly Pro Asp Pro Phe Ser Leu Ile Gly Glu Ser Thr Ile
        195                 200                 205

Tyr Cys Gly Asp Asn Ser Val Trp Ser Arg Ala Ala Pro Glu Cys Lys
    210                 215                 220

Val Val Lys Cys Arg Phe Pro Val Val Glu Asn Gly Lys Gln Ile Ser
225                 230                 235                 240

Gly Phe Gly Lys Lys Phe Tyr Tyr Lys Ala Thr Val Met Phe Glu Cys
                245                 250                 255

Asp Lys Gly Phe Tyr Leu Asp Gly Ser Asp Thr Ile Val Cys Asp Ser
            260                 265                 270

Asn Ser Thr Trp Asp Pro Pro Val Pro Lys Cys Leu Lys Val Leu Pro
        275                 280                 285

Pro Ser Ser Thr Lys Pro Pro Ala Leu Ser His Ser Val Ser Thr Ser
    290                 295                 300

Ser Thr Thr Lys Ser Pro Ala Ser Ser Ala Ser Gly Pro Arg Pro Thr
305                 310                 315                 320

Tyr Lys Pro Pro Val Ser Asn Tyr Pro Gly Tyr Pro Lys Pro Glu Glu
                325                 330                 335

Gly Ile Leu Asp Ser Leu Asp Val Trp Val Ile Ala Val Ile Val Ile
            340                 345                 350

Ala Ile Val Val Gly Val Ala Val Ile Cys Val Val Pro Tyr Arg Tyr
        355                 360                 365

Leu Gln Arg Arg Lys Lys Lys Gly Thr Tyr Leu Thr Asp Glu Thr His
    370                 375                 380
```

Arg Glu Val Lys Phe Thr Ser Leu
385 390

<210> SEQ ID NO 20
<211> LENGTH: 1134
<212> TYPE: DNA
<213> ORGANISM: Homo sapiens

<400> SEQUENCE: 20
atggagcctc ccggccgccg cgagtgtccc tttccttcct ggcgctttcc tgggttgctt 60
ctggcggcca tggtgttgct gctgtactcc ttctccgatg cctgtgagga gccaccaaca 120
tttgaagcta tggagctcat tggtaaacca aaaccctact atgagattgg tgaacgagta 180
gattataagt gtaaaaaagg atacttctat atacctcctc ttgccaccca tactatttgt 240
gatcggaatc atacatggct acctgtctca gatgacgcct gttatagaga aacatgtcca 300
tatatacggg atcctttaaa tggccaagca gtccctgcaa atgggactta cgagtttggt 360
tatcagatgc actttatttg taatgagggt tattacttaa ttggtgaaga aattctatat 420
tgtgaactta aaggatcagt agcaatttgg agcggtaagc ccccaatatg tgaaaaggtt 480
ttgtgtacac cacctccaaa aataaaaaat ggaaaacaca cctttagtga agtagaagta 540
tttgagtatc ttgatgcagt aacttatagt tgtgatcctg cacctggacc agatccattt 600
tcacttattg gagagagcac gatttattgt ggtgacaatt cagtgtggag tcgtgctgct 660
ccagagtgta aagtggtcaa atgtcgattt ccagtagtcg aaaatggaaa acagatatca 720
ggatttggaa aaaaatttta ctacaaagca acagttatgt ttgaatgcga taagggtttt 780
tacctcgatg gcagcgacac aattgtctgt gacagtaaca gtacttggga tcccccagtt 840
ccaaagtgtc ttaaagtgtc gacttcttcc actacaaaat ctccagcgtc cagtgcctca 900
ggtcctaggc ctacttacaa gcctccagtc tcaaattatc caggatatcc taaacctgag 960
gaaggaatac ttgacagttt ggatgtttgg gtcattgctg tgattgttat tgccatagtt 1020
gttggagttg cagtaatttg tgttgtcccg tacagatatc ttcaaaggag gaagaagaaa 1080
ggcacatacc taactgatga gacccacaga gaagtaaaat ttacttctct ctga 1134

<210> SEQ ID NO 21
<211> LENGTH: 128
<212> TYPE: PRT
<213> ORGANISM: Homo sapiens

<400> SEQUENCE: 21

Met Gly Ile Gln Gly Gly Ser Val Leu Phe Gly Leu Leu Leu Val Leu
1 5 10 15

Ala Val Phe Cys His Ser Gly His Ser Leu Gln Cys Tyr Asn Cys Pro
20 25 30

Asn Pro Thr Ala Asp Cys Lys Thr Ala Val Asn Cys Ser Ser Asp Phe
35 40 45

Asp Ala Cys Leu Ile Thr Lys Ala Gly Leu Gln Val Tyr Asn Lys Cys
50 55 60

Trp Lys Phe Glu His Cys Asn Phe Asn Asp Val Thr Thr Arg Leu Arg
65 70 75 80

Glu Asn Glu Leu Thr Tyr Tyr Cys Cys Lys Lys Asp Leu Cys Asn Phe
85 90 95

Asn Glu Gln Leu Glu Asn Gly Gly Thr Ser Leu Ser Glu Lys Thr Val
100 105 110

Leu Leu Leu Val Thr Pro Phe Leu Ala Ala Ala Trp Ser Leu His Pro

```
        115                 120                 125


<210> SEQ ID NO 22
<211> LENGTH: 387
<212> TYPE: DNA
<213> ORGANISM: Homo sapiens

<400> SEQUENCE: 22

atgggaatcc aaggagggtc tgtcctgttc gggctgctgc tcgtcctggc tgtcttctgc      60

cattcaggtc atagcctgca gtgctacaac tgtcctaacc caactgctga ctgcaaaaca     120

gccgtcaatt gttcatctga ttttgatgcg tgtctcatta ccaaagctgg gttacaagtg     180

tataacaagt gttggaagtt tgagcattgc aatttcaacg acgtcacaac ccgcttgagg     240

gaaaatgagc taacgtacta ctgctgcaag aaggacctgt gtaactttaa cgaacagctt     300

gaaaatggtg ggacatcctt atcagagaaa acagttcttc tgctggtgac tccatttctg     360

gcagcagcct ggagccttca tccctaa                                         387


<210> SEQ ID NO 23
<211> LENGTH: 2039
<212> TYPE: PRT
<213> ORGANISM: Homo sapiens

<400> SEQUENCE: 23

Met Gly Ala Ser Ser Pro Arg Ser Pro Glu Pro Val Gly Pro Pro Ala
1               5                   10                  15

Pro Gly Leu Pro Phe Cys Cys Gly Gly Ser Leu Leu Ala Val Val Val
            20                  25                  30

Leu Leu Ala Leu Pro Val Ala Trp Gly Gln Cys Asn Ala Pro Glu Trp
        35                  40                  45

Leu Pro Phe Ala Arg Pro Thr Asn Leu Thr Asp Glu Phe Glu Phe Pro
    50                  55                  60

Ile Gly Thr Tyr Leu Asn Tyr Glu Cys Arg Pro Gly Tyr Ser Gly Arg
65                  70                  75                  80

Pro Phe Ser Ile Ile Cys Leu Lys Asn Ser Val Trp Thr Gly Ala Lys
                85                  90                  95

Asp Arg Cys Arg Arg Lys Ser Cys Arg Asn Pro Pro Asp Pro Val Asn
            100                 105                 110

Gly Met Val His Val Ile Lys Gly Ile Gln Phe Gly Ser Gln Ile Lys
        115                 120                 125

Tyr Ser Cys Thr Lys Gly Tyr Arg Leu Ile Gly Ser Ser Ser Ala Thr
    130                 135                 140

Cys Ile Ile Ser Gly Asp Thr Val Ile Trp Asp Asn Glu Thr Pro Ile
145                 150                 155                 160

Cys Asp Arg Ile Pro Cys Gly Leu Pro Pro Thr Ile Thr Asn Gly Asp
                165                 170                 175

Phe Ile Ser Thr Asn Arg Glu Asn Phe His Tyr Gly Ser Val Val Thr
            180                 185                 190

Tyr Arg Cys Asn Pro Gly Ser Gly Gly Arg Lys Val Phe Glu Leu Val
        195                 200                 205

Gly Glu Pro Ser Ile Tyr Cys Thr Ser Asn Asp Asp Gln Val Gly Ile
    210                 215                 220

Trp Ser Gly Pro Ala Pro Gln Cys Ile Ile Pro Asn Lys Cys Thr Pro
225                 230                 235                 240

Pro Asn Val Glu Asn Gly Ile Leu Val Ser Asp Asn Arg Ser Leu Phe
                245                 250                 255
```

-continued

```
Ser Leu Asn Glu Val Val Glu Phe Arg Cys Gln Pro Gly Phe Val Met
            260                 265                 270

Lys Gly Pro Arg Arg Val Lys Cys Gln Ala Leu Asn Lys Trp Glu Pro
        275                 280                 285

Glu Leu Pro Ser Cys Ser Arg Val Cys Gln Pro Pro Pro Asp Val Leu
    290                 295                 300

His Ala Glu Arg Thr Gln Arg Asp Lys Asp Asn Phe Ser Pro Gly Gln
305                 310                 315                 320

Glu Val Phe Tyr Ser Cys Glu Pro Gly Tyr Asp Leu Arg Gly Ala Ala
                325                 330                 335

Ser Met Arg Cys Thr Pro Gln Gly Asp Trp Ser Pro Ala Ala Pro Thr
            340                 345                 350

Cys Glu Val Lys Ser Cys Asp Asp Phe Met Gly Gln Leu Leu Asn Gly
        355                 360                 365

Arg Val Leu Phe Pro Val Asn Leu Gln Leu Gly Ala Lys Val Asp Phe
    370                 375                 380

Val Cys Asp Glu Gly Phe Gln Leu Lys Gly Ser Ser Ala Ser Tyr Cys
385                 390                 395                 400

Val Leu Ala Gly Met Glu Ser Leu Trp Asn Ser Ser Val Pro Val Cys
                405                 410                 415

Glu Gln Ile Phe Cys Pro Ser Pro Pro Val Ile Pro Asn Gly Arg His
            420                 425                 430

Thr Gly Lys Pro Leu Glu Val Phe Pro Phe Gly Lys Ala Val Asn Tyr
        435                 440                 445

Thr Cys Asp Pro His Pro Asp Arg Gly Thr Ser Phe Asp Leu Ile Gly
    450                 455                 460

Glu Ser Thr Ile Arg Cys Thr Ser Asp Pro Gln Gly Asn Gly Val Trp
465                 470                 475                 480

Ser Ser Pro Ala Pro Arg Cys Gly Ile Leu Gly His Cys Gln Ala Pro
                485                 490                 495

Asp His Phe Leu Phe Ala Lys Leu Lys Thr Gln Thr Asn Ala Ser Asp
            500                 505                 510

Phe Pro Ile Gly Thr Ser Leu Lys Tyr Glu Cys Arg Pro Glu Tyr Tyr
        515                 520                 525

Gly Arg Pro Phe Ser Ile Thr Cys Leu Asp Asn Leu Val Trp Ser Ser
    530                 535                 540

Pro Lys Asp Val Cys Lys Arg Lys Ser Cys Lys Thr Pro Pro Asp Pro
545                 550                 555                 560

Val Asn Gly Met Val His Val Ile Thr Asp Ile Gln Val Gly Ser Arg
                565                 570                 575

Ile Asn Tyr Ser Cys Thr Thr Gly His Arg Leu Ile Gly His Ser Ser
            580                 585                 590

Ala Glu Cys Ile Leu Ser Gly Asn Ala Ala His Trp Ser Thr Lys Pro
        595                 600                 605

Pro Ile Cys Gln Arg Ile Pro Cys Gly Leu Pro Pro Thr Ile Ala Asn
    610                 615                 620

Gly Asp Phe Ile Ser Thr Asn Arg Glu Asn Phe His Tyr Gly Ser Val
625                 630                 635                 640

Val Thr Tyr Arg Cys Asn Pro Gly Ser Gly Gly Arg Lys Val Phe Glu
                645                 650                 655

Leu Val Gly Glu Pro Ser Ile Tyr Cys Thr Ser Asn Asp Asp Gln Val
            660                 665                 670
```

-continued

```
Gly Ile Trp Ser Gly Pro Ala Pro Gln Cys Ile Ile Pro Asn Lys Cys
        675                 680                 685

Thr Pro Pro Asn Val Glu Asn Gly Ile Leu Val Ser Asp Asn Arg Ser
    690                 695                 700

Leu Phe Ser Leu Asn Glu Val Val Glu Phe Arg Cys Gln Pro Gly Phe
705                 710                 715                 720

Val Met Lys Gly Pro Arg Arg Val Lys Cys Gln Ala Leu Asn Lys Trp
                725                 730                 735

Glu Pro Glu Leu Pro Ser Cys Ser Arg Val Cys Gln Pro Pro Pro Asp
            740                 745                 750

Val Leu His Ala Glu Arg Thr Gln Arg Asp Lys Asp Asn Phe Ser Pro
        755                 760                 765

Gly Gln Glu Val Phe Tyr Ser Cys Glu Pro Gly Tyr Asp Leu Arg Gly
    770                 775                 780

Ala Ala Ser Met Arg Cys Thr Pro Gln Gly Asp Trp Ser Pro Ala Ala
785                 790                 795                 800

Pro Thr Cys Glu Val Lys Ser Cys Asp Asp Phe Met Gly Gln Leu Leu
                805                 810                 815

Asn Gly Arg Val Leu Phe Pro Val Asn Leu Gln Leu Gly Ala Lys Val
            820                 825                 830

Asp Phe Val Cys Asp Glu Gly Phe Gln Leu Lys Gly Ser Ser Ala Ser
        835                 840                 845

Tyr Cys Val Leu Ala Gly Met Glu Ser Leu Trp Asn Ser Ser Val Pro
    850                 855                 860

Val Cys Glu Gln Ile Phe Cys Pro Ser Pro Pro Val Ile Pro Asn Gly
865                 870                 875                 880

Arg His Thr Gly Lys Pro Leu Glu Val Phe Pro Phe Gly Lys Ala Val
                885                 890                 895

Asn Tyr Thr Cys Asp Pro His Pro Asp Arg Gly Thr Ser Phe Asp Leu
            900                 905                 910

Ile Gly Glu Ser Thr Ile Arg Cys Thr Ser Asp Pro Gln Gly Asn Gly
        915                 920                 925

Val Trp Ser Ser Pro Ala Pro Arg Cys Gly Ile Leu Gly His Cys Gln
    930                 935                 940

Ala Pro Asp His Phe Leu Phe Ala Lys Leu Lys Thr Gln Thr Asn Ala
945                 950                 955                 960

Ser Asp Phe Pro Ile Gly Thr Ser Leu Lys Tyr Glu Cys Arg Pro Glu
                965                 970                 975

Tyr Tyr Gly Arg Pro Phe Ser Ile Thr Cys Leu Asp Asn Leu Val Trp
            980                 985                 990

Ser Ser Pro Lys Asp Val Cys Lys  Arg Lys Ser Cys Lys  Thr Pro Pro
        995                 1000                1005

Asp Pro  Val Asn Gly Met Val  His Val Ile Thr Asp  Ile Gln Val
    1010                 1015                 1020

Gly Ser  Arg Ile Asn Tyr Ser  Cys Thr Thr Gly His  Arg Leu Ile
    1025                 1030                 1035

Gly His  Ser Ser Ala Glu Cys  Ile Leu Ser Gly Asn  Thr Ala His
    1040                 1045                 1050

Trp Ser  Thr Lys Pro Pro Ile  Cys Gln Arg Ile Pro  Cys Gly Leu
    1055                 1060                 1065

Pro Pro  Thr Ile Ala Asn Gly  Asp Phe Ile Ser Thr  Asn Arg Glu
    1070                 1075                 1080

Asn Phe  His Tyr Gly Ser Val  Val Thr Tyr Arg Cys  Asn Leu Gly
```

```
    1085                1090                1095

Ser Arg  Gly Arg Lys Val Phe  Glu Leu Val Gly Glu  Pro Ser Ile
    1100                1105                1110

Tyr Cys  Thr Ser Asn Asp Asp  Gln Val Gly Ile Trp  Ser Gly Pro
    1115                1120                1125

Ala Pro  Gln Cys Ile Ile Pro  Asn Lys Cys Thr Pro  Pro Asn Val
    1130                1135                1140

Glu Asn  Gly Ile Leu Val Ser  Asp Asn Arg Ser Leu  Phe Ser Leu
    1145                1150                1155

Asn Glu  Val Val Glu Phe Arg  Cys Gln Pro Gly Phe  Val Met Lys
    1160                1165                1170

Gly Pro  Arg Arg Val Lys Cys  Gln Ala Leu Asn Lys  Trp Glu Pro
    1175                1180                1185

Glu Leu  Pro Ser Cys Ser Arg  Val Cys Gln Pro Pro  Pro Glu Ile
    1190                1195                1200

Leu His  Gly Glu His Thr Pro  Ser His Gln Asp Asn  Phe Ser Pro
    1205                1210                1215

Gly Gln  Glu Val Phe Tyr Ser  Cys Glu Pro Gly Tyr  Asp Leu Arg
    1220                1225                1230

Gly Ala  Ala Ser Leu His Cys  Thr Pro Gln Gly Asp  Trp Ser Pro
    1235                1240                1245

Glu Ala  Pro Arg Cys Ala Val  Lys Ser Cys Asp Asp  Phe Leu Gly
    1250                1255                1260

Gln Leu  Pro His Gly Arg Val  Leu Phe Pro Leu Asn  Leu Gln Leu
    1265                1270                1275

Gly Ala  Lys Val Ser Phe Val  Cys Asp Glu Gly Phe  Arg Leu Lys
    1280                1285                1290

Gly Ser  Ser Val Ser His Cys  Val Leu Val Gly Met  Arg Ser Leu
    1295                1300                1305

Trp Asn  Asn Ser Val Pro Val  Cys Glu His Ile Phe  Cys Pro Asn
    1310                1315                1320

Pro Pro  Ala Ile Leu Asn Gly  Arg His Thr Gly Thr  Pro Ser Gly
    1325                1330                1335

Asp Ile  Pro Tyr Gly Lys Glu  Ile Ser Tyr Thr Cys  Asp Pro His
    1340                1345                1350

Pro Asp  Arg Gly Met Thr Phe  Asn Leu Ile Gly Glu  Ser Thr Ile
    1355                1360                1365

Arg Cys  Thr Ser Asp Pro His  Gly Asn Gly Val Trp  Ser Ser Pro
    1370                1375                1380

Ala Pro  Arg Cys Glu Leu Ser  Val Arg Ala Gly His  Cys Lys Thr
    1385                1390                1395

Pro Glu  Gln Phe Pro Phe Ala  Ser Pro Thr Ile Pro  Ile Asn Asp
    1400                1405                1410

Phe Glu  Phe Pro Val Gly Thr  Ser Leu Asn Tyr Glu  Cys Arg Pro
    1415                1420                1425

Gly Tyr  Phe Gly Lys Met Phe  Ser Ile Ser Cys Leu  Glu Asn Leu
    1430                1435                1440

Val Trp  Ser Ser Val Glu Asp  Asn Cys Arg Arg Lys  Ser Cys Gly
    1445                1450                1455

Pro Pro  Pro Glu Pro Phe Asn  Gly Met Val His Ile  Asn Thr Asp
    1460                1465                1470

Thr Gln  Phe Gly Ser Thr Val  Asn Tyr Ser Cys Asn  Glu Gly Phe
    1475                1480                1485
```

```
Arg Leu Ile Gly Ser Pro Ser Thr Thr Cys Leu Val Ser Gly Asn
    1490                1495                1500

Asn Val Thr Trp Asp Lys Lys Ala Pro Ile Cys Glu Ile Ile Ser
    1505                1510                1515

Cys Glu Pro Pro Pro Thr Ile Ser Asn Gly Asp Phe Tyr Ser Asn
    1520                1525                1530

Asn Arg Thr Ser Phe His Asn Gly Thr Val Val Thr Tyr Gln Cys
    1535                1540                1545

His Thr Gly Pro Asp Gly Glu Gln Leu Phe Glu Leu Val Gly Glu
    1550                1555                1560

Arg Ser Ile Tyr Cys Thr Ser Lys Asp Asp Gln Val Gly Val Trp
    1565                1570                1575

Ser Ser Pro Pro Pro Arg Cys Ile Ser Thr Asn Lys Cys Thr Ala
    1580                1585                1590

Pro Glu Val Glu Asn Ala Ile Arg Val Pro Gly Asn Arg Ser Phe
    1595                1600                1605

Phe Ser Leu Thr Glu Ile Ile Arg Phe Arg Cys Gln Pro Gly Phe
    1610                1615                1620

Val Met Val Gly Ser His Thr Val Gln Cys Gln Thr Asn Gly Arg
    1625                1630                1635

Trp Gly Pro Lys Leu Pro His Cys Ser Arg Val Cys Gln Pro Pro
    1640                1645                1650

Pro Glu Ile Leu His Gly Glu His Thr Leu Ser His Gln Asp Asn
    1655                1660                1665

Phe Ser Pro Gly Gln Glu Val Phe Tyr Ser Cys Glu Pro Ser Tyr
    1670                1675                1680

Asp Leu Arg Gly Ala Ala Ser Leu His Cys Thr Pro Gln Gly Asp
    1685                1690                1695

Trp Ser Pro Glu Ala Pro Arg Cys Thr Val Lys Ser Cys Asp Asp
    1700                1705                1710

Phe Leu Gly Gln Leu Pro His Gly Arg Val Leu Leu Pro Leu Asn
    1715                1720                1725

Leu Gln Leu Gly Ala Lys Val Ser Phe Val Cys Asp Glu Gly Phe
    1730                1735                1740

Arg Leu Lys Gly Arg Ser Ala Ser His Cys Val Leu Ala Gly Met
    1745                1750                1755

Lys Ala Leu Trp Asn Ser Ser Val Pro Val Cys Glu Gln Ile Phe
    1760                1765                1770

Cys Pro Asn Pro Pro Ala Ile Leu Asn Gly Arg His Thr Gly Thr
    1775                1780                1785

Pro Phe Gly Asp Ile Pro Tyr Gly Lys Glu Ile Ser Tyr Ala Cys
    1790                1795                1800

Asp Thr His Pro Asp Arg Gly Met Thr Phe Asn Leu Ile Gly Glu
    1805                1810                1815

Ser Ser Ile Arg Cys Thr Ser Asp Pro Gln Gly Asn Gly Val Trp
    1820                1825                1830

Ser Ser Pro Ala Pro Arg Cys Glu Leu Ser Val Pro Ala Ala Cys
    1835                1840                1845

Pro His Pro Pro Lys Ile Gln Asn Gly His Tyr Ile Gly Gly His
    1850                1855                1860

Val Ser Leu Tyr Leu Pro Gly Met Thr Ile Ser Tyr Thr Cys Asp
    1865                1870                1875
```

-continued

```
Pro Gly  Tyr Leu Leu Val Gly  Lys Gly Phe Ile Phe  Cys Thr Asp
    1880                 1885                 1890

Gln Gly  Ile Trp Ser Gln Leu  Asp His Tyr Cys Lys  Glu Val Asn
    1895                 1900                 1905

Cys Ser  Phe Pro Leu Phe Met  Asn Gly Ile Ser Lys  Glu Leu Glu
    1910                 1915                 1920

Met Lys  Lys Val Tyr His Tyr  Gly Asp Tyr Val Thr  Leu Lys Cys
    1925                 1930                 1935

Glu Asp  Gly Tyr Thr Leu Glu  Gly Ser Pro Trp Ser  Gln Cys Gln
    1940                 1945                 1950

Ala Asp  Asp Arg Trp Asp Pro  Pro Leu Ala Lys Cys  Thr Ser Arg
    1955                 1960                 1965

Ala His  Asp Ala Leu Ile Val  Gly Thr Leu Ser Gly  Thr Ile Phe
    1970                 1975                 1980

Phe Ile  Leu Leu Ile Ile Phe  Leu Ser Trp Ile Ile  Leu Lys His
    1985                 1990                 1995

Arg Lys  Gly Asn Asn Ala His  Glu Asn Pro Lys Glu  Val Ala Ile
    2000                 2005                 2010

His Leu  His Ser Gln Gly Gly  Ser Ser Val His Pro  Arg Thr Leu
    2015                 2020                 2025

Gln Thr  Asn Glu Glu Asn Ser  Arg Val Leu Pro
    2030                 2035
```

<210> SEQ ID NO 24
<211> LENGTH: 6120
<212> TYPE: DNA
<213> ORGANISM: Homo sapiens

<400> SEQUENCE: 24

```
atgggggcct cttctccaag aagcccggag cctgtcgggc cgccggcgcc cggtctcccc     60

ttctgctgcg gaggatccct gctggcggtt gtggtgctgc ttgcgctgcc ggtggcctgg    120

ggtcaatgca atgccccaga atggcttcca tttgccaggc ctaccaacct aactgatgaa    180

tttgagtttc ccattgggac atatctgaac tatgaatgcc gccctggtta ttccggaaga    240

ccgttttcta tcatctgcct aaaaaactca gtctggactg gtgctaagga caggtgcaga    300

cgtaaatcat gtcgtaatcc tccagatcct gtgaatggca tggtgcatgt gatcaaaggc    360

atccagttcg gatcccaaat taaatattct tgtactaaag gataccgact cattggttcc    420

tcgtctgcca catgcatcat ctcaggtgat actgtcattt gggataatga aacacctatt    480

tgtgacagaa ttccttgtgg gctacccccc accatcacca atggagattt cattagcacc    540

aacagagaga attttcacta tggatcagtg gtgacctacc gctgcaatcc tggaagcgga    600

gggagaaagg tgtttgagct tgtgggtgag ccctccatat actgcaccag caatgacgat    660

caagtgggca tctggagcgg ccccgcccct cagtgcatta tacctaacaa atgcacgcct    720

ccaaatgtgg aaaatggaat attggtatct gacaacagaa gcttattttc cttaaatgaa    780

gttgtggagt ttaggtgtca gcctggcttt gtcatgaaag gaccccgccg tgtgaagtgc    840

caggccctga acaaatggga gccggagcta ccaagctgct ccagggtatg tcagccacct    900

ccagatgtcc tgcatgctga gcgtacccaa agggacaagg acaacttttc acctgggcag    960

gaagtgttct acagctgtga gcccggctac gacctcagag ggctgcgtc tatgcgctgc   1020

acaccccagg gagactggag ccctgcagcc cccacatgtg aagtgaaatc ctgtgatgac   1080

ttcatgggcc aacttcttaa tggccgtgtg ctatttccag taaatctcca gcttggagca   1140
```

-continued

```
aaagtggatt ttgtttgtga tgaaggattt caattaaaag gcagctctgc tagttactgt   1200
gtcttggctg gaatggaaag cctttggaat agcagtgttc cagtgtgtga acaaatcttt   1260
tgtccaagtc ctccagttat tcctaatggg agacacacag gaaaacctct ggaagtcttt   1320
ccctttggaa aagcagtaaa ttacacatgc gacccccacc cagacagagg gacgagcttc   1380
gacctcattg gagagagcac catccgctgc acaagtgacc ctcaagggaa tggggtttgg   1440
agcagccctg cccctcgctg tggaattctg ggtcactgtc aagccccaga tcattttctg   1500
tttgccaagt tgaaaaccca aaccaatgca tctgactttc ccattgggac atctttaaag   1560
tacgaatgcc gtcctgagta ctacgggagg ccattctcta tcacatgtct agataacctg   1620
gtctggtcaa gtcccaaaga tgtctgtaaa cgtaaatcat gtaaaactcc tccagatcca   1680
gtgaatggca tggtgcatgt gatcacagac atccaggttg gatccagaat caactattct   1740
tgtactacag ggcaccgact cattggtcac tcatctgctg aatgtatcct ctcgggcaat   1800
gctgcccatt ggagcacgaa gccgccaatt tgtcaacgaa ttccttgtgg gctacccccc   1860
accatcgcca atggagattt cattagcacc aacagagaga attttcacta tggatcagtg   1920
gtgacctacc gctgcaatcc tggaagcgga gggagaaagg tgtttgagct tgtgggtgag   1980
ccctccatat actgcaccag caatgacgat caagtgggca tctggagcgg cccggcccct   2040
cagtgcatta yacctaacaa atgcacgcct ccaaatgtgg aaaatggaat attggtatct   2100
gacaacagaa gcttattttc cttaaatgaa gttgtggagt ttaggtgtca gcctggcttt   2160
gtcatgaaag gaccccgccg tgtgaagtgc caggccctga acaaatggga gccggagcta   2220
ccaagctgct ccagggtatg tcagccacct ccagatgtcc tgcatgctga gcgtacccaa   2280
agggacaagg acaacttttc acccgggcag gaagtgttct acagctgtga gcccggctay   2340
gacctcagag ggctgcgtc tatgcgctgc acaccccagg gagactggag ccctgcagcc   2400
cccacatgtg aagtgaaatc ctgtgatgac ttcatgggcc aacttcttaa tggccgtgtg   2460
ctatttccag taaatctcca gcttggagca aaagtggatt ttgtttgtga tgaaggattt   2520
caattaaaag gcagctctgc tagttattgt gtcttggctg gaatggaaag cctttggaat   2580
agcagtgttc cagtgtgtga acaaatcttt tgtccaagtc ctccagttat tcctaatggg   2640
agacacacag gaaaacctct ggaagtcttt ccctttggaa aagcagtaaa ttacacatgc   2700
gacccccacc cagacagagg gacgagcttc gacctcattg gagagagcac catccgctgc   2760
acaagtgacc ctcaagggaa tggggtttgg agcagccctg cccctcgctg tggaattctg   2820
ggtcactgtc aagccccaga tcattttctg tttgccaagt tgaaaaccca aaccaatgca   2880
tctgactttc ccattgggac atctttaaag tacgaatgcc gtcctgagta ctacgggagg   2940
ccattctcta tcacatgtct agataacctg gtctggtcaa gtcccaaaga tgtctgtaaa   3000
cgtaaatcat gtaaaactcc tccagatcca gtgaatggca tggtgcatgt gatcacagac   3060
atccakgttg gatccagaat caactattct tgtactacag ggcaccgact cattggtcac   3120
tcatctgctg aatgtatcct ctcaggcaat actgcccatt ggagcacgaa gccgccaatt   3180
tgtcaacgaa ttccttgtgg gctacccccca accatcgcca atggagattt cattagcacc   3240
aacagagaga attttcacta tggatcagtg gtgacctacc gctgcaatct tggaagcaga   3300
gggagaaagg tgtttgagct tgtgggtgag ccctccatat actgcaccag caatgacgat   3360
caagtgggca tctggagcgg ccccgcccct cagtgcatta tacctaacaa atgcacgcct   3420
ccaaatgtgg aaaatggaat attggtatct gacaacagaa gcttattttc cttaaatgaa   3480
gttgtggagt ttaggtgtca gcctggcttt gtcatgaaag gaccccgccg tgtgaagtgc   3540
```

caggccctga acaaatggga gccagagtta ccaagctgct ccagggtgtg tcagccgcct 3600
ccagaaatcc tgcatggtga gcatacccca agccatcagg acaacttttc acctgggcag 3660
gaagtgttct acagctgtga gcctggctat gacctcagag ggctgcgtc tctgcactgc 3720
acaccccagg gagactggag ccctgaagcc ccgagatgtg cagtgaaatc ctgtgatgac 3780
ttcttgggtc aactccctca tggccgtgtg ctatttccac ttaatctcca gcttggggca 3840
aaggtgtcct ttgtctgtga tgaagggttt cgcttaaagg gcagttccgt tagtcattgt 3900
gtcttggttg gaatgagaag cctttggaat aacagtgttc ctgtgtgtga acatatcttt 3960
tgtccaaatc ctccagctat ccttaatggg agacacacag gaactccctc tggagatatt 4020
ccctatggaa aagaaatatc ttacacatgt gacccccacc cagacagagg gatgaccttc 4080
aacctcattg ggagagcac catccgctgc acaagtgacc ctcatgggaa tggggtttgg 4140
agcagccctg cccctcgctg tgaactttct gttcgtgctg gtcactgtaa aaccccagag 4200
cagtttccat ttgccagtcc tacgatccca attaatgact ttgagtttcc agtcgggaca 4260
tctttgaatt atgaatgccg tcctgggtat tttgggaaaa tgttctctat ctcctgccta 4320
gaaaacttgg tctggtcaag tgttgaagac aactgtagac gaaaatcatg tggacctcca 4380
ccagaaccct tcaatggaat ggtgcatata aacacagata cacagtttgg atcaacagtt 4440
aattattctt gtaatgaagg gtttcgactc attggttccc catctactac ttgtctcgtc 4500
tcaggcaata atgtcacatg ggataagaag gcacctattt gtgagatcat atcttgtgag 4560
ccacctccaa ccatatccaa tggagacttc tacagcaaca atagaacatc ttttcacaat 4620
ggaacggtgg taacttacca gtgccacact ggaccagatg gagaacagct gtttgagctt 4680
gtgggagaac ggtcaatata ttgcaccagc aaagatgatc aagttggtgt ttggagcagc 4740
cctccccctc ggtgtatttc tactaataaa tgcacagctc cagaagttga aaatgcaatt 4800
agagtaccag gaaacaggag tttcttttcc ctcactgaga tcgtcagatt tagatgtcag 4860
cccgggtttg tcatggtagg gtcccacact gtgcagtgcc agaccaatgg cagatggggg 4920
cccaagctgc cacactgctc cagggtgtgt cagccgcctc cagaaatcct gcatggtgag 4980
cataccctaa gccatcagga caacttttca cctgggcagg aagtgttcta cagctgtgag 5040
cccagctatg acctcagagg ggctgcgtct ctgcactgca cgccccaggg agactggagc 5100
cctgaagccc ctagatgtac agtgaaatcc tgtgatgact tcctgggcca actccctcat 5160
ggccgtgtgc tacttccact taatctccag cttggggcaa aggtgtcctt tgtttgcgat 5220
gaagggttcc gattaaaagg caggtctgct agtcattgtg tcttggctgg aatgaaagcc 5280
ctttggaata gcagtgttcc agtgtgtgaa caaatctttt gtccaaatcc tccagctatc 5340
cttaatggga gacacacagg aactcccttt ggagatattc cctatggaaa agaaatatct 5400
tacgcatgcg acacccaccc agacagaggg atgaccttca acctcattgg ggagagctcc 5460
atccgctgca caagtgaccg tcaagggaat ggggtttgga gcagccctgc ccctcgctgt 5520
gaactttctg ttcctgctgc ctgcccagat ccacccaaga tccaaaacgg gcattacatt 5580
ggaggacacg tatctctata tcttcctggg atgacaatca gctacatttg tgaccccggc 5640
tacctgttag tgggaaaggg cttcattttc tgtacagacc agggaatctg gagccaattg 5700
gatcattatt gcaaagaagt aaattgtagc ttcccactgt ttatgaatgg aatctcgaag 5760
gagttagaaa tgaaaaaagt atatcactat ggagattatg tgactttgaa gtgtgaagat 5820
gggtatactc tggaaggcag tccctggagc cagtgccagg cggatgacag atgggaccct 5880

-continued

```
cctctggcca aatgtacctc tcgtgcacat gatgctctca tagttggcac tttatctggt   5940

acgatcttct ttattttact catcattttc ctctcttgga taattctaaa gcacagaaaa   6000

ggcaataatg cacatgaaaa ccctaaagaa gtggctatcc atttacattc tcaaggaggc   6060

agcagcgttc atccccgaac tctgcaaaca aatgaagaaa atagcagggt ccttccttga   6120


<210> SEQ ID NO 25
<211> LENGTH: 483
<212> TYPE: PRT
<213> ORGANISM: Mus musculus

<400> SEQUENCE: 25

Met Glu Val Ser Ser Arg Ser Ser Glu Pro Leu Asp Pro Val Trp Leu
1               5                   10                  15

Leu Val Ala Phe Gly Arg Gly Gly Val Lys Leu Glu Val Leu Leu Leu
            20                  25                  30

Phe Leu Leu Pro Phe Thr Leu Gly Glu Leu Arg Gly Gly Leu Gly Lys
        35                  40                  45

His Gly His Thr Val His Arg Glu Pro Ala Val Asn Arg Leu Cys Ala
    50                  55                  60

Asp Ser Lys Arg Trp Ser Gly Leu Pro Val Ser Ala Gln Arg Pro Phe
65                  70                  75                  80

Pro Met Gly His Cys Pro Ala Pro Ser Gln Leu Pro Ser Ala Lys Pro
                85                  90                  95

Ile Asn Leu Thr Asp Glu Ser Met Phe Pro Ile Gly Thr Tyr Leu Leu
            100                 105                 110

Tyr Glu Cys Leu Pro Gly Tyr Ile Lys Arg Gln Phe Ser Ile Thr Cys
        115                 120                 125

Lys Gln Asp Ser Thr Trp Thr Ser Ala Glu Asp Lys Cys Ile Arg Lys
    130                 135                 140

Gln Cys Lys Thr Pro Ser Asp Pro Glu Asn Gly Leu Val His Val His
145                 150                 155                 160

Thr Gly Ile Gln Phe Gly Ser Arg Ile Asn Tyr Thr Cys Asn Gln Gly
                165                 170                 175

Tyr Arg Leu Ile Gly Ser Ser Ser Ala Val Cys Val Ile Thr Asp Gln
            180                 185                 190

Ser Val Asp Trp Asp Thr Glu Ala Pro Ile Cys Glu Trp Ile Pro Cys
        195                 200                 205

Glu Ile Pro Pro Gly Ile Pro Asn Gly Asp Phe Phe Ser Ser Thr Arg
    210                 215                 220

Glu Asp Phe His Tyr Gly Met Val Val Thr Tyr Arg Cys Asn Thr Asp
225                 230                 235                 240

Ala Arg Gly Lys Ala Leu Phe Asn Leu Val Gly Glu Pro Ser Leu Tyr
                245                 250                 255

Cys Thr Ser Asn Asp Gly Glu Ile Gly Val Trp Ser Gly Pro Pro Pro
            260                 265                 270

Gln Cys Ile Glu Leu Asn Lys Cys Thr Pro Pro Pro Tyr Val Glu Asn
        275                 280                 285

Ala Val Met Leu Ser Glu Asn Arg Ser Leu Phe Ser Leu Arg Asp Ile
    290                 295                 300

Val Glu Phe Arg Cys His Pro Gly Phe Ile Met Lys Gly Ala Ser Ser
305                 310                 315                 320

Val His Cys Gln Ser Leu Asn Lys Trp Glu Pro Glu Leu Pro Ser Cys
                325                 330                 335
```

-continued

```
Phe Lys Gly Val Ile Cys Arg Leu Pro Gln Glu Met Ser Gly Phe Gln
            340                 345                 350

Lys Gly Leu Gly Met Lys Lys Glu Tyr Tyr Tyr Gly Glu Asn Val Thr
        355                 360                 365

Leu Glu Cys Glu Asp Gly Tyr Thr Leu Glu Gly Ser Ser Gln Ser Gln
    370                 375                 380

Cys Gln Ser Asp Gly Ser Trp Asn Pro Leu Leu Ala Lys Cys Val Ser
385                 390                 395                 400

Arg Ser Ile Ser Gly Leu Ile Val Gly Ile Phe Ile Gly Ile Ile Val
                405                 410                 415

Phe Ile Leu Val Ile Ile Val Phe Ile Trp Met Ile Leu Lys Tyr Lys
            420                 425                 430

Lys Arg Asn Thr Thr Asp Glu Lys Tyr Lys Glu Val Gly Ile His Leu
        435                 440                 445

Asn Tyr Lys Glu Asp Ser Cys Val Arg Leu Gln Ser Leu Leu Thr Ser
    450                 455                 460

Gln Glu Asn Ser Ser Thr Thr Ser Pro Ala Arg Asn Ser Leu Thr Gln
465                 470                 475                 480

Glu Val Ser


<210> SEQ ID NO 26
<211> LENGTH: 1323
<212> TYPE: DNA
<213> ORGANISM: Mus musculus

<400> SEQUENCE: 26

atggaggtct cttctcggag ttcagagcct ctggatccgg tgtggctcct tgtagccttc     60

ggccggggag gagtcaagct agaagttttg ctgctgttct tgctgccatt tactttgggt    120

cactgcccag ccccatcaca gcttccttct gccaaaccta taaatctaac tgatgaatcc    180

atgtttccca ttggaacata tttgttgtat gaatgtctcc caggatatat caagaggcag    240

ttctctatca cctgcaaaca agactcaacc tggacgagtg ctgaagataa gtgtatacga    300

aaacaatgta aaactccttc agatcctgag aatggcttgg tacatgtaca cacaggcatt    360

cagtttggat cccgtattaa ttatacttgt aatcaaggat accgcctcat tggttcctcc    420

tctgctgtat gtgtcatcac tgatcaaagt gttgattggg atactgaggc acctatttgt    480

gagtggattc cttgtgagat acccccaggc attcccaatg gagatttctt cagttcaacc    540

agagaagact ttcattatgg aatggtggtt acctaccgct gcaacactga tgcgagaggg    600

aaggcgctct ttaacctggt gggtgagccc tccttatact gtaccagcaa cgatggtgaa    660

attggagtct ggagcggccc tcctcctcag tgcattgaac tcaacaaatg tactcctcct    720

ccctatgttg aaaatgcagt catgctgtct gagaacagaa gcttgttttc cttaagggat    780

attgtggagt ttagatgtca ccctggcttt atcatgaaag gagccagcag tgtgcattgt    840

cagtccctaa acaaatggga gccagagtta ccaagctgct tcaagggagt gatatgtcgt    900

ctccctcagg agatgagtgg attccagaag gggttgggaa tgaaaaaaga atattattat    960

ggagagaatg taaccttgga atgtgaggat gggtatactc tagaaggcag ttctcaaagc   1020

cagtgccagt ctgatggcag ctggaatcct cttctggcca aatgtgtatc tcgctcaatc   1080

agtggtctaa ttgttggaat tttcattggg ataatcgtct ttattttagt catcattgtt   1140

ttcatttgga tgattctgaa gtataaaaaa cgcaatacca cagatgaaaa gtataaagaa   1200

gtgggtattc atttaaatta taaagaagac agctgtgtcc gccttcagtc tctgctcaca   1260
```

```
agtcaggaga acagcagtac cactagccca gcacggaatt cactcactca agaagtctcc   1320

taa                                                                 1323


<210> SEQ ID NO 27
<211> LENGTH: 18
<212> TYPE: DNA
<213> ORGANISM: Artificial Sequence
<220> FEATURE:
<223> OTHER INFORMATION: Synthetic polynucleotide

<400> SEQUENCE: 27

tctccagcat gtcataag                                                   18


<210> SEQ ID NO 28
<211> LENGTH: 16
<212> TYPE: DNA
<213> ORGANISM: Artificial Sequence
<220> FEATURE:
<223> OTHER INFORMATION: Synthetic polynucleotide

<400> SEQUENCE: 28

gtctgccctt tgcaag                                                     16


<210> SEQ ID NO 29
<211> LENGTH: 16
<212> TYPE: DNA
<213> ORGANISM: Artificial Sequence
<220> FEATURE:
<223> OTHER INFORMATION: Synthetic polynucleotide

<400> SEQUENCE: 29

caatgtcctg cctctg                                                     16


<210> SEQ ID NO 30
<211> LENGTH: 7
<212> TYPE: PRT
<213> ORGANISM: Homo sapiens

<400> SEQUENCE: 30

Val Ser Val Phe Pro Leu Glu
1               5


<210> SEQ ID NO 31
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 31

Ser Leu Tyr Tyr Tyr Ile Gln Gln Asp Thr Lys
1               5                   10
```

MODULATING THE ALTERNATIVE COMPLEMENT PATHWAY

CROSS-REFERENCES TO RELATED APPLICATIONS

This application is a continuation of U.S. application Ser. No. 13/120,125, filed Mar. 21, 2011, which in turn is a national stage of International Application No. PCT/US2009/057912, filed Sep. 22, 2009, which claims the benefit of U.S. Provisional Application No. 61/099,173, filed Sep. 22, 2008, the entire contents of which are incorporated herein by reference in their entireties and for all purposes.

STATEMENT OF RIGHTS TO INVENTIONS MADE UNDER FEDERALLY SPONSORED RESEARCH OR DEVELOPMENT

This invention was made with government support under grant numbers K08 DK064790, R01 AI031005 and R01 DK076690 awarded by the National Institutes of Health. The government has certain rights in the invention.

REFERENCE TO A "SEQUENCE LISTING," A TABLE, OR A COMPUTER PROGRAM LISTING APPENDIX SUBMITTED AS AN ASCII TEXT FILE

The Sequence Listing written in file 85665-927177$_{13}$ST25.TXT, created on Dec. 11, 2014, 98,595 bytes, machine format IBM-PC, MS-Windows operating system, is hereby incorporated by reference.

BACKGROUND OF THE INVENTION

The alternative pathway of complement is a phylogenetically ancient arm of the innate immune system that eliminates invasive pathogens and facilitates the removal of injured host cells. See J. M. Thurman et al., *J. Immunol.* (2006) 176:1305-1310. The alternative pathway is continually auto-activated in the fluid phase, forming C3b which can bind to nearby biologic surfaces. This spontaneously formed C3b then catalyzes further activation and amplification through the alternative complement pathway unless controlled by complement regulatory proteins (CRPs). The CRPs dissociate the alternative pathway C3 convertase (C3bBb) and/or serve as cofactors for the cleavage of C3 by factor I, forming iC3b. Thus, complement inhibition by CRPs on host cells is critical for protecting host cells from spontaneous alternative complement pathway-mediated injury. Expression of CRPs is a fundamental mechanism by which the alternative pathway distinguishes healthy cells from injured cells and invasive pathogens.

The endogenous membrane-bound proteins that control alternative pathway activation are decay-accelerating factor (DAF/CD55), membrane cofactor protein (MCP/CD46), and complement receptor 1 (CR1). Other endogenous proteins that control alternative pathway activation include Factor H, a circulating ~155 kD glycoprotein that regulates alternative pathway activation in the fluid phase as well as on tissue surfaces. See J. J. Alexander et al., *Mol. Immunol.* (2006) 44:123-132. Uncontrolled alternative pathway activation has been implicated in the pathogenesis of a diverse group of diseases, including age-related macular degeneration (AMD), atypical hemolytic uremic syndrome (aHUS), type II membranoproliferative glomerulonephritis (MPGN II), asthma, and renal ischemia/reperfusion (I/R) injury. See J. M. Thurman et al., *J. Immunol.* (2006) 176:1305-1310. Injury to host tissues by the alternative pathway indicates insufficient local control of the alternative pathway by the target tissue. Indeed, recent studies have demonstrated that mutations in CRPs are strong risk factors for aHUS (M. C. Pickering et al., *J. Exp. Med.* (2007) 204:1249-1256) and MPGN II (R. J. Smith et al., *J. Am. Soc. Nephrol.* (2007) 18:2447-2456), and functional polymorphisms in factor H, a circulating regulator of the alternative pathway, are associated with the development of AMD (R. J. Klein et al., *Science* (2005) 308:385-389; A. O. Edwards et al., *Science* (2005) 308:421-424; J. L. Haines et al., *Science* (2005) 308:419-421; G. S. Hageman et al., *Proc. Nat'l Acad. Sci. USA* (2005) 102:7227-7232).

Ischemic acute kidney injury (AKI) in rodents (J. M. Thurman et al., *J. Immunol.* (2003) 170:1517-1523; J. M. Thurman et al., *J. Am. Soc. Nephrol.* (2006) 17:707-715) and in humans (J. M. Thurman et al., *Kidney Int.* (2005) 67:524-530) is associated with activation of the alternative pathway on the basolateral surface of injured tubular cells. We have found that Complement receptor 1-related gene/protein y (Crry, a rodent analog of human MCP and CR1) is the only CRP expressed by proximal tubular epithelial cells in mice, and that ischemia/reperfusion causes reduced surface expression of this protein. See J. M. Thurman et al., *J. Clin. Invest.* (2006) 116:357-368. Mice with congenital deficiency of Crry (Crry+/−) are more sensitive than wild-type controls to ischemic acute renal failure (Id.), highlighting the importance of basolateral Crry for controlling the alternative pathway on this surface. It is not yet known whether polymorphisms or mutations in the CRPs may confer increased risk of developing AKI in humans. Nevertheless, uncontrolled activation of the alternative pathway in the setting of reduced surface Crry indicates that circulating factor H has a limited ability to protect the surface of hypoxic tubular epithelial cells.

Factor H circulates in high concentrations (>400-600 μg/ml) and is a potent inhibitor of the alternative complement pathway. See J. J. Alexander et al., *Mol. Immunol.* (2006) 44:123-132. Alternative pathway inhibition on cell surfaces by factor H, however, requires that it properly bind to that surface. Several regions within the factor H protein bind to anionic surfaces, such as membranes rich in heparin sulfate or sialic acid, as well as to C3b on the surface. See S. Meri et al., *Proc. Nat'l Acad. Sci. USA* (1990) 87:3982-3986; M. K. Pangburn et al., *J. Immunol.* (2000) 164:4742-4751. Activation of the alternative pathway on a particular surface is strongly influenced by the affinity of factor H for that surface. The polymorphisms and mutations associated with AMD and aHUS, respectively, most frequently involve the region of factor H required for binding anionic surfaces and not the complement regulatory region. See M. C. Pickering et al., *J. Exp. Med.* (2007) 204:1249-1256; A. P. et al., *J. Biol. Chem.* (2007) 282:10894-10900. Thus, certain tissues or cell types require factor H to regulate alternative pathway activation on their surface. Different binding regions of the factor H protein may be necessary for complement regulation on those tissues or cell types. In some cases, the binding of factor H to surfaces in particular tissues may be affected by other proteins. Identification of putative tissue-specific binding partners of factor H may provide potential mechanisms for modulating, i.e., stimulating or inhibiting, activity of the alternative complement pathway in different tissues.

The disclosures of all publications, patents, patent applications and published patent applications referred to herein are hereby incorporated herein by reference in their entirety and for all purposes.

BRIEF SUMMARY OF THE INVENTION

This application pertains to methods and compositions for modulating, e.g., stimulating or inhibiting, activity of the alternative complement pathway.

Provided herein are methods of modulating alternative complement activity in an individual, comprising administering to the individual a composition selected from the group consisting of (a) annexin A2 or a biologically-active fragment thereof; (b) a fusion protein comprising an anti-annexin A2 antibody or an antigen-binding fragment thereof fused to a complement inhibitor selected from the group consisting of DAF, factor H, MCP, CD59, CR1, and mouse Crry protein or a biologically-active fragment thereof; and (c) a biologically-active fragment of factor H lacking the complement regulatory domain in SCRs 1 to 4 of full-length factor H. In certain embodiments, the individual is a mammal. In certain embodiments, the mammal is a human, a mouse, or a rat. In certain embodiments, alternative complement activity is inhibited in an individual. In certain embodiments, alternative complement activity is stimulated in an individual.

In certain embodiments, alternative complement activity is inhibited in an individual and the individual is administered a composition selected from the group consisting of (a) annexin A2 or a biologically-active fragment thereof; and (b) a fusion protein comprising an anti-annexin A2 antibody or antigen-binding fragment thereof fused to a complement inhibitor selected from the group consisting of DAF, factor H, MCP, CD59, CR1, and mouse Crry protein or a biologically-active fragment thereof. In certain embodiments, the individual is administered a composition comprising annexin A2 or a biologically-active fragment thereof. In certain embodiments, the individual is administered a composition comprising annexin A2. In certain embodiments, the composition is administered orally or by injection. In certain embodiments, the injection is intravenous.

In certain embodiments, alternative complement activity is stimulated in an individual and the individual is administered a composition an annexin A2 or a biologically-active fragment thereof. In certain embodiments, the individual is administered a composition comprising annexin A2 or a biologically-active fragment thereof. In certain embodiments, the individual is administered a composition comprising annexin A2. In certain embodiments, the composition is administered orally or by injection. In certain embodiments, the injection is intravenous.

In certain embodiments, the individual is administered a composition comprising a fusion protein comprising an anti-annexin A2 antibody or antigen-binding fragment thereof fused to DAF or a biologically-active fragment thereof. In certain embodiments, the antigen-binding fragment thereof comprises an Fab, Fab', or $F(ab')_2$ fragment. In certain embodiments, the biologically-active fragment of DAF fused to an anti-annexin A2 antibody or antigen-binding fragment thereof comprises the mature human DAF protein (amino acids 35-353 of SEQ ID NO:17) without its GPI anchor. In certain embodiments, the biologically-active fragment of DAF fused to an anti-annexin A2 antibody or antigen-binding fragment thereof comprises short consensus repeat sequences 1 to 4 (SCRs 1 to 4) of full-length human DAF (amino acids 35 to 285 of SEQ ID NO:17). In certain embodiments, the composition is administered orally or by injection. In certain embodiments, the injection is intravenous.

In certain embodiments, the individual is administered a composition comprising a fusion protein comprising an anti-annexin A2 antibody or antigen-binding fragment thereof fused to factor H or a biologically-active fragment thereof. In certain embodiments, the antigen-binding fragment thereof comprises an Fab, Fab', or $F(ab')_2$ fragment. In certain embodiments, the biologically-active fragment of factor H fused to an anti-annexin A2 antibody or antigen-binding fragment thereof comprises SCRs 1 to 4 of full-length factor H (amino acids 21-266 of SEQ ID NO:3). In certain embodiments, the biologically-active fragment of factor H fused to an anti-annexin A2 antibody or antigen-binding fragment thereof comprises SCRs 1 to 8 of full-length factor H (amino acids 21-509 of SEQ ID NO:3). In certain embodiments, the biologically-active fragment of factor H fused to an anti-annexin A2 antibody or antigen-binding fragment thereof comprises SCRs 1 to 18 of full-length factor H (amino acids 21-1106 of SEQ ID NO:3). In certain embodiments, the composition is administered orally or by injection. In certain embodiments, the injection is intravenous.

In certain embodiments, the individual is administered a composition comprising a fusion protein comprising an anti-annexin A2 antibody or antigen-binding fragment thereof fused to MCP or a biologically-active fragment thereof. In certain embodiments, the antigen-binding fragment thereof comprises an Fab, Fab', or $F(ab')_2$ fragment. In certain embodiments, the biologically-active fragment of MCP fused to an anti-annexin A2 antibody or antigen-binding fragment thereof comprises the extracellular domain of human MCP (amino acids 35-343 of SEQ ID NO:19). In certain embodiments, the biologically-active fragment of MCP fused to an anti-annexin A2 antibody or antigen-binding fragment thereof comprises SCRs 1 to 4 of full-length human MCP (amino acids 35-285 of SEQ ID NO:19). In certain embodiments, the composition is administered orally or by injection. In certain embodiments, the injection is intravenous.

In certain embodiments, the individual is administered a composition comprising a fusion protein comprising an anti-annexin A2 antibody or antigen-binding fragment thereof fused to CD59 or a biologically-active fragment thereof. In certain embodiments, the antigen-binding fragment thereof comprises an Fab, Fab', or $F(ab')_2$ fragment. In certain embodiments, the biologically-active fragment of CD59 fused to an anti-annexin A2 antibody or antigen-binding fragment thereof comprises the extracellular domain of full-length human CD59 (amino acids 26-102 of SEQ ID NO:21) lacking its GPI anchor and/or the amino acid to which it is attached (i.e., Asn-102). In certain embodiments, the composition is administered orally or by injection. In certain embodiments, the injection is intravenous.

In certain embodiments, the individual is administered a composition comprising a fusion protein comprising an anti-annexin A2 antibody or antigen-binding fragment thereof fused to CR1 or a biologically-active fragment thereof. In certain embodiments, the antigen-binding fragment thereof comprises an Fab, Fab', or $F(ab')_2$ fragment. In certain embodiments, the biologically-active fragment of CR1 fused to an anti-annexin A2 antibody or antigen-binding fragment thereof comprises the complete extracellular domain of full-length human CR1 (SCRs 1 to 30) (amino acids 42-1971 of SEQ ID NO:23). In certain embodiments, the biologically-active fragment of CR1 fused to an anti-annexin A2 antibody or antigen-binding fragment thereof comprises SCRs 1 to 4 of full-length human CR1 (amino acids 42-295 of SEQ ID NO:23). In certain embodiments, the biologically-active fragment of CR1 fused to an anti-annexin A2 antibody or antigen-binding fragment thereof comprises SCRs 1 to 11 of full-length human CR1 (amino acids 42-745 of SEQ ID NO:23). In certain embodiments, the biologically-active fragment of CR1 fused to an anti-annexin A2 antibody or antigen-binding fragment thereof comprises SCRs 1 to 18 of full-length human CR1 (amino acids 42-1195 of SEQ ID NO:23). In certain embodiments, the composition is administered orally or by injection. In certain embodiments, the injection is intravenous.

In certain embodiments, the individual is administered a composition comprising a fusion protein comprising an anti-annexin A2 antibody or antigen-binding fragment thereof fused to mouse Crry protein or a biologically-active fragment thereof. In certain embodiments, the antigen-binding fragment thereof comprises an Fab, Fab', or $F(ab')_2$ fragment. In certain embodiments, the biologically-active fragment of mouse Crry protein fused to an anti-annexin A2 antibody or antigen-binding fragment thereof comprises the complete extracellular domain of full-length mouse Crry protein (amino acids 41-405 of SEQ ID NO:25). In certain embodiments, the biologically-active fragment of mouse Crry protein fused to an anti-annexin A2 antibody or antigen-binding fragment thereof comprises SCRs 1 to 5 of full-length mouse Crry protein (amino acids 83-400 of SEQ ID NO:25). In certain embodiments, the composition is administered orally or by injection. In certain embodiments, the injection is intravenous.

In certain embodiments, the alternative complement activity is associated with renal inflammation or a drusen-related disease. In certain embodiments, the renal inflammation is associated with ischemia/reperfusion injury, ischemic acute kidney injury, thrombotic thrombocytopenic purpura (TTP), hemolytic uremic syndrome ("HUS"), or atypical hemolytic uremic syndrome ("aHUS"). In certain embodiments, the drusen-related disease is selected from the group consisting of age-related macular degeneration, type II membranoproliferative glomerulonephritis ("MPGN II") and amyloidosis.

In certain embodiments, alternative complement activity is stimulated in an individual and the individual is administered a composition selected from the group consisting of a biologically-active fragment of factor H lacking the complement regulatory domain in SCRs 1 to 4 of full-length factor H. In certain embodiments, the biologically active fragment of factor H comprises SCRs 19 and 20.

Provided herein are compositions for modulating alternative complement activity in an individual. In certain embodiments, alternative complement activity is inhibited. In certain embodiments, alternative complement activity is stimulated.

In certain embodiments, the composition for modulating alternative complement activity comprises (a) annexin A2 or a biologically-active fragment thereof; (b) a fusion protein comprising an anti-annexin A2 antibody or an antigen-binding fragment thereof fused to a complement inhibitor selected from the group consisting of DAF, factor H, MCP, CD59, CR1, and mouse Crry protein or a biologically-active fragment thereof; or (c) a biologically-active fragment of factor H lacking the complement regulatory domain in SCRs 1 to 4 of full-length factor H; and a pharmaceutically acceptable carrier suitable for administration to an individual. In certain embodiments, alternative complement activity is inhibited. In certain embodiments, alternative complement activity is stimulated.

In certain embodiments, alternative complement activity is inhibited and the composition comprises annexin A2 or a biologically-active fragment thereof and a pharmaceutically acceptable carrier suitable for administration to an individual. In certain embodiments, alternative complement activity is inhibited and the composition comprises annexin A2 and a pharmaceutically acceptable carrier suitable for administration to an individual. In certain embodiments, the composition comprises an anti-annexin A2 antibody or an antigen-binding fragment thereof fused to a complement inhibitor selected from the group consisting of DAF, factor H, MCP, CD59, CR1, and mouse Crry protein or a biologically-active fragment thereof and a pharmaceutically acceptable carrier suitable for administration to an individual. In certain embodiments, the antigen-binding fragment of an anti-annexin A2 antibody comprises an Fab, Fab', or $F(ab')_2$ fragment.

In certain embodiments, alternative complement activity is stimulated and the composition comprises annexin A2 or a biologically-active fragment thereof and a pharmaceutically acceptable carrier suitable for administration to an individual. In certain embodiments, alternative complement activity is simulated and the composition comprises annexin A2 and a pharmaceutically acceptable carrier suitable for administration to an individual.

In certain embodiments, the biologically-active fragment of DAF comprises the mature human DAF protein (amino acids 35-353 of SEQ ID NO:17) without its GPI anchor or short consensus repeat sequences 1 to 4 (SCRs 1 to 4) of full-length human DAF (amino acids 35 to 285 of SEQ ID NO:17). In certain embodiments, the biologically-active fragment of factor H comprises SCRs 1 to 4 of full-length factor H (amino acids 21-266 of SEQ ID NO:3), SCRs 1 to 8 of full-length factor H (amino acids 21-509 of SEQ ID NO:3), or SCRs 1 to 18 of full-length factor H (amino acids 21-1106 of SEQ ID NO:3). In certain embodiments, the biologically-active fragment of MCP comprises the extracellular domain of human MCP (amino acids 35-343 of SEQ ID NO:19) or SCRs 1 to 4 of full-length human MCP (amino acids 35-285 of SEQ ID NO:19). In certain embodiments, the biologically-active fragment of CD59 comprises the extracellular domain of full-length human CD59 (amino acids 26-102 of SEQ ID NO:21) lacking its GPI anchor and/or the amino acid to which it is attached (i.e., Asn-102). In certain embodiments, the biologically-active fragment of CR1 comprises the complete extracellular domain of full-length human CR1 (SCRs 1 to 30)(amino acids 42-1971 of SEQ ID NO:23), SCRs 1 to 4 of full-length human CR1 (amino acids 42-295 of SEQ ID NO:23), SCRs 1 to 11 of full-length human CR1 (amino acids 42-745 of SEQ ID NO:23), or SCRs 1 to 18 of full-length human CR1 (amino acids 42-1195 of SEQ ID NO:23). In certain embodiments, the biologically-active fragment of mouse Crry protein comprises the complete extracellular domain of full-length mouse Crry protein (amino acids 41-405 of SEQ ID NO:25) or SCRs 1 to 5 of full-length mouse Crry protein (amino acids 83-400 of SEQ ID NO:25).

In certain embodiments, alternative complement activity is stimulated and the composition comprises a biologically-active fragment of factor H lacking the complement regulatory domain in SCRs 1 to 4 of full-length factor H and a pharmaceutically acceptable carrier suitable for administration to an individual. In certain embodiments, the biologically-active fragment of factor H comprises SCRs 19 and 20 (amino acids 1109-1232 of SEQ ID NO:3).

BRIEF DESCRIPTION OF THE DRAWINGS

(FIG. 1A) After eight hours of reperfusion the plasma C3a levels in mice treated with rH19-20 were higher than those that received vehicle. (FIG. 1B) After twenty-four hours of reperfusion the plasma C3a levels in mice treated with rH19-20 were higher than those that received vehicle, although the difference was no longer significant. FIG. 1C) Morphologic injury in mice that received vehicle demonstrated tubular injury in the outer medulla, but the cortex (inset) was primarily spared. (FIG. 1D) Mice that received rH19-20 developed severe tubular injury in the outer medulla and severe injury extended into the cortex (inset). (FIG. 1E) After twenty-four hours of reperfusion, serum urea nitrogen (SUN) levels were also significantly higher in mice treated with rH19-20 than those that received vehicle.

(FIG. 2A) Levels of factor H within the kidney increased during reperfusion. (FIG. 2B) Levels of factor H were increased in both wild-type and factor B deficient (fB−/−) mice, demonstrating that tissue bound C3 fragments are not required for factor H to bind within the tissue.

(FIG. 3A) At baseline, isolated deposits of C3 were observed in the tubulointerstitium and little factor H was observed. After 8 hours (FIG. 3B) and 24 hours (FIG. 3C) of reperfusion, increasing quantities of both C3 and factor H were detected in the tubulointerstitium. (FIG. 3D) A high-powered view of the kidney after 24 hours of reperfusion demonstrates that factor H is localized over damaged tubules, but does not co-localize with tissue deposits of C3. (FIG. 3E) By 48 hours of reperfusion, tissue bound factor H and C3 are similar to baseline levels. (FIG. 3F) A section of a kidney at 24 hours of reperfusion was stained with a secondary antibody only to demonstrate specificity of the staining for C3 and factor H. Original magnification ×200 A-C, E, F and ×400 D.

(FIG. 4A) Protein lysates of un-manipulated kidneys and kidneys subjected to I/R were separated by SDS-PAGE and transferred to nitrocellulose membrane. The membrane was incubated with biotinylated factor H to determine whether protein binding partners were present. Some binding partners appeared more abundant in the post-ischemic lysates (arrow). (FIG. 4B) Biotinylated factor H was next incubated with tissue lysates. Streptavidin beads were used to pull down the factor H along with binding partners, and the proteins were examined by Coomassie staining. Again, some binding partners appeared more abundant in lysates from post-ischemic tissue (arrow). The ~39 kD protein was digested with trypsin and analyzed by reverse phase nanospray LC-MS/MS and was identified with high confidence as Annexin A2. (FIG. 4C) Typically, at least 2 peptide hits are sought to confirm a protein's identity. We obtained 6 unique peptides for annexin A2, and three were manually confirmed. FIG. 4C shows the MS spectrum for one of the peptides: SLYYYIQQDTK (SEQ ID NO:31).

(FIG. 5A) Annexin A2 was detected in glomeruli and around injured tubules of the outer medulla. Original magnification ×400. (FIG. 5B) Biotinylated factor H was used to pull-down binding partners which were then separated by SDS-PAGE and probed with a monoclonal antibody to annexin A2. Factor H bound to a greater abundance of annexin A2 in the lysates of post-ischemic kidneys.

DETAILED DESCRIPTION OF THE SEQUENCES

Figure 1A:
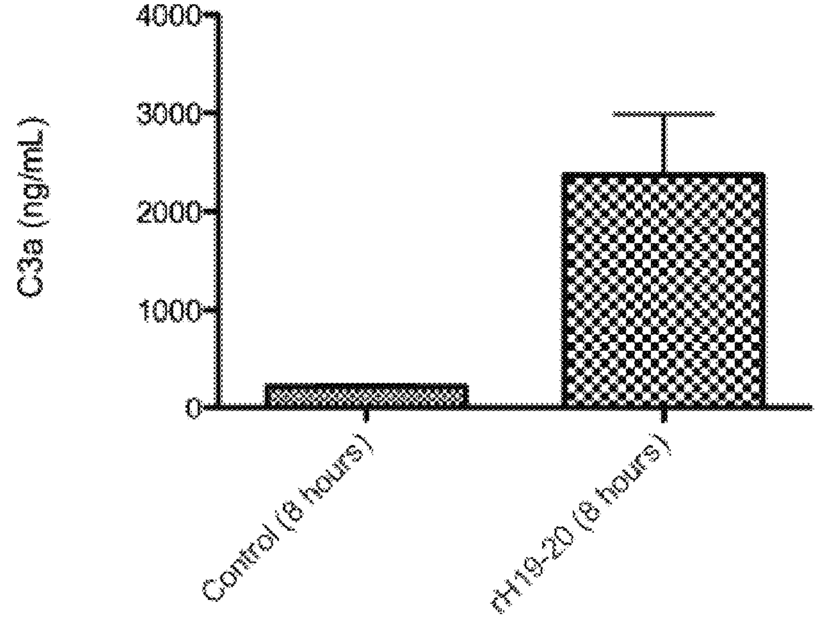
FIGS. 1A-1E. Blockade of surface inhibition by factor H amplifies renal injury after I/R. Mice were subjected to renal I/R. After four hours of reperfusion the mice received a tail-vein injection of vehicle or rH19-20.

SEQ ID NO:1 is the amino acid sequence of full-length human annexin A2 protein.

SEQ ID NO:2 is the nucleotide sequence of full-length human annexin A2 protein.

SEQ ID NO:3 is the amino acid sequence of full-length human factor H.

SEQ ID NO:4 is the nucleotide sequence of a cDNA encoding full-length human factor H.

SEQ ID NO:5 is the amino acid sequence of a fragment of human factor H comprising short consensus repeat sequences 1 to 4.

SEQ ID NO:6 is the amino acid sequence of a fragment of human factor H comprising short consensus repeat sequences 1 to 8.

SEQ ID NO:7 is the amino acid sequence of a fragment of human factor H comprising short consensus repeat sequences 1 to 18.

SEQ ID NO:8 is the amino acid sequence of a fragment of human factor H comprising short consensus repeat sequences 19 to 20.

SEQ ID NO:9 is the amino acid sequence of full-length mouse factor H.

SEQ ID NO:10 is the nucleotide sequence of a cDNA encoding full-length mouse factor H.

SEQ ID NO:11 is the amino acid sequence of the signal peptide of human CD5 protein.

SEQ ID NO:12 is the nucleotide sequence of the signal peptide of human CD5 protein.

SEQ ID NO:13 is the amino acid sequence of the signal peptide of human CR2 protein, short version.

SEQ ID NO:14 is the nucleotide sequence of the signal peptide of human CR2 protein, short version.

SEQ ID NO:15 is the amino acid sequence of the signal peptide of human CR2 protein, long version.

SEQ ID NO:16 is the nucleotide sequence of the signal peptide of human CR2 protein, long version.

SEQ ID NO:17 is the amino acid sequence of human decay accelerating factor (DAF).

SEQ ID NO:18 is the nucleotide sequence of a cDNA encoding human decay accelerating factor (DAF).

SEQ ID NO:19 is the amino acid sequence of human membrane cofactor protein (MCP) protein.

SEQ ID NO:20 is the nucleotide sequence of a cDNA encoding human membrane cofactor protein (MCP) protein.

SEQ ID NO:21 is the amino acid sequence of human CD59 protein.

SEQ ID NO:22 is the nucleotide sequence of a cDNA encoding full-length human CD59 protein.

SEQ ID NO:23 is the amino acid sequence of human CR1 protein.

SEQ ID NO:24 is the nucleotide sequence of a cDNA encoding full-length human CR1 protein.

SEQ ID NO:25 is the amino acid sequence of mouse Crry protein.

SEQ ID NO:26 is the nucleotide sequence of a cDNA encoding full-length mouse Crry protein.

SEQ ID NO:27 to SEQ ID NO:29 are antisense oligodeoxynucleotides against annexin 2 as described herein.

DETAILED DESCRIPTION OF THE INVENTION

The alternative pathway of complement is an important part of the innate immune system, but uncontrolled alternative pathway activation contributes to tissue injury in a wide variety of diseases including renal ischemia/reperfusion (I/R) and ischemic acute kidney injury. Factor H, a circulating alternative pathway regulator, cannot entirely prevent alternative complement-mediated injury in the kidney after I/R, suggesting that factor H has limited efficacy at preventing complement activation on the renal tubules, despite the fact that the tissue-bound level of native factor H increases during reperfusion. We demonstrate herein that factor H binds to annexin A2 in post-ischemic kidneys, and that mice that do not express annexin A2 develop more severe injury after renal I/R. We conclude that the inability of native factor H to prevent complement activation on the renal tubules after I/R results from its insufficient binding affinity for renal epithelial cells, and that expression of protein ligands for factor H during reperfusion is critical to limiting alternative complement-mediated renal injury resulting from I/R.

Definitions

General reference to “the composition” or “compositions” includes and is applicable to compositions of the invention.

As used herein, the singular form of the articles “a,” “an,” and “the” includes plural references unless indicated otherwise. For example, the phrase “a biologically-active CR2 fragment” includes one or more biologically-active CR2 fragments.

Reference to “about” a value or parameter herein includes (and describes) embodiments that are directed to that value or parameter per se. For example, description referring to “about X” includes description of “X.”

It is understood that aspects and embodiments of the invention described herein include consisting and/or consisting essentially of aspects and embodiments.

As used herein, the term individual refers to a vertebrate, preferably a mammal, more preferably a human. Mammals include, but are not limited to, farm animals, sport animals, pets, primates, mice and rats. In certain embodiments, the individual is human. In certain embodiments, the individual is an individual other than a human. In certain embodiments, the individual is an animal model for the study of a disease in which the alternative complement pathway is implicated.

Provided herein are compositions and methods for modulating, i.e., stimulating or inhibiting, activity of the alternative complement pathway, and methods of identifying factor H binding proteins.

Compositions for Modulating Activity of the Alternative Complement Pathway

In one aspect, there are provided a composition or compositions suitable for modulating, i.e., stimulating or inhibiting, activity of the alternative complement pathway. In certain embodiments, the compositions are suitable for inhibiting activity of the alternative complement pathway in the kidneys. In certain embodiments, the compositions suitable for inhibiting activity of the alternative complement pathway comprise human annexin A2 protein (SEQ ID NOs:1 and 2) or biologically-active fragments thereof.

The annexins are a family of calcium-($Ca^{2+}$) and phospholipid-binding proteins that differ from most other $Ca^{2+}$-binding proteins in their $Ca^{2+}$-binding sites. The annexin family $Ca^{2+}$-binding site has a unique architecture that enables annexin family members to reversibly dock onto the periphery of cellular and/or organellar membranes. The conserved $Ca^{2+}$-binding site characteristic of annexin family members is located in the annexin core domain, and comprises four annexin repeats, each seventy (70) amino acids long. The annexin core domain is α-helical and forms a compact, curved disc with a convex surface comprising the $Ca^{2+}$- and membrane-binding sites and a concave side oriented away from the membrane that is available for other types of interaction Annexin family members also typically have an amino-terminal domain of variable length that precedes the annexin core domain and is diverse in sequence and structure. This variable domain mediates regulatory interactions with protein ligands as well as the annexin-membrane association. See U. Rescher et al., *J. Cell Sci.* (2004) 117:2631-2639. Twelve annexin subfamilies have been characterized in vertebrates, each having different splice variants, with different amino-terminal domains and differently positioned $Ca^{2+}$-binding sites.

As used herein, the terms "annexin A2," "annexin II," or "annexin 2" refer to proteins of the annexin A2 subfamily, which have been shown to associate with diverse sites of actin attachment at cell membranes, and to serve a receptors for plasminogen and tissue plasminogen activator, positively modulating the fibrinolytic cascade, among other activities. Id Annexin A2 has also been identified as a component of drusen in monkeys affected with both early- and late-onset macular degeneration. See S. Umeda et al., *FASEB J.* (2005) 19(12):1683-1685 Annexin A2 has not previously been shown to interact with any components of the alternative complement pathway, however. As used herein, the term "biologically-active fragment" of annexin A2, annexin II, or annexin 2, refers to a fragment of annexin A2 capable of interacting with or binding to renal tubules in the kidney and interacting with or binding to factor H or a biologically active fragment thereof. The ability of a biologically-active fragment of annexin A2 to interact with or bind renal tubules or factor H can be assayed by a variety of routine methods known to those skilled in the art, including gel mobility shift assays, Western blot, immunoprecipitation, surface plasmon resonance, and the like.

In certain embodiments, the compositions suitable for inhibiting activity of the alternative complement pathway in the kidneys comprise homologues of human annexin A2 protein (SEQ ID NOs:1 and 2) or biologically-active fragments thereof. A homologue of an annexin A2 protein or biologically-active fragment thereof includes proteins which differ from a naturally occurring human annexin A2 (or from a biologically-active fragment thereof) in that at least one or a few, but not limited to one or a few, amino acids have been deleted (e.g., a truncated version of the protein, such as a peptide or fragment), inserted, inverted, substituted and/or derivatized (e.g., by glycosylation, phosphorylation, acetylation, myristoylation, prenylation, palmitation, amidation and/or addition of glycosylphosphatidyl inositol). For example, a human annexin A2 homologue may have an amino acid sequence that is at least about 70% identical to the amino acid sequence of a naturally occurring human annexin A2 (e.g., SEQ ID NO:1), for example at least about any of 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identical to the amino acid sequence of a naturally occurring human annexin A2 (e.g., SEQ ID NO:1). In certain embodiments, a homologue of human annexin A2 (or a biologically-active fragment thereof) retains all the biological activities of human annexin A2 (or a biologically-active fragment thereof), i.e., the ability to bind renal tubules and to bind factor H. In certain embodiments, the homologue of human annexin A2 (or a biologically-active fragment thereof) retains at least about 50%, for example, at least about any of 60%, 70%, 80%, 90%, or 95% of the biological activity of annexin A2 (or a biologically-active fragment thereof).

Amino acid sequence identity can be determined in various ways, for example, using publicly available computer software such as BLAST, BLAST-2, ALIGN or MEGALIGN™ (DNASTAR) software. One skilled in the art can determine appropriate parameters for measuring alignment, including any algorithms needed to achieve maximal alignment over the full length of the sequences being compared.

In another aspect, the compositions suitable for inhibiting activity of the alternative complement pathway comprise a fusion protein comprising an anti-annexin A2 antibody or antigen-binding fragment thereof fused to a complement inhibitor. In certain embodiments, the complement inhibitor is selected from the group consisting of decay accelerating factor (DAF), factor H, membrane cofactor protein (MCP), CD59, complement receptor 1 (CR1), and mouse complement receptor 1-related gene/protein y ("Crry").

As used herein, the term "decay accelerating factor," "DAF," or "CD55" refers to a seventy kilodalton ("kD") membrane glycoprotein comprising four short consensus repeat (SCR) domains followed by a heavily 0-glycosylated serine/threonine-rich domain at the C-terminus that elevates the molecule from the membrane surface, including homologues thereof. DAF is anchored into the cell membrane by a glycosylphosphatidylinositol ("GPI") anchor. DAF protects the cell surface from complement activation by dissociating membrane-bound C3 convertases that are required to cleave complement protein C3 and to amplify the alternative complement cascade.

SEQ ID NO:17 represents the full-length human DAF amino acid sequence (see, e.g., UniProtKB/Swiss-Prot. Accession No. P08173). Amino acids 1-34 correspond to the signal peptide, amino acids 35-353 appear in the mature protein, and amino acids 354-381 are removed from the polypeptide after translation. Within the mature protein, amino acids 35-96 correspond to SCR 1, amino acids 96-160 correspond to SCR 2, amino acids 161-222 correspond to SCR 3, amino acids 223-285 correspond to SCR 4, and amino acids 287-353 correspond to the O-glycosylated serine/threonine-rich domain. The GPI anchor is attached to DAF at a serine at position 353. It is understood that species and strain variations exist for the disclosed peptides, polypeptides, and proteins, and that DAF or biologically-active fragments thereof encompasses all species and strain variations. As used herein, the term "biologically-active" fragment of DAF refers to any fragment of DAF lacking a GPI anchor and/or the amino acid to which it is attached (i.e., Ser-353), including any fragments of the full-length DAF protein comprising, consisting essentially of or consisting of 1, 2, 3, or 4 SCR domains, with or without the O-glycosylated serine/threonine-rich domain, having some or all the complement inhibitory activity of the full-length DAF protein.

In certain embodiments, the compositions suitable for inhibiting activity of the alternative complement pathway in the kidneys comprise a fusion protein comprising an anti-annexin A2 antibody or antigen-binding fragment thereof fused to full-length human decay-accelerating factor (DAF) (SEQ ID NOs:17 and 18) or a biologically-active fragment thereof. In certain embodiments, the biologically-active fragment of human DAF comprises the mature human DAF protein (amino acids 35-353 of SEQ ID NO:17) without its GPI anchor or short consensus repeat sequences 1 to 4 (SCRs 1 to 4) of full-length human DAF (amino acids 35 to 285 of SEQ ID NO:17). The anti-annexin A2 antibody or antigen-binding portion of the fusion protein is responsible for delivering the composition to renal sites of alternative complement activation by selectively binding to annexin A2 expressed in the kidneys, while the DAF portion of the fusion protein is responsible for inhibiting activity of the alternative complement pathway.

In certain embodiments, the fusion protein comprises an anti-annexin A2 antibody or antigen-binding fragment thereof fused to full-length human DAF. In certain embodiments, the fusion protein comprises an anti-annexin A2 antibody or antigen-binding fragment thereof fused to a biologically active fragment of full-length human DAF. In certain embodiments, the fusion protein comprises an anti-annexin A2 antibody or antigen-binding fragment thereof fused to a biologically active fragment of full-length human DAF comprising the full-length protein lacking its GPI anchor (amino acids 35-353 of SEQ ID NO:17). In certain embodiments, the fusion protein comprises an anti-annexin A2 antibody or antigen-binding fragment thereof fused to a biologically active fragment of full-length human DAF comprising short consensus repeat sequences 1 to 4 (SCRs 1 to 4)(amino acids 35 to 285 of SEQ ID NO:17).

A homologue of a human DAF protein or a biologically-active fragment thereof includes proteins which differ from a naturally occurring human DAF (or biologically-active fragment thereof) in that at least one or a few, but not limited to one or a few, amino acids have been deleted (e.g., a truncated version of the protein, such as a peptide or fragment), inserted, inverted, substituted and/or derivatized (e.g., by glycosylation, phosphorylation, acetylation, myristoylation, prenylation, palmitation, amidation and/or addition of glycosylphosphatidyl inositol). For example, a human DAF homologue may have an amino acid sequence that is at least about 70% identical to the amino acid sequence of a naturally occurring human DAF (e.g., SEQ ID NO:17), for example at least about any of 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identical to the amino acid sequence of a naturally occurring human DAF (e.g., SEQ ID NO:17). In certain embodiments, a homologue of human DAF (or a biologically-active fragment thereof) retains all the alternative complement pathway inhibitory activity of human DAF (or a biologically-active fragment thereof). In certain embodiments, the homologue of human DAF (or a biologically-active fragment thereof) retains at least about 50%, for example, at least about any of 60%, 70%, 80%, 90%, or 95% of the complement inhibition activity of human DAF (or a biologically-active fragment thereof).

As used herein, the term "complement factor H," "factor H," or "FH" refers to complement factor H, a single polypeptide chain plasma glycoprotein, including homologues thereof. The protein is composed of 20 conserved short consensus repeat (SCR) domains of approximately 60 amino acids, arranged in a continuous fashion like a string of beads, separated by short linker sequences of 2 to 6 amino acids each. Factor H binds to C3b, accelerates the decay of the alternative pathway C3-convertase (C3bBb), and acts as a cofactor for the proteolytic inactivation of C3b. In the presence of factor H, C3b proteolysis results in the cleavage of C3b. Factor H has at least three distinct binding domains for C3b, which are located within SCRs 1-4, SCRs 5-8, and SCRs 19-20. Each site of factor H binds to a distinct region within the C3b protein: the N-terminal sites bind to native C3b; the second site, located in the middle region of factor H, binds to the C3c fragment and the site located within SCR19 and 20 binds to the C3d region. In addition, factor H also contains binding sites for heparin, which are located within SCR 7, SCRs 5-12, and SCR 20 of factor H and overlap with those of the C3b binding sites. Structural and functional analyses have shown that the domains for the complement inhibitory activity of factor H are located within the first four N-terminal SCR domains.

SEQ ID NO:3 represents the full-length human factor H amino acid sequence (see, e.g., UniProtKB/Swiss-Prot. Accession No. P08603). Amino acids 1-18 correspond to the signal peptide, and amino acids 19-1231 correspond to the mature protein. Within that protein, amino acids 21-80 correspond to SCR 1, amino acids 85-141 correspond to SCR 2, amino acids 146-205 correspond to SCR 3, amino acids 210-262 correspond to SCR 4, and amino acids 267-320 correspond to SCR 5. The full-length mouse factor H amino acid sequence is represented herein by SEQ ID NO:9 (see, e.g., UniProtKB/Swiss-Prot. Accession No. P06909). Amino acids 1-18 correspond to the signal peptide, and amino acids 19-1234 correspond to the mature protein. Within that protein, SCRs 1 and 2 domains of mouse factor H protein are located within the mouse factor H amino sequence at positions 19-82 of SEQ ID NO:9 (SCR 1) and positions 83-143 of SEQ ID NO:9 (SCR 2). Human and mouse factor H are approximately 61% identical over the full length amino acid sequences represented by SEQ ID NO:3 and SEQ ID NO:9. It is understood that species and strain variations exist for the disclosed peptides, polypeptides, and proteins, and that factor H or biologically-active fragments thereof encompasses all species and strain variations.

As used herein, the term "biologically-active" fragment of factor H refers to any portion of a factor H protein having some or all the complement inhibitory activity of the full-length factor H protein, and includes, but is not limited to, factor H fragments comprising SCRs 1 to 4, SCRs 1 to 8, SCRs 1 to 18, SCRs 19 to 20, or any homologue of a naturally-occurring factor H or fragment thereof, as described in detail below. In certain embodiments, the biologically-active fragment of factor H has one or more of the following properties: (1) binding to C-reactive protein (CRP), (2) binding to C3b, (3) binding to heparin, (4) binding to sialic acid, (5) binding to endothelial cell surfaces, (6) binding to cellular integrin receptor, (7) binding to pathogens, (8) C3b co-factor activity, (9) C3b decay-acceleration activity, and (10) inhibiting the alternative complement pathway.

In certain embodiments, the compositions suitable for inhibiting activity of the alternative complement pathway in the kidneys comprise a fusion protein comprising an anti-annexin A2 antibody or antigen-binding fragment thereof fused to human factor H (SEQ ID NOs:3 and 4) or a biologically-active fragment thereof. In certain embodiments, the biologically-active fragment of human factor H comprises short consensus repeat sequences 1 to 4 (SCRs 1 to 4)(SEQ ID NO:5), short consensus repeat sequences 1 to 8 (SCRs 1 to 8)(SEQ ID NO:6), or short consensus repeat sequences 1 to 18 (SCRs 1 to 18)(SEQ ID NO:7). The anti-annexin A2 antibody or antigen-binding portion of the fusion protein is responsible for delivering the composition to renal sites of alternative complement activation by selectively binding to annexin A2 expressed in the kidneys, while the factor H portion of the fusion protein is responsible for inhibiting activity of the alternative complement pathway.

In certain embodiments, the fusion protein comprises an anti-annexin A2 antibody or antigen-binding fragment thereof fused to full-length human factor H. In certain embodiments, the fusion protein comprises an anti-annexin A2 antibody or antigen-binding fragment thereof fused to a biologically active fragment of full-length human factor H comprising SCRs 1 to 4. In certain embodiments, the fusion protein comprises an anti-annexin A2 antibody or antigen-binding fragment thereof fused to a biologically active fragment of full-length human factor H comprising SCRs 1 to 8. In certain embodiments, the fusion protein comprises an anti-annexin A2 antibody or antigen-binding fragment thereof fused to a biologically active fragment of full-length human factor H comprising SCRs 1 to 18.

In certain embodiments, the biologically-active fragment of factor H comprises the first four N-terminal SCR domains of factor H. In certain embodiments, the biologically-active fragment of factor H comprises the first five N-terminal SCR domains of factor H. In certain embodiments, the biologically-active fragment of factor H comprises the first six N-terminal SCR domains of factor H. In certain embodiments, the biologically-active fragment of factor H comprises the first eight N-terminal SCR domains of factor H. In certain embodiments, the biologically-active fragment of factor H comprises the first eighteen N-terminal SCR domains of factor H. In certain embodiments, the biologically-active fragment of factor H comprises SCRs 1 to 4 of factor H. In certain embodiments, the biologically-active fragment of factor H comprises SCRs 1 to 8 of factor H. In certain embodiments, the biologically-active fragment of factor H comprises SCRs 1 to 18 of factor H. In certain embodiments, the biologically-active factor H fragment comprises (and in certain embodiments consists of or consists essentially of) at least the first four N-terminal SCR domains of factor H, including for example, at least any of the first 5, 6, 7, 8, 9, 10, 11, 12, 13, 14, 15, 16, 17, 18, or more N-terminal SCR domains of factor H.

In certain embodiments, the biologically-active fragment of factor H is derived from a wild-type factor H. In certain embodiments, the biologically-active fragment of factor H is derived from a naturally-occurring protective variant of factor H.

In certain embodiments, the biologically-active fragment of factor H lacks a heparin binding site. This can be achieved, for example, by mutation of the heparin binding site on a biologically-active fragment of factor H, or by selecting biologically-active factor H fragments that do not contain a heparin binding site. In certain embodiments, the biologically-active fragment of factor H has a polymorphism that is protective to age-related macular degeneration. See Hageman et al., *Proc. Nat'l Acad. Sci. USA* 102(20):7227.

A homologue of a human factor H protein or a biologically-active fragment thereof includes proteins which differ from a naturally occurring human factor H (or biologically-active fragment thereof) in that at least one or a few, but not limited to one or a few, amino acids have been deleted (e.g., a truncated version of the protein, such as a peptide or fragment), inserted, inverted, substituted and/or derivatized (e.g., by glycosylation, phosphorylation, acetylation, myristoylation, prenylation, palmitation, amidation and/or addition of glycosylphosphatidyl inositol). For example, a human factor H homologue may have an amino acid sequence that is at least about 70% identical to the amino acid sequence of a naturally occurring human factor H (e.g., SEQ ID NO:3), for example at least about any of 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identical to the amino acid sequence of a naturally occurring human factor H (e.g., SEQ ID NO:3). In certain embodiments, a homologue of human factor H (or a biologically-active fragment thereof) retains all the alternative complement pathway inhibitory activity of human factor H (or a biologically-active fragment thereof). In certain embodiments, the homologue of human factor H (or a biologically-active fragment thereof) retains at least about 50%, for example, at least about any of 60%, 70%, 80%, 90%, or 95% of the complement inhibition activity of human factor H (or a biologically-active fragment thereof).

In certain embodiments, the biologically-active fragment of factor H comprises at least the first four N-terminal SCR domains of a human factor H, such as a factor H portion having an amino acid sequence containing at least amino acids 21 through 262 of the human factor H (SEQ ID NO:3). In certain embodiments, the biologically-active fragment of factor H comprises at least the first four N-terminal SCR domains of human factor H having an amino acid sequence that is at least about any of 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% identical to amino acids 21 through 262 of the human factor H (SEQ ID NO:3).

In certain embodiments, the biologically-active fragment of factor H comprises at least the first five N-terminal SCR domains of a human factor H, such as a factor H portion having an amino acid sequence containing at least amino acids 21 through 320 of the human factor H (SEQ ID NO:3). In certain embodiments, the biologically-active fragment of factor H comprises at least the first five N-terminal SCR domains of human factor H having an amino acid sequence that is at least about any of 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% identical to amino acids 21 through 320 of the human factor H (SEQ ID NO:3).

In certain embodiments, the biologically-active fragment of factor H comprises at least the first eight N-terminal SCR domains of a human factor H, such as a factor H portion having an amino acid sequence containing at least amino acids 21 through 509 of the human factor H (SEQ ID NO:3). In certain embodiments, the biologically-active fragment of factor H comprises at least the first eight N-terminal SCR domains of human factor H having an amino acid sequence that is at least about any of 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% identical to amino acids 21 through 509 of the human factor H (SEQ ID NO:3).

In certain embodiments, the biologically-active fragment of factor H comprises at least the first eighteen N-terminal SCR domains of a human factor H, such as a factor H portion having an amino acid sequence containing at least amino acids 21 through 1106 of the human factor H (SEQ ID NO:3). In certain embodiments, the biologically-active fragment of factor H comprises at least the first eighteen N-terminal SCR domains of human factor H having an amino acid sequence that is at least about any of 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% identical to amino acids 21 through 1106 of the human factor H (SEQ ID NO:3).

As used herein, the term "membrane cofactor protein," "MCP," or "CD46" refers to a widely distributed C3b/C4b-binding cell surface glycoprotein which inhibits complement activation on host cells and serves as a cofactor for the factor I-mediated cleavage of C3b and C4b, including homologues thereof. See T. J. Oglesby et al., *J. Exp. Med.* (1992) 175:1547-1551. MCP belongs to a family known as the regulators of complement activation ("RCA"). Family members share certain structural features, comprising varying numbers of short consensus repeat (SCR) domains, which are typically between 60 and 70 amino acids in length. MCP comprises four SCRs, a serine/threonine/proline-enriched region, an area of undefined function, a transmembrane hydrophobic domain, a cytoplasmic anchor and a cytoplasmic tail. It is understood that species and strain variations exist for the disclosed peptides, polypeptides, and proteins, and that human MCP or biologically-active fragments thereof encompasses all species and strain variations.

SEQ ID NO:19 represents the full-length human MCP amino acid sequence (see, e.g., UniProtKB/Swiss-Prot. Accession No. P15529). Amino acids 1-34 correspond to the signal peptide, amino acids 35-343 correspond to the extracellular domain, amino acids 344-366 correspond to the transmembrane domain, and amino acids 367-392 correspond to the cytoplasmic domain. In the extracellular domain, amino acids 35-96 correspond to SCR 1, amino acids 97-159 correspond to SCR 2, amino acids 160-225 correspond to SCR 3, amino acids 226-285 correspond to SCR 4, and amino acids 302-326 correspond to the serine/threonine-rich domain. It is understood that species and strain variations exist for the disclosed peptides, polypeptides, and proteins, and that MCP or biologically-active fragments thereof encompasses all species and strain variations. As used herein, the term "biologically-active" fragment of MCP refers to any soluble fragment lacking both the cytoplasmic domain and the transmembrane domain, including fragments comprising, consisting essentially of or consisting of 1, 2, 3, or 4 SCR domains, with or without the serine/threonine-rich domain, having some or all the complement inhibitory activity of the full-length MCP protein.

In certain embodiments, the compositions suitable for inhibiting activity of the alternative complement pathway in the kidneys comprise a fusion protein comprising an anti-annexin A2 antibody or antigen-binding fragment thereof fused to human membrane cofactor protein (MCP) (SEQ ID NOs:19 and 20) or a biologically-active fragment thereof. In certain embodiments, the biologically-active fragment of human MCP comprises the extracellular domain of human MCP (amino acids 35-343 of SEQ ID NO:19), or SCRs 1 to 4 of human MCP (amino acids 35-285 of SEQ ID NO:19). The anti-annexin A2 antibody or antigen-binding portion of the fusion protein is responsible for delivering the composition to renal sites of alternative complement activation by selectively binding to annexin A2 expressed in the kidneys, while the MCP portion of the fusion protein is responsible for inhibiting activity of the alternative complement pathway.

In certain embodiments, the fusion protein comprises an anti-annexin A2 antibody or antigen-binding fragment thereof fused to full-length human MCP. In certain embodiments, the fusion protein comprises an anti-annexin A2 antibody or antigen-binding fragment thereof fused to a biologically active fragment of full-length human MCP. In certain embodiments, the fusion protein comprises an anti-annexin A2 antibody or antigen-binding fragment thereof fused to a biologically active fragment of full-length human MCP comprising the extracellular domain of human MCP (amino acids 35-343 of SEQ ID NO:19). In certain embodiments, the fusion protein comprises an anti-annexin A2 antibody or antigen-binding fragment thereof fused to a biologically active fragment of full-length human MCP comprising SCRs 1 to 4 (amino acids 35-285 of SEQ ID NO:19.

A homologue of a human MCP protein or a biologically-active fragment thereof includes proteins which differ from a naturally occurring human MCP (or biologically-active fragment thereof) in that at least one or a few, but not limited to one or a few, amino acids have been deleted (e.g., a truncated version of the protein, such as a peptide or fragment), inserted, inverted, substituted and/or derivatized (e.g., by glycosylation, phosphorylation, acetylation, myristoylation, prenylation, palmitation, amidation and/or addition of glycosylphosphatidyl inositol). For example, a human MCP homologue may have an amino acid sequence that is at least about 70% identical to the amino acid sequence of a naturally occurring human MCP (e.g., SEQ ID NO:19), for example at least about any of 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identical to the amino acid sequence of a naturally occurring human MCP (e.g., SEQ ID NO:19). In certain embodiments, a homologue of human MCP (or a biologically-active fragment thereof) retains all the alternative complement pathway inhibitory activity of human MCP (or a biologically-active fragment thereof). In certain embodiments, the homologue of human MCP (or a biologically-active fragment thereof) retains at least about 50%, for example, at least about any of 60%, 70%, 80%, 90%, or 95% of the complement inhibition activity of human MCP (or a biologically-active fragment thereof).

As used herein, the term "CD59" refers to a membrane-bound 128 amino acid glycoprotein that potently inhibits the membrane attack complex (MAC) of complement, including homologues thereof. CD59 acts by binding to the C8 and/or C9 components of the MAC during assembly, ultimately preventing incorporation of the multiple copies of C9 required for complete formation of the osmolytic pore at the heart of the MAC. CD59 is both N- and O-glycosylated. The N-glycosylation comprises primarily of bi- or tri-antennary structures with and without lactosamine and outer arm fucose residues, with variable sialylation present at some sites. Like DAF, CD59 is anchored in the cell membrane by a glycosylphosphatidylinositol ("GPI") anchor, which is attached to an asparagine at amino acid 102.

SEQ ID NO:21 represents the full-length human CD59 amino acid sequence (see, e.g., UniProtKB/Swiss-Prot. Accession No. P13987). Amino acids 1-25 correspond to the leader peptide, amino acids 26-102 correspond to the mature protein, and amino acids 103-128 are removed after translation. The GPI anchor is attached to CD59 at an asparagine at position 102. It is understood that species and strain variations exist for the disclosed peptides, polypeptides, and proteins, and that CD59 or biologically-active fragments thereof encompasses all species and strain variations. As used herein, the term "biologically-active" fragment of CD59 refers to any fragment of CD59 lacking a GPI anchor and/or the amino acid to which it is attached (i.e., Asn-102), including any fragments of the full-length CD59 protein having some or all the complement inhibitory activity of the full-length CD59 protein.

In certain embodiments, the compositions suitable for inhibiting activity of the alternative complement pathway in the kidneys comprise a fusion protein comprising an anti-annexin A2 antibody or antigen-binding fragment thereof fused to human CD59 (SEQ ID NOs:21 and 22) or a biologically-active fragment thereof. In certain embodiments, the biologically-active fragment of human CD59 comprises the extracellular domain of human CD59 (amino acids 26-102 of SEQ ID NO:21) lacking its GPI anchor and/or the amino acid to which it is attached (i.e., Asn-102). The anti-annexin A2 antibody or antigen-binding portion of the fusion protein is responsible for delivering the composition to renal sites of alternative complement activation by selectively binding to annexin A2 expressed in the kidneys, while the CD59 portion of the fusion protein is responsible for inhibiting activity of the alternative complement pathway.

In certain embodiments, the fusion protein comprises an anti-annexin A2 antibody or antigen-binding fragment thereof fused to full-length human CD59. In certain embodiments, the fusion protein comprises an anti-annexin A2 antibody or antigen-binding fragment thereof fused to a biologically active fragment of full-length human CD59. In certain embodiments, the fusion protein comprises an anti-annexin A2 antibody or antigen-binding fragment thereof fused to a biologically active fragment of full-length human CD59 comprising the extracellular domain of human CD59 (amino acids 26-102 of SEQ ID NO:21) lacking its GPI anchor and/or the amino acid to which it is attached (i.e., Asn-102).

A homologue of a human CD59 protein or a biologically-active fragment thereof includes proteins which differ from a naturally occurring human CD59 (or biologically-active fragment thereof) in that at least one or a few, but not limited to one or a few, amino acids have been deleted (e.g., a truncated version of the protein, such as a peptide or fragment), inserted, inverted, substituted and/or derivatized (e.g., by glycosylation, phosphorylation, acetylation, myristoylation, prenylation, palmitation, amidation and/or addition of glycosylphosphatidyl inositol). For example, a human MCP homologue may have an amino acid sequence that is at least about 70% identical to the amino acid sequence of a naturally occurring human CD59 (e.g., SEQ ID NO:21), for example at least about any of 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identical to the amino acid sequence of a naturally occurring human CD59 (e.g., SEQ ID NO:21). In certain embodiments, a homologue of human CD59 (or a biologically-active fragment thereof) retains all the alternative complement pathway inhibitory activity of human CD59 (or a biologically-active fragment thereof). In certain embodiments, the homologue of human CD59 (or a biologically-active fragment thereof) retains at least about 50%, for example, at least about any of 60%, 70%, 80%, 90%, or 95% of the complement inhibition activity of human CD59 (or a biologically-active fragment thereof).

As used herein, the term "complement receptor 1," "CR1," or "CD35" refers to a human gene encoding a protein of 2039 amino acids, with a predicted molecular weight of 220 kilodaltons ("kD"), including homologues thereof. The gene is expressed principally on erythrocytes, monocytes, neutrophils, and B cells, but is also present on some T lymphocytes, mast cells, and glomerular podocytes. CR1 protein is typically expressed at between 100 and 1000 copies per cell. The full-length CR1 protein comprises a 42 amino acid signal peptide, an extracellular domain of 1930 amino acids, a 25 amino acid transmembrane domain, and a 43 amino acid C-terminal cytoplasmic domain. The extracellular domain of CR1 has 25 potential N-glycosylation signal sequences, and comprises 30 short consensus ("SCR") domains, also known as complement control protein (CCP) repeats, or sushi domains, each 60 to 70 amino acids long. The sequence homology between SCRs ranges between 60 to 99 percent. The 30 SCR domains are further grouped into four longer regions termed long homologous repeats ("LHRs"), each encoding approximately 45 kD segments of the CR1 protein, designated LHR-A, -B, -C, and -D. The first three comprise seven SCR domains each, while LHR-D comprises 9 SCR domains. The active sites on the extracellular domain of CR1 protein include a C4b-binding site with lower affinity for C3b in SCRs 1 to 4 comprising amino acids 42-295, a C3b-binding site with lower affinity for C4b in SCRs 8 to 11 comprising amino acids 490-745, a C3b-binding site with lower affinity for C4b in SCRs 15-18 comprising amino acids 940-1196, and a Clq-binding site in SCRs 22-28 comprising amino acids 1394-1842.

SEQ ID NO:23 represents the full-length human CR1 amino acid sequence (see, e.g., UniProtKB/Swiss-Prot. Accession No. P17927). Amino acids 1-41 correspond to the signal peptide, amino acids 42-2039 correspond to the mature protein, comprising amino acids 42-1971, corresponding to the extracellular domain, amino acids 1972-1996, corresponding to the transmembrane domain, and amino acids 1997-2039, corresponding to the cytoplasmic domain. In the extracellular domain, amino acids 42-101 correspond to SCR 1, 102-163 correspond to SCR2, amino acids 164-234 correspond to SCR3, amino acids 236-295 correspond to SCR4, amino acids 295-355 correspond to SCRS, amino acids 356-418 correspond to SCR6, amino acids 419-489 correspond to SCR7, amino acids 491-551 correspond to SCR8, amino acids 552-613 correspond to SCR9, amino acids 614-684 correspond to SCR10, amino acids 686-745 correspond to SCR11, amino acids 745-805 correspond to SCR12, amino acids 806-868 correspond to SCR13, amino acids 869-939 correspond to SCR14, amino acids 941-1001 correspond to SCR15, amino acids 1002-1063 correspond to SCR16, amino acids 1064-1134 correspond to SCR17, amino acids 1136-1195 correspond to SCR18, amino acids 1195-1255 correspond to SCR 19, amino acids 1256-1318 correspond to SCR 20, amino acids 1319-1389 correspond to SCR 21, amino acids 1394-1454 correspond to SCR 22, amino acids 1455-1516 correspond to SCR 23, amino acids 1517-1587 correspond to SCR 24, amino acids 1589-1648 correspond to SCR 25, amino acids 1648-1708 correspond to SCR 26, amino acids 1709-1771 correspond to SCR 27, amino acids 1772-1842 correspond to SCR 28, amino acids 1846-1906 correspond to SCR 29, amino acids 1907-1967 correspond to SCR 30. It is understood that species and strain variations exist for the disclosed peptides, polypeptides, and proteins, and that CR1 protein or biologically-active fragments thereof encompasses all species and strain variations. As used herein, the term "biologically-active" fragment of CR1 protein refers to refers to any soluble fragment of CR1 lacking the transmembrane domain and the cytoplasmic domain, including fragments comprising, consisting essentially of or consisting of 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 SCR domains, including any fragments of the full-length CR1 protein having some or all the complement inhibitory activity of the full-length CR1 protein.

A homologue of a human CR1 protein or a biologically-active fragment thereof includes proteins which differ from a naturally occurring human CR1 (or biologically-active fragment thereof) in that at least one or a few, but not limited to one or a few, amino acids have been deleted (e.g., a truncated version of the protein, such as a peptide or fragment), inserted, inverted, substituted and/or derivatized (e.g., by glycosylation, phosphorylation, acetylation, myristoylation, prenylation, palmitation, amidation and/or addition of glycosylphosphatidyl inositol). For example, a human CR1 homologue may have an amino acid sequence that is at least about 70% identical to the amino acid sequence of a naturally occurring human CR1 (e.g., SEQ ID NO:23), for example at least about any of 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identical to the amino acid sequence of a naturally occurring human CR1 (e.g., SEQ ID NO:23). In certain embodiments, a homologue of human CR1 (or a biologically-active fragment thereof) retains all the alternative complement pathway inhibitory activity of human CR1 (or a biologically-active fragment thereof). In certain embodiments, the homologue of human CR1 (or a biologically-active fragment thereof) retains at least about 50%, for example, at least about any of 60%, 70%, 80%, 90%, or 95% of the complement inhibition activity of human CR1 (or a biologically-active fragment thereof).

In certain embodiments, the compositions suitable for inhibiting activity of the alternative complement pathway in the kidneys comprise a fusion protein comprising an anti-annexin A2 antibody or antigen-binding fragment thereof fused to human CR1 (SEQ ID NOs:23 and 24) or a biologically-active fragment thereof. In certain embodiments, the biologically-active fragment of human CR1 comprises the complete extracellular domain of human CR1 (SCRs 1 to 30), SCRs 1 to 4, SCRs 1 to 11, or SCRs 1 to 18. The anti-annexin A2 antibody or antigen-binding portion of the fusion protein is responsible for delivering the composition to renal sites of alternative complement activation by selectively binding to annexin A2 expressed in the kidneys, while the CR1 portion of the fusion protein is responsible for inhibiting activity of the alternative complement pathway.

In certain embodiments, the fusion protein comprises an anti-annexin A2 antibody or antigen-binding fragment thereof fused to full-length human CR1. In certain embodiments, the fusion protein comprises an anti-annexin A2 antibody or antigen-binding fragment thereof fused to a biologically active fragment of full-length human CR1 comprising the complete extracellular domain of human CR1 (SCRs 1 to 30)(amino acids 42-1971 of SEQ ID NO:23). In certain embodiments, the fusion protein comprises an anti-annexin A2 antibody or antigen-binding fragment thereof fused to a biologically active fragment of full-length human CR1 comprising SCRs 1 to 4 (amino acids 42-295 of SEQ ID NO:23). In certain embodiments, the fusion protein comprises an anti-annexin A2 antibody or antigen-binding fragment thereof fused to a biologically active fragment of full-length human CR1 comprising SCRs 1 to 11 (amino acids 42-745 of SEQ ID NO:23). In certain embodiments, the fusion protein comprises an anti-annexin A2 antibody or antigen-binding fragment thereof fused to a biologically active fragment of full-length human CR1 comprising SCRs 1 to 18 (amino acids 42-1195 of SEQ ID NO:23).

As used herein, the term "mouse complement receptor 1-related gene/protein y" or "Crry" refers to a membrane-bound mouse glycoprotein that regulates complement activation, including homologues thereof. Crry regulates complement activation by serving as a cofactor for complement factor I, a serine protease which cleaves C3b and C4b deposited on host tissue. Crry also acts as a decay-accelerating factor, preventing the formation of C4b2a and C3bBb, the amplification convertases of the complement cascade.

SEQ ID NO:25 represents the full-length mouse Crry protein amino acid sequence. Amino acids 1-40 correspond to the leader peptide, amino acids 41-483 correspond to the mature protein, comprising amino acids 41-405, corresponding to the extracellular domain, amino acids 406-426, corresponding to the transmembrane domain, and amino acids 427-483, corresponding to the cytoplasmic domain. In the extracellular domain, amino acids 83-143 correspond to SCR 1, 144-205 correspond to SCR2, amino acids 206-276 correspond to SCR3, amino acids 277-338 correspond to SCR4, and amino acids 339-400 correspond to SCRS. It is understood that species and strain variations exist for the disclosed peptides, polypeptides, and proteins, and that mouse Crry protein or biologically-active fragments thereof encompasses all species and strain variations. As used herein, the term "biologically-active" fragment of mouse Crry protein refers to refers to any soluble fragment of mouse Crry lacking the transmembrane domain and the cytoplasmic domain, including fragments comprising, consisting essentially of or consisting of 1, 2, 3, 4, or 5 SCR domains, including any fragments of the full-length mouse Crry protein having some or all the complement inhibitory activity of the full-length Crry protein.

A homologue of a mouse Crry protein or a biologically-active fragment thereof includes proteins which differ from a naturally occurring mouse Crry protein (or biologically-active fragment thereof) in that at least one or a few, but not limited to one or a few, amino acids have been deleted (e.g., a truncated version of the protein, such as a peptide or fragment), inserted, inverted, substituted and/or derivatized (e.g., by glycosylation, phosphorylation, acetylation, myristoylation, prenylation, palmitation, amidation and/or addition of glycosylphosphatidyl inositol). For example, a mouse Crry protein homologue may have an amino acid sequence that is at least about 70% identical to the amino acid sequence of a naturally occurring mouse Crry protein (e.g., SEQ ID NO:25), for example at least about any of 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identical to the amino acid sequence of a naturally occurring mouse Crry protein (e.g., SEQ ID NO:25). In certain embodiments, a homologue of mouse Crry protein (or a biologically-active fragment thereof) retains all the alternative complement pathway inhibitory activity of mouse Crry protein (or a biologically-active fragment thereof). In certain embodiments, the homologue of mouse Crry protein (or a biologically-active fragment thereof) retains at least about 50%, for example, at least about any of 60%, 70%, 80%, 90%, or 95% of the complement inhibition activity of mouse Crry protein (or a biologically-active fragment thereof).

In certain embodiments, the compositions suitable for inhibiting activity of the alternative complement pathway in the kidneys comprise a fusion protein comprising an anti-annexin A2 antibody or antigen-binding fragment thereof fused to mouse Crry (SEQ ID NOs:25 and 26) or a biologically-active fragment thereof. In certain embodiments, the biologically-active fragment of mouse Crry comprises the complete extracellular domain of mature mouse Crry (amino acids 41-405 of SEQ ID NO:25) or short consensus repeat sequences 1 to 5 (SCRs 1 to 5)(amino acids 83-400 of SEQ ID NO:25). The anti-annexin A2 antibody or antigen-binding portion of the fusion protein is responsible for delivering the composition to renal sites of alternative complement activation by selectively binding to annexin A2 expressed in the kidneys, while the mouse Crry portion of the fusion protein is responsible for inhibiting activity of the alternative complement pathway.

In certain embodiments, the fusion protein comprises an anti-annexin A2 antibody or antigen-binding fragment thereof fused to full-length mouse Crry. In certain embodiments, the fusion protein comprises an anti-annexin A2 antibody or antigen-binding fragment thereof fused to a biologically active fragment of full-length mouse Crry. In certain embodiments, the fusion protein comprises an anti-annexin A2 antibody or antigen-binding fragment thereof fused to a biologically active fragment of full-length mouse Crry comprising the complete extracellular domain of mature mouse Crry (amino acids 41-405 of SEQ ID NO:25). In certain embodiments, the fusion protein comprises an anti-annexin A2 antibody or antigen-binding fragment thereof fused to a biologically active fragment of full-length mouse Crry comprising SCRs 1 to 5 (amino acids 83-400 of SEQ ID NO:25).

In some embodiments, the fusion protein comprising an anti-annexin A2 antibody or antigen-binding fragment thereof and a DAF, factor H, MCP, CD59, CR1, or mouse Crry protein or a biologically-active fragment thereof also includes an amino acid linker sequence linking the anti-annexin A2 portion and the complement inhibitor portion (e.g., the DAF, factor H, MCP, CD59, CR1, or mouse Crry protein portion). Examples of linker sequences are known in the art, and include, for example, $(Gly_4Ser)$, $(Gly_4Ser)_2$, $(Gly_4Ser)_3$, $(Gly_3Ser)_4$, $(SerGly_4)$, $(SerGly_4)_2$, $(SerGly_4)_3$, and $(SerGly_4)_4$. Linking sequences can also comprise "natural" linking sequences found between different domains of complement factors. For example, VSVFPLE (SEQ ID NO:30), the linking sequence between the first two N-terminal short consensus repeat domains of human CR2, can be used. In some embodiments, the linking sequence between the fourth and the fifth N-terminal short consensus repeat domains of human CR2 (EEIF) is used.

As used herein, the term "specifically binds to" or "selectively binds to" refers to the specific binding of one protein to another (e.g., an antibody or antigen-binding fragment thereof to an antigen, or a receptor to a ligand), wherein the level of binding, as measured by any standard assay (e.g., an immunoassay), is statistically significantly higher than the background control for the assay. For example, when performing an immunoassay, controls typically include a reaction well or tube that contains an antibody or antigen-binding fragment thereof alone (i.e., in the absence of antigen), wherein an amount of reactivity (e.g., non-specific binding to the well) by the antibody or antigen-binding fragment thereof in the absence of the antigen is considered to be background. Binding can be measured using a variety of methods standard in the art, including, but not limited to: Western blot, immunoblot, enzyme-linked immunosorbant assay ("ELISA"), radioimmunoassay ("RIA"), immunoprecipitation, surface plasmon resonance, chemiluminescence, fluorescent polarization, phosphorescence, immunohistochemical analysis, matrix-assisted laser desorption/ionization time-of-flight ("MALDI-TOF") mass spectrometry, microcytometry, microarray, microscopy, fluorescence activated cell sorting ("FACS"), and flow cytometry.

As used herein, the term "anti-annexin A2 antibody or antigen-binding fragment thereof" refers to an antibody that specifically or selectively binds to annexin A2, or a fragment of such an antibody that retains the ability to specifically or selectively bind to annexin A2, preferably without interfering with the binding of endogenous native factor H. Antibodies contain immunoglobulin (Ig) domains and are members of the Ig superfamily of proteins. Generally, an antibody molecule comprises two types of chains: a heavy or H chain, and a light or L chain. The light chain contains a variable domain ($V_L$) and a constant domain ($C_L$), while the heavy chain contains a variable domain ($V_H$) and three constant domains ($C_H1$, $C_H2$, and $C_H3$), with the $C_H1$ and $C_H2$ domains separated by a hinge region. The distinctive characteristics of each isotype are defined by sequences in the constant domain of the immunoglobulin. Each antibody molecule typically contains two H chains and two L chains. The two H chains are linked together by disulfide bonds and each H chain is linked to an L chain by a disulfide bond. There are only two types of L chains referred to as lambda ($\lambda$) and kappa ($\kappa$) chains. In contrast, there are five major H chain classes, referred to as isotypes. The five classes include IgM ($\mu$), IgD ($\delta$), IgG ($\lambda$), IgA ($\alpha$), and IgE (or $\varepsilon$). Human immunoglobulin molecules comprise nine isotypes: IgM, IgD, IgE, four subclasses of IgG including $IgG_1$ ($\gamma_1$), $IgG_2$ ($\gamma_2$), $IgG_3$ ($\gamma_3$) and $IgG_4$ ($\gamma_4$), and two subclasses of IgA including $IgA_1$ ($\alpha_1$) and $IgA_2$ ($\alpha_2$).

Together, one H chain and one L chain form an arm of an immunoglobulin molecule having an immunoglobulin variable region. A complete immunoglobulin molecule comprises two di-sulfide linked arms. Thus, each arm of a whole immunoglobulin comprises a $V_{H+L}$ region, and a $C_{H+L}$ region. As used herein, the variable region or V region refers to a $V_{H+L}$ region (also known as an Fv fragment), a $V_L$ region, or a $V_H$ region of an Ig protein. Also as used herein, the term constant region or C region refers to a $C_{H+L}$ region, a $C_L$ region or a $C_H$ region.

Limited digestion of an Ig protein with different proteases produces a number of fragments, only some of which retain the capacity to bind antigen. The antigen-binding fragments are referred to as Fab, Fab', or $F(ab')_2$ fragments. A fragment lacking the ability to bind to antigen is referred to as an Fc fragment. An Fab fragment comprises one arm of an immunoglobulin molecule containing an L chain ($V_L$+$C_L$ domains) paired with the $V_H$ region and the $C_H1$ region. An Fab' fragment corresponds to an Fab fragment with part of the hinge region attached to the $C_H1$ domain. An $F(ab')_2$ fragment corresponds to two Fab' fragments that are normally covalently linked to each other through a disulfide bond, typically in the hinge region.

The anti-annexin A2 antibodies or antigen-binding fragments thereof may also be "chimeric" antibodies in which a portion of the heavy and/or light chain is identical with or homologous to corresponding sequences in antibodies derived from a particular species (e.g., human or mouse and the like) or belonging to a particular antibody class or subclass (e.g., IgG, and the like), while the remainder of the chain(s) is(are) identical with or homologous to corresponding sequences in antibodies derived from another species or belonging to another antibody class or subclass, as well as fragments of such antibodies, so long as they exhibit the desired biological activity. See U.S. Pat. No. 4,816,567; Morrison et al., *Proc. Nat'l Acad. Sci. USA,* 81:6851-55 (1984). Chimeric antibodies of interest herein may include, for example, those comprising Fc domains from other immunoglobulin subtypes having shorter or longer circulating plasma half lives than the corresponding non-chimeric anti-annexin A2 antibody.

Anti-annexin A2 antibodies or antigen-binding fragments thereof may also be humanized antibodies. Humanized antibodies are molecules having an antigen-binding site derived from an immunoglobulin from a non-human species, the remaining immunoglobulin-derived parts of the molecule being derived from a human immunoglobulin, in order to reduce immunogenicity of the protein. The antigen-binding site may comprise either complete variable regions fused onto human constant domains or only the complementarity determining regions (CDRs) grafted onto appropriate human framework regions in the variable domains.

Humanized antibodies can be produced, for example, by modeling the antibody variable domains and producing the antibodies using genetic engineering techniques, such as CDR grafting. A description of various techniques for the production of humanized antibodies is found, for example, in Morrison et al., (1984) *Proc. Nat'l Acad. Sci. USA* 81:6851-55; Whittle et al., (1987) *Prot. Eng.* 1:499-505; Co et al., (1990) *J. Immunol.* 148:1149-1154; Co et al., (1992) *Proc. Nat'l Acad. Sci. USA* 88:2869-2873; Carter et al., (1992) *Proc. Nat'l Acad. Sci. USA* 89:4285-4289; Routledge et al., (1991) *Eur. J. Immunol.* 21:2717-2725 and PCT Patent Publication Nos. WO 91/09967; WO 91/09968 and WO 92/113831.

Whole antibodies as described herein can be polyclonal or monoclonal. Alternatively, functional equivalents of whole antibodies, such as antigen-binding fragments in which one or more antibody domains are truncated or absent (e.g., Fv, Fab, Fab', or $F(ab)_2$ fragments), as well as genetically-engineered antibodies or antigen-binding fragments thereof, including single chain antibodies, humanized antibodies (discussed above), antibodies that can bind to more than one epitope (e.g., bi-specific antibodies), or antibodies that can bind to one or more different antigens (e.g., bi- or multi-specific antibodies), may also be used as targeting groups.

Methods of producing polyclonal antibodies that specifically or selectively bind to a particular antigen (i.e., annexin A2) are known in the art. Generally, in the production of an antibody, a suitable experimental animal, such as, for example, but not limited to, a rabbit, a sheep, a hamster, a guinea pig, a mouse, a rat, or a chicken, is exposed to an antigen against which an antibody is desired (i.e., annexin A2). Typically, an animal is immunized with an effective amount of antigen that is injected into the animal. An effective amount of antigen refers to an amount needed to induce antibody production by the animal. The animal's immune system is then allowed to respond over a pre-determined period of time. The immunization process can be repeated until the immune system is found to be producing antibodies to the antigen. In order to obtain polyclonal antibodies specific for the antigen, serum is collected from the animal that contains the desired antibodies (or in the case of a chicken, antibody can be collected from the eggs). Such serum is useful as a reagent. Polyclonal antibodies can be further purified from the serum (or eggs) by, for example, treating the serum with ammonium sulfate to precipitate the antibodies.

Methods of producing monoclonal antibodies that specifically or selectively bind to a particular antigen (i.e., annexin A2) are known in the art. For example, monoclonal antibodies may be produced according to the methodology of Kohler and Milstein (*Nature* (1975) 256:495-497). For example, B lymphocytes are recovered from the spleen (or any suitable tissue) of an immunized animal and then fused with myeloma cells to obtain a population of hybridoma cells capable of continual growth in suitable culture medium. Hybridomas producing the desired antibody are selected by testing the ability of the antibody produced by the hybridoma to bind to the desired antigen, for example in an enzyme-linked immunosorbent assay or other routine method known in the art.

A preferred method to produce antibodies described herein includes (a) administering to an animal an effective amount of a protein or peptide (e.g., an annexin A2 protein or peptide including domains thereof) to produce the antibodies and (b) recovering the antibodies. In another method, antibodies described herein are produced recombinantly. For example, once a cell line, for example a hybridoma, expressing an antibody useful for the compositions or methods described herein has been obtained, it is possible to clone therefrom the cDNA and to identify the variable region genes encoding the desired antibody, including the sequences encoding the CDRs. From there, antibodies and antigen-binding fragments as described herein may be obtained by preparing one or more replicable expression vectors containing at least the DNA sequence encoding the variable domain of the antibody heavy or light chain and optionally other DNA sequences encoding remaining portions of the heavy and/or light chains as desired, and transforming or transfecting an appropriate host cell, in which production of the antibody will occur. Suitable expression hosts include bacteria, (for example, an *E. coli* strain), fungi, (in particular yeasts, e.g., members of the genera *Pichia, Saccharomyces*, or *Kluyveromyces*) and mammalian cell lines, e.g., a non-producing myeloma cell line, such as a mouse NSO line, or CHO cells. In order to obtain efficient transcription and translation, the DNA sequence in each vector should include appropriate regulatory sequences, particularly a promoter and leader sequence operably linked to the variable domain sequence. Particular methods for producing antibodies in this way are generally well known and routinely used. For example, basic molecular biology procedures are described by Maniatis et al. (Molecular Cloning, Cold Spring Harbor Laboratory, New York, 1989); DNA sequencing can be performed as described in Sanger et al. (*Proc. Nat'l Acad. Sci. USA* (1977) 74:5463) and the Amersham International plc sequencing handbook; and site directed mutagenesis can be carried out according to the method of Kramer et al. (*Nucl. Acids Res.* (1984) 12:9441), and the Anglian Biotechnology Ltd. handbook. Additionally, there are numerous publications, including patent specifications, describing techniques suitable for the preparation of antibodies by manipulation of DNA, creation of expression vectors and transformation of appropriate cells, for example as reviewed by Mountain, A. and Adair, J. R., in Biotechnology and Genetic Engineering Reviews (ed. Tombs, M P, 10, Chapter 1, 1992, Intercept, Andover, UK).

In certain embodiments, the factor H portion of the fusion protein compositions suitable for inhibiting activity of the alternative complement pathway in the kidneys comprises homologues of human factor H protein (SEQ ID NO:3) or biologically-active fragments thereof. A homologue of a human factor H protein or biologically-active fragment thereof includes proteins which differ from a naturally occurring human factor H protein (or from a biologically-active fragment thereof) in that at least one or a few, but not limited to one or a few, amino acids have been deleted (e.g., a truncated version of the protein, such as a peptide or fragment), inserted, inverted, substituted and/or derivatized (e.g., by glycosylation, phosphorylation, acetylation, myristoylation, prenylation, palmitation, amidation and/or addition of glycosylphosphatidyl inositol). For example, a factor H homologue or biologically-active fragments thereof may have an amino acid sequence that is at least about 70% identical to the amino acid sequence of a naturally occurring human factor H or biologically-active fragments thereof (e.g., SEQ ID NO:3), for example at least about any of 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identical to the amino acid sequence of a naturally occurring human factor H (e.g., SEQ ID NO:3). In certain embodiments, a homologue of factor H (or biologically-active fragments thereof) retains all the biological activities of human factor H (or biologically-active fragments thereof), i.e., the biologically-active fragments of factor H have one or more of the following properties: (1) binding to C-reactive protein (CRP), (2) binding to C3b, (3) binding to heparin, (4) binding to sialic acid, (5) binding to endothelial cell surfaces, (6) binding to cellular integrin receptor, (7) binding to pathogens, (8) C3b co-factor activity, (9) C3b decay-acceleration activity, and (10) inhibiting the alternative complement pathway.

In certain embodiments, the factor H portion of the fusion protein compositions suitable for inhibiting activity of the alternative complement pathway in the kidneys comprises full-length factor H. In certain embodiments, the factor H portion of the fusion protein compositions suitable for inhibiting activity of the alternative complement pathway in the kidneys comprises a biologically-active fragment of factor H. In certain embodiments, the biologically-active fragment of factor H comprises the first four N-terminal SCR domains of factor H. In certain embodiments, the biologically-active fragment of factor H comprises the first five N-terminal SCR domains of factor H. In certain embodiments, the biologically-active fragment of factor H comprises the first six N-terminal SCR domains of factor H. In certain embodiments, the biologically-active fragment of factor H comprises the first eight N-terminal SCR domains of factor H. In certain embodiments, the biologically-active fragment of factor H comprises the first eighteen N-terminal SCR domains of factor H. In certain embodiments, the biologically-active fragment of factor H comprises SCRs 1 to 4 of factor H. In certain embodiments, the biologically-active fragment of factor H comprises SCRs 1 to 8 of factor H. In certain embodiments, the biologically-active fragment of factor H comprises SCRs 1 to 18 of factor H. In certain embodiments, the factor H portion of the fusion protein compositions comprises (and in certain embodiments consists of or consists essentially of) at least the first four N-terminal SCR domains of factor H, including for example, at least any of the first 5, 6, 7, 8, 9, 10, 11, 12, 13, 14, 15, 16, 17, 18 or more N-terminal SCR domains of factor H.

In certain embodiments, the factor H or biologically-active fragment thereof portion of the fusion protein composition is or is derived from a wildtype factor H. In certain embodiments, the factor H or biologically-active fragment thereof portion of the fusion protein composition is or is derived from a protective variant of factor H.

In certain embodiments, the factor H or biologically-active fragment thereof portion of the fusion protein composition lacks a heparin binding site. This can be achieved, for example, by mutation of the heparin binding site on factor H, or by selecting biologically-active factor H fragments that do not contain a heparin binding site. In certain embodiments, the factor H or biologically-active fragment thereof portion of the fusion protein composition comprises factor H or biologically-active fragments thereof having a polymorphism that is protective to age-related macular degeneration. See Hageman et al., *Proc. Nat'l Acad. Sci. USA* 102(20):7227.

In certain embodiments, the compositions are suitable for stimulating activity of the alternative complement pathway. In certain embodiments, activity of the alternative complement pathway is stimulated in the kidneys. In certain embodiments, the compositions suitable for stimulating activity of the complement pathway comprise a biologically-active fragment of factor H lacking the complement regulatory domain present in SCRs 1 to 4 of full-length factor H. Such biologically-active fragments of factor H retain the ability to bind complement protein C3 breakdown product C3d but lack the ability to inhibit alternative complement activity. In certain embodiments, the biologically-active fragment of factor H comprises (and in certain embodiments consists of or consists essentially of) at least the last sixteen C-terminal SCR domains of factor H, including for example, at least any of the last 16, 15, 14, 13, 12, 11, 10, 9, 8, 7, 6, 5, 4, 3, or 2 C-terminal SCR domains of factor H. In certain embodiments, the biologically-active fragment of factor H comprises SCRs 19 to 20 of factor H (SEQ ID NO:8).

Also encompassed herein are variants any of the compositions described herein, for example, of annexin A2 or biologically-active fragments thereof, fusion proteins comprising anti-annexin A2 antibodies or antigen-binding fragments thereof fused to DAF, factor H, MCP, CD59, CR1, mouse Crry protein or biologically-active fragments thereof, or DAF, factor H, MCP, CD59, CR1, mouse Crry protein molecules or biologically-active fragments thereof. Such variants may be: (i) variants in which one or more of the amino acid residues of the annexin A2 or biologically-active fragments thereof, fusion proteins comprising anti-annexin A2 antibodies or antigen-binding fragments thereof fused to DAF, factor H, MCP, CD59, CR1, mouse Crry protein or biologically-active fragments thereof, or factor H molecules or biologically-active fragments thereof are substituted with a conserved or non-conserved amino acid residue (preferably a conserved amino acid residue) and such substituted amino acid residue may or may not be one encoded by the genetic code; or (ii) variants in which one or more of the amino acid residues in the annexin A2 or biologically-active fragments thereof, fusion proteins comprising anti-annexin A2 antibodies or antigen-binding fragments thereof fused to DAF, factor H, MCP, CD59, CR1, mouse Crry protein or biologically-active fragments thereof, or factor H molecules or biologically-active fragments thereof includes a substituent group, or (iii) one in which the annexin A2 or biologically-active fragments thereof, fusion proteins comprising anti-annexin A2 antibodies or antigen-binding fragments thereof fused to DAF, factor H, MCP, CD59, CR1, mouse Crry protein or biologically-active fragments thereof, or factor H molecules or biologically-active fragments thereof is fused with another compound, such as a compound to increase the half-life of the composition (for example, polyethylene glycol), or (iv) one in which additional amino acids are fused to the annexin A2 or biologically-active fragments thereof, fusion proteins comprising anti-annexin A2 antibodies or antigen-binding fragments thereof fused to DAF, factor H, MCP, CD59, CR1, mouse Crry protein or biologically-active fragments thereof, or factor H molecules or biologically-active fragments thereof, such as a leader or secretory sequence or a sequence which is employed for purification of the composition, or (v) one in which the annexin A2 or biologically-active fragments thereof, fusion proteins comprising anti-annexin A2 antibodies or antigen-binding fragments thereof fused to DAF, factor H, MCP, CD59, CR1, mouse Crry protein or biologically-active fragments thereof, or factor H molecules or biologically-active fragments thereof is fused with a larger polypeptide, i.e., human albumin, an antibody or Fc, for increased duration of effect. Such variants are deemed to be within the scope of those skilled in the art from the teachings herein.

In certain embodiments, the variant of the annexin A2 or biologically-active fragments thereof, fusion proteins comprising anti-annexin A2 antibodies or antigen-binding fragments thereof fused to DAF, factor H, MCP, CD59, CR1, mouse Crry protein or biologically-active fragments thereof, or factor H molecules or biologically-active fragments thereof contains conservative amino acid substitutions (defined further below) made at one or more predicted, preferably nonessential amino acid residues. A nonessential amino acid residue is a residue that can be altered from the wild-type sequence of a protein without altering the biological activity, whereas an essential amino acid residue is required for biological activity. A conservative amino acid substitution is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

Amino acid substitutions can be introduced in annexin A2 or biologically-active fragments thereof, fusion proteins comprising anti-annexin A2 antibodies or antigen-binding fragments thereof fused to DAF, factor H, MCP, CD59, CR1, mouse Crry protein or biologically-active fragments thereof, or factor H molecules or biologically-active fragments thereof to improve the functionality of the molecule. For example, amino acid substitutions can be introduced into annexin A2 or biologically-active fragments thereof to increase binding affinity of annexin A2 for its ligand(s), to increase binding specificity of annexin A2 for its ligand(s), to increase dimerization or multimerization of annexin A2 or biologically-active fragments thereof, and to improve pharmacokinetics of the annexin A2 or biologically-active fragments thereof. Similarly, amino acid substitutions can be introduced into factor H or biologically-active fragments thereof to increase the functionality of the composition comprising anti-annexin A2 antibody or antigen-binding fragments thereof fused to factor H or biologically-active fragments thereof and to improve the pharmacokinetics of the fusion proteins.

In certain embodiments, any of the stimulatory or inhibitory compositions described herein (such as the annexin A2 protein or biologically-active fragments thereof, the fusion proteins comprising anti-annexin A2 antibodies or antigen-binding fragments thereof fused to DAF, factor H, MCP, CD59, CR1, mouse Crry protein or biologically-active fragments thereof, or factor H molecules or biologically-active fragments thereof) is fused with another compound, such as a compound to increase the half-life of the polypeptide and/or to reduce potential immunogenicity of the polypeptide (for example, polyethylene glycol, or PEG). PEG can be used to impart water solubility, size, slow rate of kidney clearance, and reduced immunogenicity to the fusion protein. See, e.g., U.S. Pat. No. 6,214,966. In the case of PEGylations, the fusion of any of the compositions described herein (such as the annexin A2 protein or biologically-active fragments thereof, the fusion proteins comprising anti-annexin A2 antibodies or antigen-binding fragments thereof fused to DAF, factor H, MCP, CD59, CR1, mouse Crry protein or biologically-active fragments thereof, or factor H molecules or biologically-active fragments thereof) to PEG can be accomplished by any means known to one skilled in the art. For example, PEGylation can be accomplished by first introducing a cysteine mutation into the desired composition, followed by site-specific derivatization with PEG-maleimide. The cysteine can be added to the C-terminus of the composition. See, e.g., Tsutsumi et al., (2000) *Proc. Nat'l Acad. Sci. USA* 97(15):8548-8553. Another modification which can be made to any of the compositions described herein (such as the annexin A2 protein or biologically-active fragments thereof, fusion proteins comprising anti-annexin A2 antibodies or antigen-binding fragments thereof fused to DAF, factor H, MCP, CD59, CR1, mouse Crry protein or biologically-active fragments thereof, or factor H molecules or biologically-active fragments thereof) involves biotinylation. In certain instances, it may be useful to have the composition biotinylated so that it can readily react with streptavidin. Methods for biotinylation of proteins are well known in the art. Additionally, chondroitin sulfate can be linked with any of the compositions described herein.

Any of the compositions described herein (such as the annexin A2 protein or biologically-active fragments thereof, the fusion proteins comprising anti-annexin A2 antibodies or antigen-binding fragments thereof fused to DAF, factor H, MCP, CD59, CR1, mouse Crry protein or biologically-active fragments thereof, or factor H molecules or biologically-active fragments thereof) may also be modified to include an immunologically active domain, such as an antibody epitope or other tag, to facilitate targeting or purification of the polypeptide. The use of 6xHis and GST (glutathione-S-transferase) as tags is well known. Inclusion of a cleavage site at or near the fusion junction will facilitate removal of the extraneous polypeptide after purification. Other amino acid sequences that may be included in the compositions described herein include functional domains, such as active sites from enzymes such as a hydrolase, glycosylation domains, and cellular targeting signals.

Variants of the compositions described herein include polypeptides having an amino acid sequence sufficiently similar to the amino acid sequence of the annexin A2 protein or biologically-active fragments thereof, the fusion proteins comprising anti-annexin A2 antibodies or antigen-binding fragments thereof fused to DAF, factor H, MCP, CD59, CR1, mouse Crry protein or biologically-active fragments thereof, or factor H molecules or biologically-active fragments thereof. The term sufficiently similar means a first amino acid sequence that contains a sufficient or minimum number of identical or equivalent amino acid residues relative to a second amino acid sequence such that the first and second amino acid sequences have a common structural domain and/or common functional activity. For example, amino acid sequences that contain a common structural domain that is at least about 45%, preferably about 75% through 98%, identical are defined herein as sufficiently similar. Variants include variants of fusion proteins encoded by a polynucleotide that hybridizes to a polynucleotide as described herein or a complement thereof under stringent conditions. Stringent hybridization conditions are known to those skilled in the art, and are described, for example, in references such as MOLECULAR CLONING, by Sambrook and Russell. 3d ed., Cold Spring Harbor Press, Cold Spring Harbor, N.Y. (2001). Such variants generally retain the functional activity of the compositions described herein. Libraries of fragments of the polynucleotides can be used to generate a variegated population of fragments for screening and subsequent selection. For example, a library of fragments can be generated by treating a double-stranded PCR fragment of a polynucleotide with a nuclease under conditions wherein nicking occurs only about once per molecule, denaturing the double-stranded DNA, renaturing the DNA to form double-stranded DNA which can include sense/antisense pairs from different nicked products, removing single-stranded portions from reformed duplexes by treatment with S1 nuclease, and ligating the resulting fragment library into an expression vector. By this method, one can derive an expression library that encodes N-terminal and internal fragments of various sizes of the compositions described herein.

In certain embodiments, any of the compositions described herein, particularly the annexin A2 protein or biologically-active fragments thereof, the fusion proteins comprising anti-annexin A2 antibodies or antigen-binding fragments thereof fused to DAF, factor H, MCP, CD59, CR1, mouse Crry protein or biologically-active fragments thereof, or factor H molecules or biologically-active fragments thereof, are fused at their N-terminus to a signal peptide. Such signal peptides guide secretion of the molecules, facilitating purification from culture medium. Suitable signal peptides include, for example, the signal peptide of the CD5 protein (such as signal peptide of the human CD5 protein MPMGSLQPLATLYLLGMLVAS, SEQ ID NO:11). In certain embodiments, the signal peptide of the CR2 protein is used. For example, in certain embodiments, the signal peptide of the human CR2 protein (MGAAGLLGVFLALVAPG, SEQ ID NO:13 or MGAAGLLGVFLALVAPGVLG, SEQ ID NO:15) is used.

Any of the compositions described herein may be made by chemical synthesis methods, or by recombinant methods, for example, by preparing a polynucleotide encoding human annexin A2 or biologically-active fragments thereof, or polynucleotides encoding an anti-annexin A2 antibody (light and heavy chains) and DAF, factor H, MCP, CD59, CR1, mouse Crry protein molecules or biologically-active fragments thereof (with or without a linker sequence), and introducing the resulting polynucleotide molecule(s) into a vector for transfecting host cells that are capable of expressing the molecule. Chemical synthesis, especially solid phase synthesis, is preferred for short peptides or those containing unnatural or unusual amino acids such as D-tyrosine, ornithine, and the like. Recombinant procedures are preferred for longer polypeptides. Recombinant preparations of any of the compositions described herein can be isolated in vitro by routine protein purification methods. The compositions described and provided herein can also be provided in situ by introduction of a gene therapy system to the tissue of interest which then expresses the desired composition.

Recombinant DNA techniques for making the compositions described and provided herein involve, in simplified form, taking a polynucleotide encoding the desired composition (e.g., the annexin A2 protein or biologically-active fragments thereof, the fusion proteins comprising anti-annexin A2 antibodies or antigen-binding fragments thereof fused to DAF, factor H, MCP, CD59, CR1, mouse Crry protein or biologically-active fragments thereof, or factor H molecules or biologically-active fragments thereof), inserting it into an appropriate vector, inserting the vector into an appropriate host cell, and recovering or otherwise isolating the protein produced thereby.

Provided herein are polynucleotides that encode human annexin A2, the light and heavy chains of an anti-annexin A2 antibody, and human factor H. Such polynucleotides may be used to deliver and express the complement stimulatory and inhibitory compositions described herein. For example, in certain embodiments, there are provided polynucleotides encoding a fusion protein comprising an anti-annexin A2 antibody or antigen-binding fragment thereof and factor H or a biologically-active fragment thereof. In certain embodiments, the polynucleotides further comprise a sequence encoding a signal peptide operably linked at the 5' end of the sequence encoding the fusion protein. Exemplary nucleotide sequences of signal peptides are provided in SEQ ID NOs: 12, 14, and 16.

Also provided herein are expression vectors comprising polynucleotides expressing any of the compositions described herein. The expression vector can be used to direct expression of any of the compositions described herein in vitro or in vivo. The vector may include any element necessary to establish a conventional function of a vector, for example, a transcription promoter or terminator, a selectable marker, and an origin of replication. The promoter can be constitutive or regulative, and is selected from, for example, promoters of genes for galactokinase (GAL1), uridylyltransferase (GALT), epimerase (GAL10), phosphoglycerate kinase (PGK), glyceraldehydes-3-phosphate dehydrogenase (GPD), alcohol dehydrogenase (ADH), and the like.

Many expression vectors are known to those of skill in the art. For example, *E. coli* may be transformed using pBR322, a plasmid derived from an *E. coli* species (Mandel et al., *J. Mol. Biol.,* 53:154(1970)). Plasmid pBR322 contains genes for ampicillin and tetracycline resistance, and thus provides easy means for selection. Other vectors include different features such as different promoters, which are often important in expression. For example, plasmids pKK223-3 (Pharmacia Fine Chemicals, Uppsala, Sweden), pKK233-2 (Clontech, Palo Alto, Calif., USA), and pGEM1 (Promega Biotech, Madison, Wis., USA), are all commercially available. Other vectors that are useful as described herein include, but are not limited to, pET21a (Studier et al., *Methods Enzymol.* (1990) 185: 60-89), pR1T5, and pR1T2T (Pharmacia Biotechnology), and pB0475 (Cunningham et al., *Science,* 243: 1330-1336 (1989); U.S. Pat. No. 5,580,723). Mammalian expression vectors may contain non-transcribed elements such as an origin of replication, promoter and enhancer, and 5' or 3' nontranslated sequences such as ribosome binding sites, a polyadenylation site, acceptor site and splice donor, and transcriptional termination sequences. Promoters for use in mammalian expression vectors usually are for example viral promoters such as Polyoma, Adenovirus, HTLV, Simian Virus 40 (SV 40), and human cytomegalovirus (CMV). Vectors can also be constructed using standard techniques by combining the relevant traits of the vectors described above.

Also provided are host cells (such as isolated cells, transient cell lines, and stable cell lines) for expressing any of the compositions described herein. The host cell may be prokaryotic or eukaryotic. Exemplary prokaryote host cells include *E. coli* K12 strain 294 (ATCC No. 31446), *E. coli* B, *E. coli* X1776 (ATCC No. 31537), *E. coli* W3110 (F-, gamma-, prototrophic/ATCC No. 27325), *Bacilli* such as *B. subtilis*, and other Enterobacteriaceae such as *Salmonella typhimurium* or *Serratia marcesans* and various *Pseudomonas* species. One suitable prokaryotic host cell is *E. coli* BL21 (Stratagene Corp., La Jolla, Calif., USA), which is deficient in the OmpT and Lon proteases, which may interfere with isolation of intact recombinant proteins, and useful with T7 promoter-driven vectors, such as the pET vectors. Another suitable prokaryote is *E. coli* W3110 (ATCC No. 27325). When expressed by prokaryotes the peptides typically contain an N-terminal methionine or a formyl-methionine ("f-Met") and are not glycosylated. In the case of fusion proteins, the N-terminal methionine or f-Met resides on the amino terminus of the expressed protein or of the signal sequence of the expressed protein. These examples are, of course, intended to be illustrative rather than limiting.

In addition to prokaryotes, eukaryotic microbes such as filamentous fungi or yeast are suitable cloning or expression hosts for fusion-protein-encoding vectors. *Saccharomyces*

*cerevisiae* is a commonly used lower eukaryotic host microorganism. Others include *Schizosaccharomyces pombe* (Beach and Nurse, *Nature,* 290: 140 (1981); EP 139,383 published 2 May 1985); *Kluyveromyces* hosts (U.S. Pat. No. 4,943,529; Fleer et al., *Bio/Technology* (1991) 9:968-975) such as, e.g., *K. lactis* (MW98-8C, CBS683, CBS4574; Louvencourt et al., *J. Bacteriol.,* 154(2):737-742 (1983)), *K. fragilis* (ATCC 12,424), *K. bulgaricus* (ATCC No. 16,045), *K. wickeramii* (ATCC No. 24,178), *K. waltii* (ATCC No. 56,500), *K. drosophilarum* (ATCC No. 36,906; Van den Berg et al., Bio/Technology (1990) 8:135), *K. thermotolerans*, and *K. marxianus yarrowia* (EP 402,226); *Pichia pastoris* (EP 183,070; Sreekrishna et al., *J. Basic Microbiol.* (1988) 28:265-278); *Candida; Trichoderma reesia* (EP 244, 234); *Neurospora crassa* (Case et al, *Proc. Nat'l Acad. Sci. USA,* (1979) 76:5259-5263); *Schwanniomyces*, such as *Schwanniomyces occidentalis* (EP 394,538 published 31 Oct. 1990); and filamentous fungi such as, e.g., *Neurospora, Penicillium, Tolypocladium* (WO 91/00357 published 10 Jan. 1991), and *Aspergillus* hosts such as *A. nidulans* (Ballance et al., *Biochem. Biophys. Res. Commun.* (1983) 112: 284-289; Tilburn et al., *Gene* (1983) 26:205-221; Yelton et al., *Proc. Nat'l Acad. Sci. USA* (1984) 81: 1470-1474) and *A. niger* (Kelly and Hynes, *EMBO J.* (1985) 4:475-479). Methylotropic yeasts are suitable herein and include, but are not limited to, yeast capable of growth on methanol selected from the genera consisting of *Hansenula, Candida, Kloeckera, Pichia, Saccharomyces, Torulopsis*, and *Rhodotorula*. A list of specific species that are exemplary of this class of yeasts may be found in C. Anthony, The Biochemistry of Methylotrophs, 269 (1982). Host cells also include insect cells such as *Drosophila* S2 and *Spodoptera* Sf9, as well as plant cells.

Examples of useful mammalian host cell lines include, but are not limited to, HeLa, Chinese hamster ovary (CHO), COS-7, L cells, C127, 3T3, BHK, CHL-1, NSO, HEK293, WI38, BHK, C127 or MDCK cell lines. Another exemplary mammalian cell line is CHL-1. When CHL-1 is used, hygromycin is included as a eukaryotic selection marker. CHL-1 cells are derived from RPMI 7032 melanoma cells, a readily available human cell line. Cells suitable for use as described herein are commercially available from the American Type Culture Collection ("ATCC"; Manassas, Va., USA).

In certain embodiments, the host cell is a non-human host cell. In certain embodiments, the host cell is a CHO cell. In certain embodiments, the host cell is a 293 cell.

Any of the compositions described herein and prepared according to recombinant methods known in the art can be isolated by a variety of methods known in the art. In certain embodiments, when the compositions comprise a secretory peptide operably linked to a polynucleotide encoding the desired composition and are thus secreted into the growth medium, the molecule can be purified directly from the medium. If the fusion protein is not secreted, it can be isolated from cell lysates. Cell disruption can be done by any conventional method, including freeze-thaw cycling, sonication, mechanical disruption, or use of cell lysing and/or chaotropic agents. The desired composition molecules can be purified from cell lysates by various methods. These include, but are not limited to, immunoaffinity chromatography, reverse phase chromatography, cation exchange chromatography, anion exchange chromatography, hydrophobic interaction chromatography, gel filtration chromatography, and HPLC. For example, a fusion protein comprising an anti-annexin A2 antibody or antigen-binding fragment thereof and factor H or a biologically-active fragment thereof can be purified by immunoaffinity chromatography using an antibody that recognizes the factor H portion or an antibody that recognizes the Fc portion of the anti-annexin A2 antibody, or both. In certain embodiments, an antibody recognizing the first four N-terminal SCR domains of factor H is used for purifying the fusion protein. In certain embodiments, the desired composition is purified by ion exchange chromatography.

The polypeptide may or may not be properly folded when expressed as a fusion protein. These factors determine whether the fusion protein must be denatured and refolded, and if so, whether these procedures are employed before or after cleavage. When denaturing and refolding are needed, typically the peptide is treated with a chaotrope, such a guanidine HCl, and is then treated with a redox buffer, containing, for example, reduced and oxidized dithiothreitol or glutathione at the appropriate ratios, pH, and temperature, such that the peptide is refolded to its native structure.

Any of the compositions described herein may also contain a tag (such as a cleavable tag) for purification. This tag can be fused to the C-terminus or N-terminus of the composition, and can be used to facilitate protein purification.

In certain embodiments, the compositions described herein could be synthesized de novo in whole or in part, using chemical methods well known in the art. For example, the component amino acid sequences can be synthesized by solid phase techniques, cleaved from the resin, and purified by preparative high performance liquid chromatography followed by chemical linkage to form a desired polypeptide. The composition of the synthetic peptides may be confirmed by amino acid analysis or sequencing.

The purified compositions described herein can be assayed for their desired properties (i.e., the ability to bind annexin A2, factor H, or breakdown products of complement protein C3, or the ability to inhibit activity of the alternative complement pathway) using standard in vitro or in vivo assays. For example, binding of a biologically-active factor H fragment to a breakdown product of complement protein C3 can be determined by surface plasmon resonance. By way of example, kinetic analysis of the interaction of a biologically-active fragment of factor H comprising SCRs 1 to 4 with C3dg-biotin can be performed using surface plasmon resonance ("SPR") measurements made on a BIAcore 3000 instrument (Biacore AB, Uppsala, Sweden). Human C3dg-biotin can be bound to the surface of BIAcore streptavidin sensor chips by injecting C3dg-biotin over the surface of one flow cell of the chip. Binding can be evaluated over a range of factor H fragment concentrations. Association of the factor H fragment with the ligand can be monitored for a certain period of time (such as 120 seconds), after which the complex is allowed to dissociate in the presence of buffer only for an additional period of time (such as 120 seconds). Binding of biologically-active factor H fragments to C3dg-immobilized flow cells can be corrected for binding to control flow cells. Binding data can be fitted to a 1:1 Langmuir binding model using BIAevaluation Version 3.1 software (BIAcore) and evaluated for best fit. The kinetic dissociation profiles obtained can be used to calculate on and off rates ($k_a$ and $k_d$) and affinity constants ($K_D$) using the BIAevaluation Version 3.1 program. Other assay methods for ligand binding are known in the art and can also be used.

An in vitro zymosan complement assay can be used to determine complement inhibitory activity of the fusion protein compositions comprising an anti-annexin A2 antibody or antigen-binding fragment thereof fused to factor H or a biologically-active fragment thereof, or to determine complement stimulatory activity of the biologically-active fragments of factor H described herein. Lysis of rabbit erythrocytes by serum in Mg-EGTA is another measure of activity that can be used. Lysis in Mg-EGTA of human or sheep erythrocytes that have had sialic acid removed provides for additional measures of activity.

Methods of Identifying Factor H-binding Proteins

As discussed above, inhibition of alternative complement pathway activity on cell surfaces by factor H requires that factor H properly bind to the cell surface. Thus, activation of the alternative pathway on a particular surface is strongly influenced by the affinity of factor H for that surface. Certain tissues or cell types require factor H to regulate alternative pathway activation on their surface. In some cases, different binding regions of the factor H protein may be necessary for complement regulation on those tissues or cell types. In others, the binding of factor H to surfaces in particular tissues may be affected by as-yet-unidentified proteins. Identification of putative tissue-specific binding partners of factor H may provide potential mechanisms for modulating, i.e., stimulating or inhibiting, activity of the alternative complement pathway in different tissues. Thus, in another aspect, methods of identifying factor H-binding proteins are provided.

In certain embodiments, the methods of identifying factor H-binding proteins comprise (1) incubating full-length factor H or a biologically-active fragment thereof with a cell lysate prepared from a target tissue, cell type, or cell line under conditions for a time sufficient to permit putative factor H ligands to bind full-length factor H or a biologically-active fragment thereof; (2) purifying the complex comprising bound factor H or a biologically-active fragment thereof and one or more factor H-binding proteins; (3) separating the factor H-binding proteins by two dimensional polyacrylamide gel electrophoresis; and (4) identifying factor H-binding proteins. Full-length factor H can be obtained by purification from plasma, or may be prepared recombinantly, by expression in eukaryotic cells followed by purification from culture medium or lysed cells.

The cell lysate can be prepared from any desired tissue that can be obtained from an individual, for example, renal, hepatic, pulmonary, bone marrow, lymph node, cardiac muscle, skeletal muscle, smooth muscle, epithelial, brain, or pancreatic tissue and the like. The cell lysate can also be prepared from cell lines of any desired origin, for example, stem cells, including embryonic stem cells, renal, hepatic, pulmonary, cardiac muscle, skeletal muscle, smooth muscle, epithelial, brain, B or T lymphocyte, lymph nodes, or pancreatic cell lines and the like. Those skilled in the art can easily select an appropriate tissue or cell line to use with the methods provided herein, based on the site of alternative complement activation being studied.

In certain embodiments, the full-length factor H further comprises a tag to facilitate purification, both of full-length factor H or biologically-active fragments thereof and of factor H or biologically-active fragments thereof bound to one or more factor H binding proteins. Various tags commonly used to facilitate purification are known to those skilled in the art. In certain embodiments, the tag to facilitate purification is a poly-histidine tag, a maltose-binding protein epitope, or biotin. In certain embodiments, the complex comprising bound factor H is purified via chromatography over a matrix comprising streptavidin, nickel-NTA-agarose, or an anti-maltose binding protein antibody. In certain embodiments, the complexes are purified via streptavidin-labeled magnetic beads. In certain embodiments, the factor H binding proteins are identified by mass spectrometry. In certain embodiments, the mass spectrometry is tandem mass spectrometry ("MS-MS"). In certain embodiments, the mass spectrometry is matrix-assisted laser desorption ionized time-of-flight ("MALDI-TOF") mass spectrometry. In certain embodiments, labeled factor H is used in Far Western blot analysis to identify specific binding proteins that are further characterized by antibody-directed Western blot analysis or other methods known to those skilled in the art.

Pharmaceutical Compositions

Also provided herein are pharmaceutical compositions comprising annexin A2 or biologically-active fragments thereof, fusion proteins comprising anti-annexin A2 antibodies or antigen-binding fragments thereof fused to DAF, factor H, MCP, CD59, CR1, mouse Crry protein or biologically-active fragments thereof, or factor H or biologically-active fragments thereof and a pharmaceutically acceptable carrier.

The pharmaceutical compositions may be suitable for a variety of modes of administration as described herein, including, for example, systemic or localized administration. The pharmaceutical compositions described herein can be in the form of injectable solutions. The pharmaceutical compositions described herein can be packaged in single unit dosages or in multidosage forms.

In certain embodiments, the pharmaceutical compositions comprise annexin A2 or biologically-active fragments thereof and a pharmaceutically acceptable carrier suitable for administration to an individual. In certain embodiments, the pharmaceutical compositions comprise fusion proteins comprising an anti-annexin A2 antibody or antigen-binding fragment thereof fused to DAF, factor H, MCP, CD59, CR1, mouse Crry protein or biologically-active fragments thereof and a pharmaceutically acceptable carrier suitable for administration to an individual.

In certain embodiments, the pharmaceutical composition comprises a fusion protein comprising an anti-annexin A2 antibody or antigen-binding fragment thereof fused to full-length human DAF (SEQ ID NO:17) and a pharmaceutically acceptable carrier suitable for administration to an individual. In certain embodiments, the pharmaceutical composition comprises a fusion protein comprising an anti-annexin A2 antibody or antigen-binding fragment thereof fused to a biologically-active fragment of human DAF comprising full-length human DAF lacking its GPI anchor (amino acids 35-353 of SEQ ID NO:17) and a pharmaceutically acceptable carrier suitable for administration to an individual. In certain embodiments, the pharmaceutical composition comprises a fusion protein comprising an anti-annexin A2 antibody or antigen-binding fragment thereof fused to a biologically-active fragment of human DAF comprising SCRs 1-4 of human DAF (amino acids 35-285 of SEQ ID NO:17) and a pharmaceutically acceptable carrier suitable for administration to an individual.

In certain embodiments, the pharmaceutical composition comprises a fusion protein comprising an anti-annexin A2 antibody or antigen-binding fragment thereof fused to full-length factor H and a pharmaceutically acceptable carrier suitable for administration to an individual. In certain embodiments, the pharmaceutical composition comprises a fusion protein comprising an anti-annexin A2 antibody or antigen-binding fragment thereof fused to a biologically-active fragment of factor H comprising SCRs 1 to 4 and a pharmaceutically acceptable carrier suitable for administration to an individual. In certain embodiments, the pharmaceutical composition comprises a fusion protein comprising an anti-annexin A2 antibody or antigen-binding fragment thereof fused to a biologically-active fragment of factor H comprising SCRs 1 to 8 and a pharmaceutically acceptable carrier suitable for administration to an individual. In certain embodiments, the pharmaceutical composition comprises a fusion protein comprising an anti-annexin A2 antibody or antigen-binding fragment thereof fused a biologically-active fragment of factor H comprising SCRs 1 to 18 and a pharmaceutically acceptable carrier suitable for administration to an individual. In certain embodiments, the pharmaceutical compositions comprise biologically-active fragments of factor H lacking the complement regulatory domain in SCRs 1 to 4 of full-length factor H and a pharmaceutically acceptable carrier suitable for administration to an individual. In certain embodiments, the biologically-active fragment of factor H comprises SCRs 19 to 20 of factor H and a pharmaceutically acceptable carrier suitable for administration to an individual.

In certain embodiments, the pharmaceutical composition comprises a fusion protein comprising an anti-annexin A2 antibody or antigen-binding fragment thereof fused to full-length human MCP (SEQ ID NO:19) and a pharmaceutically acceptable carrier suitable for administration to an individual. In certain embodiments, the pharmaceutical composition comprises a fusion protein comprising an anti-annexin A2 antibody or antigen-binding fragment thereof fused to a biologically-active fragment of human MCP comprising the extracellular domain of human MCP (amino acids 35-343 of SEQ ID NO:19) and a pharmaceutically acceptable carrier suitable for administration to an individual. In certain embodiments, the pharmaceutical composition comprises a fusion protein comprising an anti-annexin A2 antibody or antigen-binding fragment thereof fused to a biologically-active fragment of human MCP comprising SCRs 1 to 4 of human MCP (amino acids 35-285 of SEQ ID NO:19) and a pharmaceutically acceptable carrier suitable for administration to an individual.

In certain embodiments, the pharmaceutical composition comprises a fusion protein comprising an anti-annexin A2 antibody or antigen-binding fragment thereof fused to full-length human CD59 (SEQ ID NO:21) and a pharmaceutically acceptable carrier suitable for administration to an individual. In certain embodiments, the pharmaceutical composition comprises a fusion protein comprising an anti-annexin A2 antibody or antigen-binding fragment thereof fused to a biologically-active fragment of human CD59 comprising the extracellular domain of human CD59 lacking a GPI anchor and/or the amino acid to which it is attached (i.e., Asn-102)(amino acids 26-102 of SEQ ID NO:21) and a pharmaceutically acceptable carrier suitable for administration to an individual.

In certain embodiments, the pharmaceutical composition comprises a fusion protein comprising an anti-annexin A2 antibody or antigen-binding fragment thereof fused to full-length human CR1 (SEQ ID NO:23) and a pharmaceutically acceptable carrier suitable for administration to an individual. In certain embodiments, the pharmaceutical composition comprises a fusion protein comprising an anti-annexin A2 antibody or antigen-binding fragment thereof fused to a biologically-active fragment of human CR1 comprising the complete extracellular domain of human CR1 (SCRs 1 to 30)(amino acids 42-1971 of SEQ ID NO:23) and a pharmaceutically acceptable carrier suitable for administration to an individual. In certain embodiments, the pharmaceutical composition comprises a fusion protein comprising an anti-annexin A2 antibody or antigen-binding fragment thereof fused to a biologically active fragment of full-length human CR1 comprising SCRs 1 to 4 (amino acids 42-295 of SEQ ID NO:23) and a pharmaceutically acceptable carrier suitable for administration to an individual. In certain embodiments, the pharmaceutical composition comprises a fusion protein comprising an anti-annexin A2 antibody or antigen-binding fragment thereof fused to a biologically active fragment of full-length human CR1 comprising SCRs 1 to 11 (amino acids 42-745 of SEQ ID NO:23) and a pharmaceutically acceptable carrier suitable for administration to an individual. In certain embodiments, the pharmaceutical composition comprises a fusion protein comprising an anti-annexin A2 antibody or antigen-binding fragment thereof fused to a biologically active fragment of full-length human CR1 comprising SCRs 1 to 18 (amino acids 42-1195 of SEQ ID NO:23) and a pharmaceutically acceptable carrier suitable for administration to an individual.

In certain embodiments, the pharmaceutical composition comprises a fusion protein comprising an anti-annexin A2 antibody or antigen-binding fragment thereof fused to full-length mouse Crry protein (SEQ ID NO:25) and a pharmaceutically acceptable carrier suitable for administration to an individual. In certain embodiments, the pharmaceutical composition comprises a fusion protein comprising an anti-annexin A2 antibody or antigen-binding fragment thereof fused to a biologically-active fragment of full-length mouse Crry protein comprising the complete extracellular domain of mouse Crry protein (amino acids 41-405 of SEQ ID NO:25) and a pharmaceutically acceptable carrier suitable for administration to an individual. In certain embodiments, the pharmaceutical composition comprises a fusion protein comprising an anti-annexin A2 antibody or antigen-binding fragment thereof fused to a biologically-active fragment of full-length mouse Crry protein comprising SCRs 1 to 5 of mouse Crry protein (amino acids 83-400 of SEQ ID NO:25) and a pharmaceutically acceptable carrier suitable for administration to an individual.

In certain embodiments, the pharmaceutical compositions comprise annexin A2 or biologically-active fragments thereof and a pharmaceutically acceptable carrier suitable for oral administration to an individual. In certain embodiments, the pharmaceutical compositions comprise fusion proteins comprising an anti-annexin A2 antibody or antigen-binding fragment thereof fused to DAF, factor H, MCP, CD59, CR1, mouse Crry protein or biologically-active fragments thereof and a pharmaceutically acceptable carrier suitable for oral administration to an individual.

In certain embodiments, the pharmaceutical composition comprises a fusion protein comprising an anti-annexin A2 antibody or antigen-binding fragment thereof fused to full-length human DAF (SEQ ID NO:17) and a pharmaceutically acceptable carrier suitable for oral administration to an individual. In certain embodiments, the pharmaceutical composition comprises a fusion protein comprising an anti-annexin A2 antibody or antigen-binding fragment thereof fused to a biologically-active fragment of human DAF comprising full-length human DAF lacking its GPI anchor (amino acids 35-353 of SEQ ID NO:17) and a pharmaceutically acceptable carrier suitable for oral administration to an individual. In certain embodiments, the pharmaceutical composition comprises a fusion protein comprising an anti-annexin A2 antibody or antigen-binding fragment thereof fused to a biologically-active fragment of human DAF comprising SCRs 1-4 of human DAF (amino acids 35-285 of SEQ ID NO:17) and a pharmaceutically acceptable carrier suitable for oral administration to an individual.

In certain embodiments, the pharmaceutical composition comprises a fusion protein comprising an anti-annexin A2 antibody or antigen-binding fragment thereof fused to full-length factor H and a pharmaceutically acceptable carrier suitable for oral administration to an individual. In certain embodiments, the pharmaceutical composition comprises a fusion protein comprising an anti-annexin A2 antibody or antigen-binding fragment thereof fused to a biologically-active fragment of factor H comprising SCRs 1 to 4 and a pharmaceutically acceptable carrier suitable for oral administration to an individual. In certain embodiments, the pharmaceutical composition comprises a fusion protein comprising an anti-annexin A2 antibody or antigen-binding fragment thereof fused to a biologically-active fragment of factor H comprising SCRs 1 to 8 and a pharmaceutically acceptable carrier suitable for oral administration to an individual. In certain embodiments, the pharmaceutical composition comprises a fusion protein comprising an anti-annexin A2 antibody or antigen-binding fragment thereof fused a biologically-active fragment of factor H comprising SCRs 1 to 18 and a pharmaceutically acceptable carrier suitable for oral administration to an individual. In certain embodiments, the pharmaceutical compositions comprise biologically-active fragments of factor H lacking the complement regulatory domain in SCRs 1 to 4 of full-length factor H and a pharmaceutically acceptable carrier suitable for oral administration to an individual. In certain embodiments, the biologically-active fragment of factor H comprises SCRs 19 to 20 of factor H and a pharmaceutically acceptable carrier suitable for oral administration to an individual.

In certain embodiments, the pharmaceutical composition comprises a fusion protein comprising an anti-annexin A2 antibody or antigen-binding fragment thereof fused to full-length human MCP (SEQ ID NO:19) and a pharmaceutically acceptable carrier suitable for oral administration to an individual. In certain embodiments, the pharmaceutical composition comprises a fusion protein comprising an anti-annexin A2 antibody or antigen-binding fragment thereof fused to a biologically-active fragment of human MCP comprising the extracellular domain of human MCP (amino acids 35-343 of SEQ ID NO:19) and a pharmaceutically acceptable carrier suitable for oral administration to an individual. In certain embodiments, the pharmaceutical composition comprises a fusion protein comprising an anti-annexin A2 antibody or antigen-binding fragment thereof fused to a biologically-active fragment of human MCP comprising SCRs 1 to 4 of human MCP (amino acids 35-285 of SEQ ID NO:19) and a pharmaceutically acceptable carrier suitable for oral administration to an individual.

In certain embodiments, the pharmaceutical composition comprises a fusion protein comprising an anti-annexin A2 antibody or antigen-binding fragment thereof fused to full-length human CD59 (SEQ ID NO:21) and a pharmaceutically acceptable carrier suitable for oral administration to an individual. In certain embodiments, the pharmaceutical composition comprises a fusion protein comprising an anti-annexin A2 antibody or antigen-binding fragment thereof fused to a biologically-active fragment of human CD59 comprising the extracellular domain of human CD59 lacking a GPI anchor and/or the amino acid to which it is attached (i.e., Asn-102)(amino acids 26-102 of SEQ ID NO:21) and a pharmaceutically acceptable carrier suitable for oral administration to an individual.

In certain embodiments, the pharmaceutical composition comprises a fusion protein comprising an anti-annexin A2 antibody or antigen-binding fragment thereof fused to full-length human CR1 (SEQ ID NO:23) and a pharmaceutically acceptable carrier suitable for oral administration to an individual. In certain embodiments, the pharmaceutical composition comprises a fusion protein comprising an anti-annexin A2 antibody or antigen-binding fragment thereof fused to a biologically-active fragment of human CR1 comprising the complete extracellular domain of human CR1 (SCRs 1 to 30)(amino acids 42-1971 of SEQ ID NO:23) and a pharmaceutically acceptable carrier suitable for oral administration to an individual. In certain embodiments, the pharmaceutical composition comprises a fusion protein comprising an anti-annexin A2 antibody or antigen-binding fragment thereof fused to a biologically active fragment of full-length human CR1 comprising SCRs 1 to 4 (amino acids 42-295 of SEQ ID NO:23) and a pharmaceutically acceptable carrier suitable for oral administration to an individual. In certain embodiments, the pharmaceutical composition comprises a fusion protein comprising an anti-annexin A2 antibody or antigen-binding fragment thereof fused to a biologically active fragment of full-length human CR1 comprising SCRs 1 to 11 (amino acids 42-745 of SEQ ID NO:23) and a pharmaceutically acceptable carrier suitable for oral administration to an individual. In certain embodiments, the pharmaceutical composition comprises a fusion protein comprising an anti-annexin A2 antibody or antigen-binding fragment thereof fused to a biologically active fragment of full-length human CR1 comprising SCRs 1 to 18 (amino acids 42-1195 of SEQ ID NO:23) and a pharmaceutically acceptable carrier suitable for oral administration to an individual.

In certain embodiments, the pharmaceutical composition comprises a fusion protein comprising an anti-annexin A2 antibody or antigen-binding fragment thereof fused to full-length mouse Crry protein (SEQ ID NO:25) and a pharmaceutically acceptable carrier suitable for oral administration to an individual. In certain embodiments, the pharmaceutical composition comprises a fusion protein comprising an anti-annexin A2 antibody or antigen-binding fragment thereof fused to a biologically-active fragment of full-length mouse Crry protein comprising the complete extracellular domain of mouse Crry protein (amino acids 41-405 of SEQ ID NO:25) and a pharmaceutically acceptable carrier suitable for oral administration to an individual. In certain embodiments, the pharmaceutical composition comprises a fusion protein comprising an anti-annexin A2 antibody or antigen-binding fragment thereof fused to a biologically-active fragment of full-length mouse Crry protein comprising SCRs 1 to 5 of mouse Crry protein (amino acids 83-400 of SEQ ID NO:25) and a pharmaceutically acceptable carrier suitable for oral administration to an individual.

In certain embodiments, the pharmaceutical compositions comprise annexin A2 or biologically-active fragments thereof and a pharmaceutically acceptable carrier suitable for intravenous injection into an individual. In certain embodiments, the pharmaceutical compositions comprise fusion proteins comprising an anti-annexin A2 antibody or antigen-binding fragment thereof fused to DAF, factor H, MCP, CD59, CR1, mouse Crry protein or biologically-active fragments thereof and a pharmaceutically acceptable carrier suitable for intravenous injection into an individual.

In certain embodiments, the pharmaceutical composition comprises a fusion protein comprising an anti-annexin A2 antibody or antigen-binding fragment thereof fused to full-length human DAF (SEQ ID NO:17) and a pharmaceutically acceptable carrier suitable for intravenous injection into an individual. In certain embodiments, the pharmaceutical composition comprises a fusion protein comprising an anti-annexin A2 antibody or antigen-binding fragment thereof fused to a biologically-active fragment of human DAF comprising full-length human DAF lacking its GPI anchor (amino acids 35-353 of SEQ ID NO:17) and a pharmaceutically acceptable carrier suitable for intravenous injection into an individual. In certain embodiments, the pharmaceutical composition comprises a fusion protein comprising an anti-annexin A2 antibody or antigen-binding fragment thereof fused to a biologically-active fragment of human DAF comprising SCRs 1-4 of human DAF (amino acids 35-285 of SEQ ID NO:17) and a pharmaceutically acceptable carrier suitable for intravenous injection into an individual.

In certain embodiments, the pharmaceutical composition comprises a fusion protein comprising an anti-annexin A2 antibody or antigen-binding fragment thereof fused to full-length factor H and a pharmaceutically acceptable carrier suitable for intravenous injection into an individual. In certain embodiments, the pharmaceutical composition comprises a fusion protein comprising an anti-annexin A2 antibody or antigen-binding fragment thereof fused to a biologically-active fragment of factor H comprising SCRs 1 to 4 and a pharmaceutically acceptable carrier suitable for intravenous injection into an individual. In certain embodiments, the pharmaceutical composition comprises a fusion protein comprising an anti-annexin A2 antibody or antigen-binding fragment thereof fused to a biologically-active fragment of factor H comprising SCRs 1 to 8 and a pharmaceutically acceptable carrier suitable for intravenous injection into an individual. In certain embodiments, the pharmaceutical composition comprises a fusion protein comprising an anti-annexin A2 antibody or antigen-binding fragment thereof fused a biologically-active fragment of factor H comprising SCRs 1 to 18 and a pharmaceutically acceptable carrier suitable for intravenous injection into an individual. In certain embodiments, the pharmaceutical compositions comprise biologically-active fragments of factor H lacking the complement regulatory domain in SCRs 1 to 4 of full-length factor H and a pharmaceutically acceptable carrier suitable for intravenous injection into an individual. In certain embodiments, the biologically-active fragment of factor H comprises SCRs 19 to 20 of factor H and a pharmaceutically acceptable carrier suitable for intravenous injection into an individual.

In certain embodiments, the pharmaceutical composition comprises a fusion protein comprising an anti-annexin A2 antibody or antigen-binding fragment thereof fused to full-length human MCP (SEQ ID NO:19) and a pharmaceutically acceptable carrier suitable for intravenous injection into an individual. In certain embodiments, the pharmaceutical composition comprises a fusion protein comprising an anti-annexin A2 antibody or antigen-binding fragment thereof fused to a biologically-active fragment of human MCP comprising the extracellular domain of human MCP (amino acids 35-343 of SEQ ID NO:19) and a pharmaceutically acceptable carrier suitable for intravenous injection into an individual. In certain embodiments, the pharmaceutical composition comprises a fusion protein comprising an anti-annexin A2 antibody or antigen-binding fragment thereof fused to a biologically-active fragment of human MCP comprising SCRs 1 to 4 of human MCP (amino acids 35-285 of SEQ ID NO:19) and a pharmaceutically acceptable carrier suitable for intravenous injection into an individual.

In certain embodiments, the pharmaceutical composition comprises a fusion protein comprising an anti-annexin A2 antibody or antigen-binding fragment thereof fused to full-length human CD59 (SEQ ID NO:21) and a pharmaceutically acceptable carrier suitable for intravenous injection into an individual. In certain embodiments, the pharmaceutical composition comprises a fusion protein comprising an anti-annexin A2 antibody or antigen-binding fragment thereof fused to a biologically-active fragment of human CD59 comprising the extracellular domain of human CD59 lacking a GPI anchor and/or the amino acid to which it is attached (i.e., Asn-102)(amino acids 26-102 of SEQ ID NO:21) and a pharmaceutically acceptable carrier suitable for intravenous injection into an individual.

In certain embodiments, the pharmaceutical composition comprises a fusion protein comprising an anti-annexin A2 antibody or antigen-binding fragment thereof fused to full-length human CR1 (SEQ ID NO:23) and a pharmaceutically acceptable carrier suitable for intravenous injection into an individual. In certain embodiments, the pharmaceutical composition comprises a fusion protein comprising an anti-annexin A2 antibody or antigen-binding fragment thereof fused to a biologically-active fragment of human CR1 comprising the complete extracellular domain of human CR1 (SCRs 1 to 30)(amino acids 42-1971 of SEQ ID NO:23) and a pharmaceutically acceptable carrier suitable for intravenous injection into an individual. In certain embodiments, the pharmaceutical composition comprises a fusion protein comprising an anti-annexin A2 antibody or antigen-binding fragment thereof fused to a biologically active fragment of full-length human CR1 comprising SCRs 1 to 4 (amino acids 42-295 of SEQ ID NO:23) and a pharmaceutically acceptable carrier suitable for intravenous injection into an individual. In certain embodiments, the pharmaceutical composition comprises a fusion protein comprising an anti-annexin A2 antibody or antigen-binding fragment thereof fused to a biologically active fragment of full-length human CR1 comprising SCRs 1 to 11 (amino acids 42-745 of SEQ ID NO:23) and a pharmaceutically acceptable carrier suitable for intravenous injection into an individual. In certain embodiments, the pharmaceutical composition comprises a fusion protein comprising an anti-annexin A2 antibody or antigen-binding fragment thereof fused to a biologically active fragment of full-length human CR1 comprising SCRs 1 to 18 (amino acids 42-1195 of SEQ ID NO:23) and a pharmaceutically acceptable carrier suitable for intravenous injection into an individual.

In certain embodiments, the pharmaceutical composition comprises a fusion protein comprising an anti-annexin A2 antibody or antigen-binding fragment thereof fused to full-length mouse Crry protein (SEQ ID NO:25) and a pharmaceutically acceptable carrier suitable for intravenous injection into an individual. In certain embodiments, the pharmaceutical composition comprises a fusion protein comprising an anti-annexin A2 antibody or antigen-binding fragment thereof fused to a biologically-active fragment of full-length mouse Crry protein comprising the complete extracellular domain of mouse Crry protein (amino acids 41-405 of SEQ ID NO:25) and a pharmaceutically acceptable carrier suitable for intravenous injection into an individual. In certain embodiments, the pharmaceutical composition comprises a fusion protein comprising an anti-annexin A2 antibody or antigen-binding fragment thereof fused to a biologically-active fragment of full-length mouse Crry protein comprising SCRs 1 to 5 of mouse Crry protein (amino acids 83-400 of SEQ ID NO:25) and a pharmaceutically acceptable carrier suitable for intravenous injection into an individual.

In certain embodiments, the pharmaceutical compositions comprise annexin A2 or biologically-active fragments thereof and a pharmaceutically acceptable carrier suitable for injection into the arteries (such as the renal arteries) of an individual. In certain embodiments, the pharmaceutical compositions comprise fusion proteins comprising an anti-annexin A2 antibody or antigen-binding fragment thereof fused to DAF, factor H, MCP, CD59, CR1, mouse Crry protein or biologically-active fragments thereof and a pharmaceutically acceptable carrier suitable for injection into the arteries (such as the renal arteries) of an individual.

In certain embodiments, the pharmaceutical composition comprises a fusion protein comprising an anti-annexin A2 antibody or antigen-binding fragment thereof fused to full-length human DAF (SEQ ID NO:17) and a pharmaceutically acceptable carrier suitable for injection into the arteries (such as the renal arteries) of an individual. In certain embodiments, the pharmaceutical composition comprises a fusion protein comprising an anti-annexin A2 antibody or antigen-binding fragment thereof fused to a biologically-active fragment of human DAF comprising full-length human DAF lacking its GPI anchor (amino acids 35-353 of SEQ ID NO:17) and a pharmaceutically acceptable carrier suitable for injection into the arteries (such as the renal arteries) of an individual. In certain embodiments, the pharmaceutical composition comprises a fusion protein comprising an anti-annexin A2 antibody or antigen-binding fragment thereof fused to a biologically-active fragment of human DAF comprising SCRs 1-4 of human DAF (amino acids 35-285 of SEQ ID NO:17) and a pharmaceutically acceptable carrier suitable for injection into the arteries (such as the renal arteries) of an individual.

In certain embodiments, the pharmaceutical composition comprises a fusion protein comprising an anti-annexin A2 antibody or antigen-binding fragment thereof fused to full-length factor H and a pharmaceutically acceptable carrier suitable for injection into the arteries (such as the renal arteries) of an individual. In certain embodiments, the pharmaceutical composition comprises a fusion protein comprising an anti-annexin A2 antibody or antigen-binding fragment thereof fused to a biologically-active fragment of factor H comprising SCRs 1 to 4 and a pharmaceutically acceptable carrier suitable for injection into the arteries (such as the renal arteries) of an individual. In certain embodiments, the pharmaceutical composition comprises a fusion protein comprising an anti-annexin A2 antibody or antigen-binding fragment thereof fused to a biologically-active fragment of factor H comprising SCRs 1 to 8 and a pharmaceutically acceptable carrier suitable for injection into the arteries (such as the renal arteries) of an individual. In certain embodiments, the pharmaceutical composition comprises a fusion protein comprising an anti-annexin A2 antibody or antigen-binding fragment thereof fused a biologically-active fragment of factor H comprising SCRs 1 to 18 and a pharmaceutically acceptable carrier suitable for injection into the arteries (such as the renal arteries) of an individual. In certain embodiments, the pharmaceutical compositions comprise biologically-active fragments of factor H lacking the complement regulatory domain in SCRs 1 to 4 of full-length factor H and a pharmaceutically acceptable carrier suitable for injection into the arteries (such as the renal arteries) of an individual. In certain embodiments, the biologically-active fragment of factor H comprises SCRs 19 to 20 of factor H and a pharmaceutically acceptable carrier suitable for injection into the arteries (such as the renal arteries) of an individual.

In certain embodiments, the pharmaceutical composition comprises a fusion protein comprising an anti-annexin A2 antibody or antigen-binding fragment thereof fused to full-length human MCP (SEQ ID NO:19) and a pharmaceutically acceptable carrier suitable for injection into the arteries (such as the renal arteries) of an individual. In certain embodiments, the pharmaceutical composition comprises a fusion protein comprising an anti-annexin A2 antibody or antigen-binding fragment thereof fused to a biologically-active fragment of human MCP comprising the extracellular domain of human MCP (amino acids 35-343 of SEQ ID NO:19) and a pharmaceutically acceptable carrier suitable for injection into the arteries (such as the renal arteries) of an individual. In certain embodiments, the pharmaceutical composition comprises a fusion protein comprising an anti-annexin A2 antibody or antigen-binding fragment thereof fused to a biologically-active fragment of human MCP comprising SCRs 1 to 4 of human MCP (amino acids 35-285 of SEQ ID NO:19) and a pharmaceutically acceptable carrier suitable for injection into the arteries (such as the renal arteries) of an individual.

In certain embodiments, the pharmaceutical composition comprises a fusion protein comprising an anti-annexin A2 antibody or antigen-binding fragment thereof fused to full-length human CD59 (SEQ ID NO:21) and a pharmaceutically acceptable carrier suitable for injection into the arteries (such as the renal arteries) of an individual. In certain embodiments, the pharmaceutical composition comprises a fusion protein comprising an anti-annexin A2 antibody or antigen-binding fragment thereof fused to a biologically-active fragment of human CD59 comprising the extracellular domain of human CD59 lacking a GPI anchor and/or the amino acid to which it is attached (i.e., Asn-102)(amino acids 26-102 of SEQ ID NO:21) and a pharmaceutically acceptable carrier suitable for injection into the arteries (such as the renal arteries) of an individual.

In certain embodiments, the pharmaceutical composition comprises a fusion protein comprising an anti-annexin A2 antibody or antigen-binding fragment thereof fused to full-length human CR1 (SEQ ID NO:23) and a pharmaceutically acceptable carrier suitable for injection into the arteries (such as the renal arteries) of an individual. In certain embodiments, the pharmaceutical composition comprises a fusion protein comprising an anti-annexin A2 antibody or antigen-binding fragment thereof fused to a biologically-active fragment of human CR1 comprising the complete extracellular domain of human CR1 (SCRs 1 to 30)(amino acids 42-1971 of SEQ ID NO:23) and a pharmaceutically acceptable carrier suitable for injection into the arteries (such as the renal arteries) of an individual. In certain embodiments, the pharmaceutical composition comprises a fusion protein comprising an anti-annexin A2 antibody or antigen-binding fragment thereof fused to a biologically active fragment of full-length human CR1 comprising SCRs 1 to 4 (amino acids 42-295 of SEQ ID NO:23) and a pharmaceutically acceptable carrier suitable for injection into the arteries (such as the renal arteries) of an individual. In certain embodiments, the pharmaceutical composition comprises a fusion protein comprising an anti-annexin A2 antibody or antigen-binding fragment thereof fused to a biologically active fragment of full-length human CR1 comprising SCRs 1 to 11 (amino acids 42-745 of SEQ ID NO:23) and a pharmaceutically acceptable carrier suitable for injection into the arteries (such as the renal arteries) of an individual. In certain embodiments, the pharmaceutical composition comprises a fusion protein comprising an anti-annexin A2 antibody or antigen-binding fragment thereof fused to a biologically active fragment of full-length human CR1 comprising SCRs 1 to 18 (amino acids 42-1195 of SEQ ID NO:23) and a pharmaceutically acceptable carrier suitable for injection into the arteries (such as the renal arteries) of an individual.

In certain embodiments, the pharmaceutical composition comprises a fusion protein comprising an anti-annexin A2 antibody or antigen-binding fragment thereof fused to full-length mouse Crry protein (SEQ ID NO:25) and a pharmaceutically acceptable carrier suitable for injection into the arteries (such as the renal arteries) of an individual. In certain embodiments, the pharmaceutical composition comprises a fusion protein comprising an anti-annexin A2 antibody or antigen-binding fragment thereof fused to a biologically-active fragment of full-length mouse Crry protein comprising the complete extracellular domain of mouse Crry protein (amino acids 41-405 of SEQ ID NO:25) and a pharmaceutically acceptable carrier suitable for injection into the arteries (such as the renal arteries) of an individual. In certain embodiments, the pharmaceutical composition comprises a fusion protein comprising an anti-annexin A2 antibody or antigen-binding fragment thereof fused to a biologically-active fragment of full-length mouse Crry protein comprising SCRs 1 to 5 of mouse Crry protein (amino acids 83-400 of SEQ ID NO:25) and a pharmaceutically acceptable carrier suitable for injection into the arteries (such as the renal arteries) of an individual. In certain embodiments, the pharmaceutically acceptable carrier is suitable for oral administration to an individual.

For oral administration, the pharmaceutical compositions can take the form of, for example, tablets or capsules prepared by conventional means with pharmaceutically acceptable excipients such as binding agents (e.g., pregelatinized maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulfate). Liquid preparations for oral administration can take the form of, for example, solutions, syrups or suspensions, or they can be presented as a dry product for constitution with water or other suitable vehicle before use. Such liquid preparations can be prepared by conventional means with pharmaceutically acceptable additives such as suspending agents (e.g., sorbitol syrup, cellulose derivatives or hydrogenated edible fats); emulsifying agents (e.g., lecithin or *acacia*); non-aqueous vehicles (e.g., ationd oil, oily esters, ethyl alcohol or fractionated vegetable oils); and preservatives (e.g., methyl or propyl-p-hydroxybenzoates or sorbic acid). The preparations can also contain buffer salts, flavoring, coloring and sweetening agents as appropriate.

The liquid compositions are generally formulated as sterile, substantially isotonic solutions in full compliance with all Good Manufacturing Practice (GMP) regulations of the U.S. Food and Drug Administration. In certain embodiments, the composition is free of pathogen. For injection, the pharmaceutical composition can be in the form of liquid solutions, for example in physiologically compatible buffers such as Hank's Balanced Salt Solution, Phosphate-Buffered Saline or Ringer's solution. In addition, the pharmaceutical compositions provided herein can be in solid form and redissolved or resuspended immediately prior to use. Lyophilized compositions are also contemplated.

In certain embodiments, the composition is formulated in accordance with routine procedures as a pharmaceutical composition adapted for injection. In certain embodiments, the pharmaceutical compositions provided herein are formulated for intravenous, intraperitoneal, or intraocular injection. Typically, compositions for injection are solutions in sterile isotonic aqueous buffer. Where necessary, the composition may also include a solubilizing agent and a local anesthetic such as lignocaine to ease pain at the site of the injection. Generally, the ingredients are supplied either separately or mixed together in unit dosage form, for example, as a dry lyophilized powder or water-free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The pharmaceutical compositions may further comprise additional ingredients, for example preservatives, buffers, tonicity agents, antioxidants and stabilizers, nonionic wetting or clarifying agents, viscosity-increasing agents, and the like.

Suitable preservatives for use in a solution include polyquaternium-1, benzalkonium chloride, thimerosal, chlorobutanol, methyl paraben, propyl paraben, phenylethyl alcohol, disodium-EDTA, sorbic acid, benzethonium chloride, and the like. Typically (but not necessarily) such preservatives are employed at a level of from 0.001% to 1.0% by weight.

Suitable buffers include boric acid, sodium and potassium bicarbonate, sodium and potassium borates, sodium and potassium carbonate, sodium acetate, sodium biphosphate and the like, in amounts sufficient to maintain the pH at between about pH 6 and pH 8, and preferably, between about pH 7 and pH 7.5.

Suitable tonicity agents include dextran 40, dextran 70, dextrose, glycerin, potassium chloride, propylene glycol, sodium chloride, and the like, such that the sodium chloride equivalent of the injectable solution is in the range 0.9 plus or minus 0.2%.

Suitable antioxidants and stabilizers include sodium bisulfite, sodium metabisulfite, sodium thiosulfite, thiourea and the like. Suitable wetting and clarifying agents include polysorbate 80, polysorbate 20, poloxamer 282 and tyloxapol. Suitable viscosity-increasing agents include dextran 40, dextran 70, gelatin, glycerin, hydroxyethylcellulose, hydroxmethylpropylcellulose, lanolin, methylcellulose, petrolatum, polyethylene glycol, polyvinyl alcohol, polyvinylpyrrolidone, carboxymethylcellulose and the like.

The pharmaceutical compositions may be suitable for a variety of modes of administration described herein, including for example systemic or localized administration. The pharmaceutical compositions can be in the form of eye drops, injectable solutions, or in a form suitable for inhalation (either through the mouth or the nose) or oral administration. The pharmaceutical compositions described herein can be packaged in single unit dosages or in multidosage forms.

In certain embodiments, the pharmaceutical compositions comprise annexin A2 or biologically-active fragments thereof and a pharmaceutically acceptable carrier suitable for administration to a human. In certain embodiments, the pharmaceutical compositions comprise fusion proteins comprising an anti-annexin A2 antibody or antigen-binding fragment thereof fused to factor H or a biologically-active fragment thereof and a pharmaceutically acceptable carrier suitable for administration to a human. In certain embodiments, the pharmaceutical composition comprises a fusion protein comprising an anti-annexin A2 antibody or antigen-binding fragment thereof fused to full-length factor H and a pharmaceutically acceptable carrier suitable for administration to a human. In certain embodiments, the pharmaceutical composition comprises a fusion protein comprising an anti-annexin A2 antibody or antigen-binding fragment thereof fused to a biologically-active fragment of factor H comprising SCRs 1 to 4 and a pharmaceutically acceptable carrier suitable for administration to a human. In certain embodiments, the pharmaceutical composition comprises a fusion protein comprising an anti-annexin A2 antibody or antigen-binding fragment thereof fused to a biologically-active fragment of factor H comprising SCRs 1 to 8 and a pharmaceutically acceptable carrier suitable for administration to a human. In certain embodiments, the pharmaceutical composition comprises a fusion protein comprising an anti-annexin A2 antibody or antigen-binding fragment thereof fused to a biologically-active fragment of factor H comprising SCRs 1 to 18 and a pharmaceutically acceptable carrier suitable for administration to a human.

In certain embodiments, the pharmaceutical compositions comprise biologically-active fragments of factor H lacking the complement regulatory domain in SCRs 1 to 4 of full-length factor H and a pharmaceutically acceptable carrier suitable for administration to a human. In certain embodiments, the biologically-active fragment of factor H comprises SCRs 19 to 20 of factor H and a pharmaceutically acceptable carrier suitable for administration to a human. In certain embodiments, the pharmaceutical compositions comprising biologically-active fragments of factor H lacking the complement regulatory domain in SCRs 1 to 4 of full-length factor H and a pharmaceutically acceptable carrier are suitable for administration to an individual or a human by any route of administration described herein, including oral administration, intravenous injection, or injection into the arteries, such as the renal arteries. In certain embodiments, the pharmaceutical compositions comprising a biologically-active fragment of factor H comprising SCRs 19 to 20 of factor H and a pharmaceutically acceptable carrier are suitable for administration to an individual or a human by any route of administration described herein, including oral administration, intravenous injection, or injection into the arteries, such as the renal arteries.

In certain embodiments, the pharmaceutical compositions comprise annexin A2 or biologically-active fragments thereof and a pharmaceutically acceptable carrier suitable for intraocular injection in an individual. In certain embodiments, the pharmaceutical compositions comprise fusion proteins comprising an anti-annexin A2 antibody or antigen-binding fragment thereof fused to factor H or a biologically-active fragment thereof and a pharmaceutically acceptable carrier suitable for intraocular injection in an individual. In certain embodiments, the pharmaceutical composition comprises a fusion protein comprising an anti-annexin A2 antibody or antigen-binding fragment thereof fused to full-length factor H and a pharmaceutically acceptable carrier suitable for intraocular injection in an individual. In certain embodiments, the pharmaceutical composition comprises a fusion protein comprising an anti-annexin A2 antibody or antigen-binding fragment thereof fused to a biologically-active fragment of factor H comprising SCRs 1 to 4 and a pharmaceutically acceptable carrier suitable for intraocular injection in an individual. In certain embodiments, the pharmaceutical composition comprises a fusion protein comprising an anti-annexin A2 antibody or antigen-binding fragment thereof fused to a biologically-active fragment of factor H comprising SCRs 1 to 8 and a pharmaceutically acceptable carrier suitable for intraocular injection in an individual. In certain embodiments, the pharmaceutical composition comprises a fusion protein comprising an anti-annexin A2 antibody or antigen-binding fragment thereof fused a biologically-active fragment of factor H comprising SCRs 1 to 18 and a pharmaceutically acceptable carrier suitable for intraocular injection in an individual. In certain embodiments, the pharmaceutical compositions comprise biologically-active fragments of factor H lacking the complement regulatory domain in SCRs 1 to 4 of full-length factor H and a pharmaceutically acceptable carrier suitable for intraocular injection in an individual. In certain embodiments, the biologically-active fragment of factor H comprises SCRs 19 to 20 of factor H and a pharmaceutically acceptable carrier suitable for intraocular injection in an individual.

In certain embodiments, the pharmaceutical compositions comprise annexin A2 or biologically-active fragments thereof and a pharmaceutically acceptable carrier suitable for topical administration to the eye of an individual. In certain embodiments, the pharmaceutical compositions comprise fusion proteins comprising an anti-annexin A2 antibody or antigen-binding fragment thereof fused to factor H or a biologically-active fragment thereof and a pharmaceutically acceptable carrier suitable for topical administration to the eye of an individual. In certain embodiments, the pharmaceutical composition comprises a fusion protein comprising an anti-annexin A2 antibody or antigen-binding fragment thereof fused to full-length factor H and a pharmaceutically acceptable carrier suitable for topical administration to the eye of an individual. In certain embodiments, the pharmaceutical composition comprises a fusion protein comprising an anti-annexin A2 antibody or antigen-binding fragment thereof fused to a biologically-active fragment of factor H comprising SCRs 1 to 4 and a pharmaceutically acceptable carrier suitable for topical administration to the eye of an individual. In certain embodiments, the pharmaceutical composition comprises a fusion protein comprising an anti-annexin A2 antibody or antigen-binding fragment thereof fused to a biologically-active fragment of factor H comprising SCRs 1 to 8 and a pharmaceutically acceptable carrier suitable for topical administration to the eye of an individual. In certain embodiments, the pharmaceutical composition comprises a fusion protein comprising an anti-annexin A2 antibody or antigen-binding fragment thereof fused a biologically-active fragment of factor H comprising SCRs 1 to 18 and a pharmaceutically acceptable carrier suitable for topical administration to the eye of an individual. In certain embodiments, the pharmaceutical compositions comprise biologically-active fragments of factor H lacking the complement regulatory domain in SCRs 1 to 4 of full-length factor H and a pharmaceutically acceptable carrier suitable for topical administration to the eye of an individual. In certain embodiments, the biologically-active fragment of factor H comprises SCRs 19 to 20 of factor H and a pharmaceutically acceptable carrier suitable for topical administration to the eye of an individual.

There are provided herein in certain embodiments compositions comprising annexin A2 or biologically-active fragments thereof, fusion proteins comprising an anti-annexin A2 antibody or antigen-binding fragment thereof fused to factor H or a biologically-active fragment thereof, or biologically-active fragments of factor H and a pharmaceutically acceptable carrier suitable for administration to the eye. Such pharmaceutical carriers can be sterile liquids, such as water and oil, including those of petroleum, animal, vegetable or synthetic origin, such as peanut oil, soybean oil, mineral oil, and the like. Saline solutions and aqueous dextrose, polyethylene glycol (PEG) and glycerol solutions can also be employed as liquid carriers, particularly for injectable solutions. Suitable pharmaceutical excipients include starch, glucose, lactose, sucrose, gelatin, malt, rice, sodium state, glycerol monostearate, glycerol, propylene, water, and the like. The pharmaceutical composition, if desired, can also contain minor amounts of wetting or emulsifying agents, or pH buffering agents. The annexin A2 or biologically-active fragments thereof, fusion proteins comprising an anti-annexin A2 antibody or antigen-binding fragment thereof fused to factor H or a biologically-active fragment thereof, or biologically-active fragments of factor H and other components of the composition may be encased in polymers or fibrin glues to provide controlled release of the molecule. These compositions can take the form of solutions, suspensions, emulsions, ointment, gel, or other solid or semisolid compositions, and the like. The compositions typically have a pH in the range of 4.5 to 8.0. The compositions must also be formulated to have osmotic values that are compatible with the aqueous humor of the eye and ophthalmic tissues. Such osmotic values will generally be in the range of from about 200 to about 400 milliosmoles per kilogram of water (mOsm/kg), but will preferably be about 300 mOsm/kg.

The use of viscosity enhancing agents to provide topical compositions with viscosities greater than the viscosity of simple aqueous solutions may be desirable to increase ocular absorption of the active compounds by the target tissues or increase the retention time in the eye. Thus, in certain embodiments, the compositions further comprise viscosity enhancing agents. Such viscosity enhancing agents include, for example, polyvinyl alcohol, polyvinyl pyrrolidone, methyl cellulose, hydroxy propyl methylcellulose, hydroxyethyl cellulose, carboxymethyl cellulose, hydroxy propyl cellulose or other agents know to those skilled in the art. Such agents are typically employed at a level of from 0.01% to 2% by weight.

Methods of Modulating Activity of the Alternative Complement Pathway

In another aspect, there are provided methods of modulating, i.e., stimulating or inhibiting, alternative complement activity in an individual. In certain embodiments, the methods comprise methods of inhibiting alternative complement activity. In certain embodiments, the alternative complement activity is associated with inflammation. In certain embodiments, the inflammation is renal inflammation. In certain embodiments, the renal inflammation is associated with membranoproliferative glomerulonephritis type II (MPGN II), hemolytic uremic syndrome, atypical hemolytic uremic syndrome, thrombotic thrombocytopenic purpura, ischemia reperfusion (I/R) injury, and ischemic acute kidney injury. In certain embodiments, the methods comprise methods of inhibiting alternative complement activity associated with drusen-related disease. In certain embodiments, the drusen-related diseases are selected from the group consisting of membranoproliferative glomerulonephritis type II (MPGN II), age-related macular degeneration, and amyloidosis.

In certain embodiments, the methods comprise methods of stimulating alternative complement activity. In certain embodiments, the methods stimulate alternative complement by administering a composition comprising a biologically-active fragment of factor H comprising SCRs 19 and 20 in conjunction with a monoclonal antibody-based therapeutic. In certain embodiments, the monoclonal antibody-based therapeutic is an anti-cancer agent. In other embodiments, the methods stimulate alternative complement by administering a composition comprising an annexin A2 or a biologically-active fragment thereof As used herein, the term "ischemia reperfusion (I/R) injury" refers to inflammatory injury to the endothelium and underlying parenchymal tissues following reperfusion of hypoxic tissues. It is a general syndrome that is responsible for both acute and chronic injury to various tissues including, for example, myocardium, central nervous system, hind limb and intestine. Ischemia reperfusion injury can result in necrosis and irreversible cell injury. The complement pathway (including the alternative complement pathway) is a major mediator of I/R injury. The methods provided herein are thus useful for inhibiting alternative complement-mediated inflammation associated with ischemia reperfusion, particularly that occurring in renal ischemia-reperfusion injury. Ischemia-reperfusion injury can also occur in conjunction with a variety of other conditions including, but not limited to, stroke, spinal cord injury, trauma-induced hypovolemic shock, and autoimmune diseases such as rheumatoid arthritis (e.g., which can be greatly worsened by ischemic injury of the synovium) or a variety of other inflammatory diseases (diseases mediated by inflammation or wherein inflammation is a symptom that may result in or be associated with ischemic events and reperfusion). Other conditions and diseases in which ischemia-reperfusion injury occurs will be known to those of skill in the art.

As used herein, the term "ischemic acute kidney injury" or "AKI" refers to an I/R-associated injury in rodents (J. M. Thurman et al., *J. Immunol.* (2003) 170:1517-1523; J. M. Thurman et al., *J. Am. Soc. Nephrol.* (2006) 17:707-715) and in humans (J. M. Thurman et al., *Kidney Int.* (2005) 67:524-530) that is associated with activation of the alternative pathway on the basolateral surface of injured tubular cells. Complement receptor 1-related gene/protein y (Crry, a rodent analog of human MCP and CR1) is the only CRP expressed by proximal tubular epithelial cells in mice. I/R causes reduced surface expression of this protein. See J. M. Thurman et al., *J. Clin. Invest.* (2006) 116:357-368. Mice with congenital deficiency of Crry (Crry+/−) are more sensitive than wild-type controls to ischemic acute renal failure (Id.), highlighting the importance of basolateral Crry for controlling the alternative pathway on this surface. Uncontrolled activation of the alternative pathway in the setting of reduced surface Crry indicates that circulating factor H has a limited ability to protect the surface of hypoxic tubular epithelial cells in rodents and humans.

As used herein, the term "hemolytic uremic syndrome" or "HUS" refers to a disease characterized by microangiopathic hemolytic anemia and thrombocytopenia, ultimately resulting in acute renal failure, caused by continuous platelet degradation in the periphery and platelet thrombin in the microcirculation of the kidney. See Zipfel, *Seminars in Thrombosis Hemostasis* (2001) 27(3):191-199. There is now considerable evidence that the nondiarrheal form of HUS (also known as atypical HUS, or aHUS) is associated with alternations and mutations of FH. In addition, autoantibodies to FH have been reported in aHUS patients. Thus, evidence suggests that the alternative complement pathway is involved in the development and progression of HUS and aHUS.

As used herein, the term "thrombotic thrombocytopenic purpura" or "TTP" refers to a rare disease characterized by microangiopathic hemolytic anemia, causing blood clots to form in small blood vessels throughout the body. These blood clots can cause serious problems if they block blood vessels and limit blood flow to the brain, kidneys, or heart. Blood clots form when blood cells called platelets clump together. Formation of the blood clots characteristic of TTP depletes circulating platelet levels, sometimes resulting in bleeding into the skin (purpura), prolonged bleeding from cuts, and internal bleeding. It also causes small blood clots to form suddenly throughout the body, including in the brain and kidneys.

Annexin A2 has also been identified as a component of drusen in monkeys affected with both early- and late-onset macular degeneration, suggesting that the methods provided herein may also be used to inhibit alternative complement activity in drusen-associated diseases. See S. Umeda et al., *FASEB J.* (2005) 19(12):1683-1685. As used herein, the term "drusen-associated disease" refers to any disease in which formation of drusen or drusen-like extracellular disease plaque takes place, and for which drusen or drusen-like extracellular disease plaque causes or contributes to thereto or represents a sign thereof. For example, age-related macular degeneration (AMD), characterized by the formation of macular drusen, is considered a drusen-associated disease. Non-ocular drusen-related disease include, but are not limited to, amyloidosis and dense deposit disease (i.e., type II membranoproliferative glomerulonephritis).

The methods provided herein may also be used to treat alternative complement-mediated inflammation in drusen-associated diseases. As used herein, the term "drusen-associated disease" refers to any disease in which formation of drusen or drusen-like extracellular disease plaque takes place, and for which drusen or drusen-like extracellular disease plaque causes or contributes to thereto or represents a sign thereof. For example, age-related macular degeneration (AMD), characterized by the formation of macular drusen, is considered a drusen-associated disease. Non-ocular drusen-related disease include, but are not limited to, amyloidosis, elastosis, dense deposit disease, and/or atherosclerosis. The term "drusen-related disease" also includes glomerulonephritis, such as MPGN II.

As used herein, the term "membranoproliferative glomerulonephritis type II" or "MPGN II", or "dense deposit disease" refers to a rare kidney disease leading to persistent proteinuria, hematuria, and nephritic syndrome. Factor H deficiency and dysfunction in MPGN II have been reported in several cases. For example, mutations in factor H have been found in human patients with MPGN II. Pigs of the Norwegian Yorkshire breed have factor H defects that are inherited in a recessive pattern. These animals develop MPGN II, show massive complement deposits in the renal glomeruli and die at an early age because of the renal failure. In some cases, those complement deposits resemble the drusen characteristic of age-related macular degeneration. As discussed above, annexin A2 has been shown to be a component of drusen. Furthermore, an autoantibody that recognizes factor H has been described in a patient with hypocomplementemic MPGN II. Thus, evidence suggests that the alternative complement pathway is involved in the development and progression of MPGN II.

As used herein, the term "age-related macular degeneration" or "AMD" refers to a disorder clinically characterized by progressive loss of central vision which occurs as a result of damage to the photoreceptor cells in an area of the retina called the macula. AMD has been broadly classified into two clinical states: a wet form and a dry form, with the dry form making up to 80-90% of total cases. The dry form is characterized clinically by the presence of macular drusen, which are localized deposits between the retinal pigment epithelium (RPE) and the Bruch's membrane, and by geographic atrophy characterized by RPE cell death with overlying photoreceptor atrophy. Wet AMD, which accounts for approximately 90% of serious vision loss, is associated with neovascularization in the area of the macular and leakage of these new vessels. The accumulation of blood and fluid can cause retina detachment followed by rapid photoreceptor degeneration and loss of vision. It is generally accepted that the wet form of AMD is preceded by and arises from the dry form. Analysis of the contents of drusen in AMD patients has identified a large number of inflammatory proteins including amyloid proteins, annexin A2, coagulation factors, and a large number of proteins of the complement pathway. A genetic variation in the complement factor H substantially raises the risk of age-related macular degeneration (AMD), suggesting that uncontrolled complement activation underlies the pathogenesis of AMD. See Edward et al., *Science* (2005) 308:421; Haines et al., *Science* (2005) 308:419; Klein et al., *Science* 308:385-389; Hageman et al., *Proc. Natl. Acad. Sci. USA* (2005), 102:7227.

As used herein, the term "amyloidosis" refers to a group of conditions in which abnormal organ or tissue deposits of amyloid proteins cause disease. Various proteins take on "amyloid form" due to characteristic alterations in their secondary structure. The term "amyloidosis" refers to a histological finding of amyloid deposits occurring in a number of different disease processes. Amyloidoses can be systemic (affecting many different organ systems) or organ-specific. Some are inherited as a result of mutations in the amyloid precursor protein, while others result from different diseases causing overabundant or abnormal protein production-such as with over production of immunoglobulin light chains in multiple myeloma (referred to as "AL amyloid").

In certain embodiments, the methods comprise methods of inhibiting alternative complement activity. In certain embodiments, the alternative complement activity is associated with inflammation. Complement-mediated inflammation associated with many diseases in which any of the three complement pathways is implicated can be treated by the methods as described herein. Such diseases include, for example: (1) tissue damage due to ischemia-reperfusion following acute myocardial infarction, aneurysm, stroke, hemorrhagic shock, crush injury, multiple organ failure, hypovolemic shock intestinal ischemia, spinal cord injury, and traumatic brain injury; (2) inflammatory disorders, e.g., burns, endotoxemia and septic shock, adult respiratory distress syndrome, cardiopulmonary bypass, hemodialysis; anaphylactic shock, severe asthma, angioedema, Crohn's disease, sickle cell anemia, poststreptococcal glomerulonephritis, membraneous nephritis, and pancreatitis; (3) transplant rejection, e.g., hyperacute xenograft rejection; (4) pregnancy related diseases such as recurrent fetal loss and pre-eclampsia, and (5) adverse drug reactions, e.g., drug allergy, IL-2 induced vascular leakage syndrome and radiographic contrast media allergy. Alternative complement-mediated inflammation associated with autoimmune disorders including, but not limited to, myasthenia gravis, Alzheimer's disease, multiple sclerosis, rheumatoid arthritis, systemic lupus erythematosus, insulin-dependent diabetes mellitus, acute disseminated encephalomyelitis, Addison's disease, antiphospholipid antibody syndrome, autoimmune hepatitis, Crohn's disease, Goodpasture's syndrome, Graves' disease, Guillain-Barré syndrome, Hashimoto's disease, idiopathic thrombocytopenic purpura, pemphigus, Sjögren's syndrome, and Takayasu's arteritis, may also be treated with the compositions described herein.

In certain embodiments, the alternative complement-mediated inflammation to be treated by the methods provided herein is associated with any of the following disorders: post cardiopulmonary bypass complications; myocardial infarction; ischemia/reperfusion injury; stroke; acute respiratory distress syndrome (ARDS); sepsis; burn injury; inflammation associated with cardiopulmonary bypass and hemodialysis; plasmapheresis; plateletpheresis; leukopheresis; extracorporeal membrane oxygenation (ECMO); heparin-induced extracorporeal LDL precipitation (HELP); radiographic contrast media-induced allergic response; transplant rejection; and other inflammatory conditions and autoimmune/immune complex diseases such as multiple sclerosis, myasthemia gravis, pancreatitis, rheumatoid arthritis, Alzheimer's disease, asthma, thermal injury, anaphylactic shock, bowel inflammation, urticaria, angioedema, vasculitis, glomerulonephritis, and Sjögren's syndrome, systemic lupus erythromatosus and lupus nephritis.

Rheumatoid arthritis is a chronic disease which can exhibit a variety of systemic manifestations. This disease has an unknown etiology and characteristically exhibits a persistent inflammatory synovitis which usually involves peripheral joints in a symmetric distribution. The most important feature of this incurable condition is complement-mediated inflammation which causes cartilage destruction, bone erosions and, ultimately, joint deformities that are the hallmark of the disease.

In certain embodiments, there is provided a method of modulating alternative complement activity in an individual, comprising administering to the individual a composition selected from the group consisting of (a) annexin A2 or a biologically-active fragment thereof; (b) a fusion protein comprising an anti-annexin A2 antibody or an antigen-binding fragment thereof fused to DAF, factor H, MCP, CD59, CR1, or mouse Crry protein or a biologically-active fragment thereof; and (c) a biologically-active fragment of factor H lacking the complement regulatory domain in SCRs 1 to 4 of full-length factor H. In certain embodiments, the individual is a mammal. In certain embodiments, the mammal is a human, a mouse, or a rat. In certain embodiments, alternative complement activity is inhibited in an individual. In certain embodiments, the individual is administered a composition selected from the group consisting of (a) annexin A2 or a biologically-active fragment thereof; and (b) a fusion protein comprising an anti-annexin A2 antibody or antigen-binding fragment thereof fused to DAF, factor H, MCP, CD59, CR1, mouse Crry protein or a biologically-active fragment thereof. In certain embodiments, the individual is administered a composition comprising annexin A2 or a biologically-active fragment thereof. In certain embodiments, the individual is administered a composition comprising annexin A2. In certain embodiments, the composition is administered orally or by injection. In certain embodiments, the composition is injected intravenously.

In certain embodiments, alternative complement activity is inhibited in an individual, and the individual is administered a composition comprising a fusion protein comprising an anti-annexin A2 antibody or antigen-binding fragment thereof fused to DAF, factor H, MCP, CD59, CR1, mouse Crry protein or a biologically-active fragment thereof. In certain embodiments, the antigen-binding fragment thereof comprises an Fab, Fab', or $F(ab')_2$ fragment. In certain embodiments, the biologically active fragment of DAF fused to an anti-annexin A2 antibody or antigen-binding fragment thereof comprises the mature human DAF protein (amino acids 35-353 of SEQ ID NO:17) without its GPI anchor. In certain embodiments, the biologically active fragment of human DAF fused to an anti-annexin A2 antibody or antigen-binding fragment thereof comprises short consensus repeat sequences 1 to 4 (SCRs 1 to 4) of full-length human DAF (amino acids 35 to 285 of SEQ ID NO:17). In certain embodiments, the biologically-active fragment of factor H fused to an anti-annexin A2 antibody or antigen-binding fragment thereof comprises SCRs 1 to 4, SCRs 1 to 8, or SCRs 1 to 18 of full-length factor H. In certain embodiments, the biologically active fragment of MCP fused to an anti-annexin A2 antibody or antigen-binding fragment thereof comprises the extracellular domain of full-length human MCP (amino acids 35-343 of SEQ ID NO:19). In certain embodiments, the biologically active fragment of MCP fused to an anti-annexin A2 antibody or antigen-binding fragment thereof comprises SCRs 1 to 4 of full-length human MCP (amino acids 35-285 of SEQ ID NO:19). In certain embodiments, the biologically active fragment of CD59 fused to an anti-annexin A2 antibody or antigen-binding fragment thereof comprises the extracellular domain of full-length human CD59 (amino acids 26-102 of SEQ ID NO:21) lacking its GPI anchor and/or the amino acid to which it is attached (i.e., Asn-102).

In certain embodiments, the biologically active fragment of CR1 fused to an anti-annexin A2 antibody or antigen-binding fragment thereof comprises the complete extracellular domain of full-length human CR1 (SCRs 1 to 30) (amino acids 42-1971 of SEQ ID NO:23). In certain embodiments, the biologically active fragment of CR1 fused to an anti-annexin A2 antibody or antigen-binding fragment thereof comprises SCRs 1 to 4 of full-length human CR1 (amino acids 42-295 of SEQ ID NO:23). In certain embodiments, the biologically active fragment of CR1 fused to an anti-annexin A2 antibody or antigen-binding fragment thereof comprises SCRs 1 to 11 of full-length human CR1 (amino acids 42-745 of SEQ ID NO:23). In certain embodiments, the biologically active fragment of CR1 fused to an anti-annexin A2 antibody or antigen-binding fragment thereof comprises SCRs 1 to 18 of full-length human CR1 (amino acids 42-1195 of SEQ ID NO:23). In certain embodiments, the biologically active fragment of mouse Crry protein fused to an anti-annexin A2 antibody or antigen-binding fragment thereof comprises the complete extracellular domain of full-length mouse Crry protein (amino acids 41-405 of SEQ ID NO:25). In certain embodiments, the biologically active fragment of mouse Crry protein fused to an anti-annexin A2 antibody or antigen-binding fragment thereof comprises short consensus repeat sequences 1 to 5 (SCRs 1 to 5) of full-length mouse Crry protein (amino acids 83-400 of SEQ ID NO:25). In any of the embodiments disclosed herein, the composition is administered to an individual orally or by injection. In certain embodiments, the composition is administered to an individual by intravenous injection. In certain embodiments, the composition is administered to an individual by injection into the arteries (such as the renal arteries).

In certain embodiments, alternative complement activity is inhibited in an individual. In certain embodiments, the alternative complement activity that is inhibited is associated with renal inflammation or a drusen-related disease. In certain embodiments, the renal inflammation is associated with membranoproliferative glomerulonephritis type II ("MPGN II"), hemolytic uremic syndrome ("HUS"), atypical hemolytic uremic syndrome ("aHUS"), thrombotic thrombocytopenic purpura ("TTP"), ischemia/reperfusion injury, or ischemic acute kidney injury. In certain embodiments, the drusen-related disease is selected from the group consisting of MPGN II, age-related macular degeneration, and amyloidosis.

In certain embodiments, alternative complement activity is inhibited in an individual. In certain embodiments, the alternative complement activity that is inhibited is associated with (1) tissue damage due to ischemia-reperfusion following acute myocardial infarction, aneurysm, stroke, hemorrhagic shock, crush injury, multiple organ failure, hypovolemic shock intestinal ischemia, spinal cord injury, and traumatic brain injury; (2) inflammatory disorders, e.g., burns, endotoxemia and septic shock, adult respiratory distress syndrome, cardiopulmonary bypass, hemodialysis; anaphylactic shock, severe asthma, angioedema, Crohn's disease, sickle cell anemia, poststreptococcal glomerulonephritis, membraneous nephritis, and pancreatitis; (3) transplant rejection, e.g., hyperacute xenograft rejection; (4) pregnancy related diseases such as recurrent fetal loss and pre-eclampsia, and (5) adverse drug reactions, e.g., drug allergy, IL-2 induced vascular leakage syndrome and radiographic contrast media allergy. In certain embodiments, the alternative complement activity that is inhibited is associated with autoimmune disorders including, but not limited to, myasthenia gravis, Alzheimer's disease, multiple sclerosis, rheumatoid arthritis, systemic lupus erythematosus, insulin-dependent diabetes mellitus, acute disseminated encephalomyelitis, Addison's disease, antiphospholipid antibody syndrome, autoimmune hepatitis, Crohn's disease, Goodpasture's syndrome, Graves' disease, Guillain-Barré syndrome, Hashimoto's disease, idiopathic thrombocytopenic purpura, pemphigus, Sjögren's syndrome, and Takayasu's arteritis.

In certain embodiments, the alternative complement activity that is inhibited is associated with any of the following disorders: post cardiopulmonary bypass complications; myocardial infarction; ischemia/reperfusion injury; stroke; acute respiratory distress syndrome (ARDS); sepsis; burn injury; inflammation associated with cardiopulmonary bypass and hemodialysis; plasmapheresis; plateletpheresis; leukopheresis; extracorporeal membrane oxygenation (ECMO); heparin-induced extracorporeal LDL precipitation (HELP); radiographic contrast media-induced allergic response; transplant rejection; and other inflammatory conditions and autoimmune/immune complex diseases such as multiple sclerosis, myasthemia gravis, pancreatitis, rheumatoid arthritis, Alzheimer's disease, asthma, thermal injury, anaphylactic shock, bowel inflammation, urticaria, angioedema, vasculitis, glomerulonephritis, and Sjögren's syndrome, systemic lupus erythromatosus and lupus nephritis.

In certain embodiments, alternative complement activity is stimulated in an individual. In certain embodiments, the individual is administered a composition selected from the group consisting of a biologically-active fragment of factor H lacking the complement regulatory domain in SCRs 1 to 4 of full-length factor H. In certain embodiments, the biologically active fragment of factor H comprises SCRs 19 and 20. In certain embodiments, the methods comprise stimulating alternative complement by administering a composition comprising a biologically-active fragment of factor H comprising SCRs 19 and 20 in conjunction with a monoclonal antibody-based therapeutic. In certain embodiments, the monoclonal antibody-based therapeutic is an anti-cancer agent. In certain embodiments, the alternative complement activity is stimulated in an individual by administering an effective amount of a composition comprising an annexin A2 or a biologically-active fragment thereof. In certain embodiments, the composition is administered orally or by injection. In certain embodiments, the composition is injected intravenously.

The pharmaceutical compositions described herein can be administered to an individual via any route, including, but not limited to, intravenous (e.g., by infusion pumps), intraperitoneal, intraocular, intraarterial, intravesicular, intramuscular, subcutaneous, intrathecal, transpleural, intraarterial, oral, subcutaneous, intraarticular, intracisternal, intraventricular, intracranial, intraurethral, intrahepatic, and intratumoral. In certain embodiments, the pharmaceutical compositions provided herein are administered systemically (for example, by intravenous injection). In certain embodiments, the pharmaceutical compositions provided herein are administered locally (for example, by intraarterial or intraocular injection).

In certain embodiments, the pharmaceutical compositions provided herein are administered directly to the eye or the eye tissue. In certain embodiments, the pharmaceutical compositions are administered by injection to the eye (intraocular injection) or to the tissues associated with the eye. The pharmaceutical compositions provided herein can be administered, for example, by intraocular injection, periocular injection, subretinal injection, intravitreal injection, transseptal injection, subscleral injection, intrachoroidal injection, intracameral injection, subconjunctival injection, subtenon injection, retrobulbar injection, or peribulbar injection. These methods are known in the art. For example, exemplary periocular routes for retinal drug delivery are disclosed in "Periocular routes for retinal drug delivery," Raghava et al., *Exp. Opin. Drug Deliv.* (2004) 1(1):99-114. The compositions described herein may be administered, for example, to the vitreous humor, aqueous humor, sclera, conjunctiva, the area between the sclera and conjunctiva, the retina, the choroid, the macula, to any other area in or proximate to the eye of an individual.

In certain embodiments, the compositions are administered intravascularly, such as intravenously (IV) or intraarterially. In certain embodiments (for example for the treatment of renal diseases), the compositions are administered directly into arteries (such as the renal arteries).

EXAMPLES

Example 1

Factor H Purification, Analysis and Activities

Materials and Methods

Purification of mouse factor H. An affinity column for factor H was made by ligating polyclonal goat antibody for human factor H (Quidel Corp., San Diego, Calif.) to Sepharose® derivatized with cyanogen bromide (CNBr) (Amersham Biosciences/GE Healthcare, Piscataway, N.J.) according to the manufacturer's instructions. Plasma was collected from C57BL/6 mice and passed over the column. After washing the column with phosphate buffered saline (PBS), pH 7.4, the factor H was eluted with 5 M $LiCl_2$. The salt solution was exchanged with PBS and the factor H was then passed through a Sephadex™ 26/60 Superdex™ 200 column (Amersham Biosciences/GE Healthcare, Piscataway, N.J.). The purity and identity of the isolated protein was verified by Coomassie staining and Western blot analysis by standard methods.

Western blot and Far Western blot analysis. Renal tissue was homogenized in radioimmunoprecipitation assay (RIPA) lysis buffer containing 1% Triton® X-100, 0.5% deoxycholic acid, 150 mM NaCl, 20 mM β-glycerophosphate, 20 mM Tris.HCl (pH 8.0), 5 mM EGTA, 3 mM $MgCl_2$, 0.1% SDS, 1 mM DTT, 50 μM $Na_3VO_4$, and one tablet of EDTA-free Complete™ Protease Inhibitor Cocktail (Roche Applied Science, Indianapolis, Ind.). Homogenates were centrifuged at 14,000 rpm for 15 minutes at 4° C. and the supernatant collected. Protein concentrations for kidney samples were determined using the BioRad protein assay (BioRad Laboratories, Hercules, Calif.). One hundred micrograms of protein from each kidney was resolved by electrophoresis on a 10% Bis-Tris polyacrylamide gel (Invitrogen, Carlsbad, Calif.) and transferred to a nitrocellulose membrane.

Monolayers of proximal tubule epithelial cells (PTECs) were washed with phosphate-buffered saline (PBS) and lysed using 250 μl of RIPA buffer applied to confluent cells on a 24 mm Transwell filter (Corning Costar Corporation, Lowell, Mass.). The lysates were centrifuged at 14,000 rpm for 15 minutes at 4° C. and the supernatant was collected. Thirty microliters of each sample were resolved by electrophoresis on a 10% Bis-Tris polyacrylamide gel (Invitrogen, Carlsbad, Calif.) and transferred to a nitrocellulose membrane. Factor H was detected in the lysates using a polyclonal goat anti-human antibody (Quidel Corp., San Diego, Calif.) diluted 1/100 or a monoclonal antibody to mouse factor H (Santa Cruz Biotechnology, Inc., Santa Cruz, Calif.) diluted 1/500. Appropriate secondary antibodies from Jackson Immunoresearch Laboratories (West Grove, Pa.) were used. Fixation of complement protein C3 fragments to the surface of cells in culture was detected using peroxidase-conjugated goat anti-mouse C3 (MP Biomedicals, Santa Ana, Calif.). Antibody binding was detected by exposing the blot to chemiluminescence reagent (Perkin Elmer LAS, Inc., Boston, Mass.). To detect the binding of factor H to proteins in kidney or cell lysates (Far Western analysis), purified factor H was biotinylated with Sulfo-NHS-Biotin (Pierce, Rockford, Ill.) according to the manufacturer's instructions. The sample proteins were separated by SDS-PAGE, transferred to a nitrocellulose membrane, and they were incubated with 2 μg of biotinylated factor H in PBS, pH 7.4. The binding of factor H to protein bands was then detected with horseradish peroxidase-conjugated streptavidin (Zymed Laboratories, Inc., San Francisco, Calif.) diluted 1/500 in PBS, followed by treatment with the appropriate enzyme chemiluminescence (ECL) substrate.

Protocol for induction of renal I/R. Male C57BL/6J mice (Jackson Laboratories, Bar Harbor, Me.) were used in all experiments. Eight to ten week old mice weighing 20-25 g were anesthetized with 60 mg/kg ketamine plus 10 mg/kg xylazine (both from Vedco, Inc., St. Joseph, Mo.) injected intra-peritoneally. Mice were placed on a heating pad to maintain their body temperature during surgery. Laparotomies were then performed and the renal pedicles were located and isolated by blunt dissection as previously described. See. M. Thurman et al., *J. Immunol.* (2003) 170:1517-1523. The pedicles were clamped with surgical clips (Miltex Instrument Company, Inc., York, Pa.), and occlusion of blood flow was confirmed by visual inspection of the kidneys. The clamps were left in place for 24 minutes and then released. The kidneys were observed for approximately one minute to ensure blood re-flow, then fascia and skin were sutured with 4-0 silk (United States Surgical Corp., Princeton, N.J.). Sham surgery was performed in an identical fashion, except that the renal pedicles were not clamped. The mice were volume resuscitated with 0.5 ml of normal saline and kept in an incubator at 29° C. to maintain body temperature. After 8 or 24 hours the mice were anesthetized, and blood was obtained by cardiac puncture. Laparotomy was performed and the kidneys were harvested. All animal procedures were in adherence to the National Institutes of Health *Guide for the Care* and *Use of Laboratory Animals.*

In order to suppress renal production of annexin 2 after I/R, C57BL/6 mice were injected with antisense oligodeoxynucleotides (ODNs) against annexin 2. The mice were injected with a mixture containing 5 nmol of 3 different antisense ODNs (Biognostik Reference Nos. 1.06412, 2.06413, 3.06414) as known in the art and described in Table 1 below, or control ODNs (Biognostik's "Random Control I" and "Random Control II"). These ODNs were designed and manufactured by Biognostik (Göttingen, Germany). To confirm tubular uptake of ODNs, mice received intraperitoneal injections of 5 nmol fluorescein isothiocyanate-labeled (FITC-labeled) ODN (Biognostik, Gottingen, Germany).

TABLE 1

Antisense Oligonucleotides to Annexin A2

| Sequence Reference | Sequence | SEQ ID NO: |
|---|---|---|
| 1.06412 | 5' -TCT CCA GCA TGT CAT AAG - 3' (784-801 bases of total sequence) | 27 |
| 2.06413 | 5' -GTC TGC CCT TTG CAA G - 3' (594-609 bases of total sequence) | 28 |
| 3.06414 | 5' -CAA TGT CCT GCC TCT G - 3' (273-288 bases of total sequence) | 29 |

Immunofluorescence, immunohistochemistry and direct binding of factor H to tissue sections. Sagittal sections of the kidneys were snap frozen in Tissue-Tek® optimal cutting temperature (OCT) compound (Sakura Finetek, La Jolla, Calif.). Four micrometer sections were cut with a cryostat and stored at −70° C. The slides were later fixed with acetone. Complement protein C3 was detected with a FITC-conjugated anti-mouse C3 antibody (MP Biomedicals, Santa Ana, Calif.) diluted 1:150. Factor H was detected with a polyclonal goat anti-human antibody (Quidel Corp., San Diego, Calif.) diluted 1:200 or a monoclonal antibody to mouse factor H (Santa Cruz Biotechnology, Inc., Santa Cruz, Calif.) diluted 1:200. To detect annexin A2 expression, sections were incubated with a monoclonal antibody for mouse annexin A2 (Zymed Laboratories, Inc., San Francisco, Calif.). Appropriate secondary antibodies from Jackson ImmunoResearch were used. Biotinylated mouse factor H was directly bound to tissue sections by diluting the protein in PBS and incubating it on sections for one hour. The sections were then incubated with FITC-conjugated streptavidin (Zymed Laboratories, Inc., San Francisco, Calif.). In all of these procedures tissue sections were counterstained with hematoxylin (Vector Laboratories, Burlingame, Calif.).

Direct binding of factor H to cells and to immobilized annexin A2. To determine whether factor H binds directly to cells, mouse PTECs were grown on Transwell filters until stable trans-epithelial resistance was obtained. Biotinylated factor H was added to either the apical or basal chamber and incubated for one hour. The cells were then washed with PBS and protein lysates were made as described above. The proteins were separated by SDS-PAGE, and bound factor H was detected using HRP-conjugated streptavidin (Zymed Laboratories, Inc., San Francisco, Calif.), followed by chemi-luminescent detection. To determine whether purified factor H bound directly to annexin A2, enzyme-linked immunosorbent assay (ELISA) plates were coated with 100 ng of purified bovine annexin A2 (Biodesign, Saco, Me.) diluted in 15 mM $Na_2CO_3$/35 mM $NaHCO_3$. After blocking the plates with 1% BSA for 1 hour, 500 ng of biotinylated factor H diluted in PBS containing 3 mM $CaCl_2$ was added to the wells. Unbound factor H was washed off using the same buffer, and bound factor H was detected using HRP-conjugated streptavidin (Zymed, San Francisco, Calif.) followed by 50 μl ABTS solution (ABTS=2,2'-azino-di-(3-ethylbenzthiaoline sulfonic acid). Absorbance was read at 405 nm.

Mass spectroscopy. Binding partners for factor H were isolated by pull-down experiments as described above. After separating the pulled-down proteins by SDS-PAGE and staining them with Coomassie Blue, a band of approximately 39 kilodaltons (kD) molecular weight was identified. Bands were excised and proteins digested in the gel using a modification of the methods of Havlis (J. Havlis et al., "Fast-response proteomics by accelerated in-gel digestion of proteins," *Anal. Chem.* (2003) 75:1300-1306) and Jimenez (C. Jimenez et al., IN-GEL DIGESTION OF PROTEINS FOR MALDI-MS FINGERPRINT MAPPING (John Wiley & Sons, Inc.: Brooklyn, N.Y. (1998)), at pp. 16.4.1-16.4.5). Briefly, bands were crushed using a closed pipette tip and destained twice with a 1:1 mixture of acetonitrile and 100 mM ammonium bicarbonate, then contacted with 100% acetonitrile and dried under vacuum. Samples were reduced with freshly prepared dithiothreitol (1.5 mg/ml) and incubated at 37° C. for 60 minutes. After cooling to 4° C., samples were alkylated in the dark for 45 minutes using a 10 mg/ml solution of iodoacetamide. After washing in a 1:1 mixture of acetonitrile and 100 mM ammonium bicarbonate, samples were dried under vacuum, transferred to clean tubes, and rehydrated in trypsin at 0.2 mg/ml in 50 mM ammonium bicarbonate at 37° C. overnight. The supernatants were then sonicated at room temperature after the addition of 1-2 μl of formic acid, collected, and pooled with one additional extract prepared using 0.1% aqueous trifluoroacetic acid with 60% acetonitrile. Pooled extracts were vacuum-concentrated to a volume of approximately 10 μl and stored at −80° C. until used.

LC-MS/MS analysis of enzymatic digests. Tandem mass spectroscopy analysis was performed at the Mass Spectrometry Core Facility at the University of Colorado Health Sciences Center. Approximately 30% of each in-gel digested samples were analyzed by reverse phase nanospray LC-MS/MS using an Agilent 1100 HPLC 75 μm×15 cm column packed with 5 μm Zorbax C18 particles). Spectra were collected over a m/z range from 350 to 1800 daltons (Da) (Agilent LC/MSD Trap XCT Ultra). Active exclusion was used to access lower abundance peptides, where six precursor ions were selected for fragmentation and then excluded from analysis after two measurements.

Surface Plasmon Resonance. Factor H was immobilized on a CM5 sensor chip. Bovine annexin A2 was diluted in Hank's Buffered Saline with or without 3 mM $CaCl_2$ and injected at the following concentrations: HBS alone (no protein) +3 mM $CaCl_2$ (second line from bottom—no binding); 3.7 μg/ml in HBS+3 mM $CaCl_2$ (third line from bottom); 7.5 μg/ml in HBS+3 mM $CaCl_2$ (fourth line from bottom); 15 μg/ml in HBS+3 mM $CaCl_2$ (fifth line from bottom); 30 μg/ml in HBS+3 mM $CaCl_2$ (top line); and 30 μg/ml in Hank's Buffered Saline without calcium (bottom essentially constant line—no binding). The analyte bound to the chip with high affinity (17 nm), but rapidly dissociated from the chip when calcium was removed from cell.

Statistics. Multiple group comparisons were performed using analysis of variance (ANOVA) and post-test according to Newman-Keuls, using the GraphPad Prism™ software package (GraphPad Software, Inc., La Jolla, Calif.). A P value of less than 0.05 was considered statistically significant. Results are reported as mean±standard error (SE).

Results

Figure 1B:
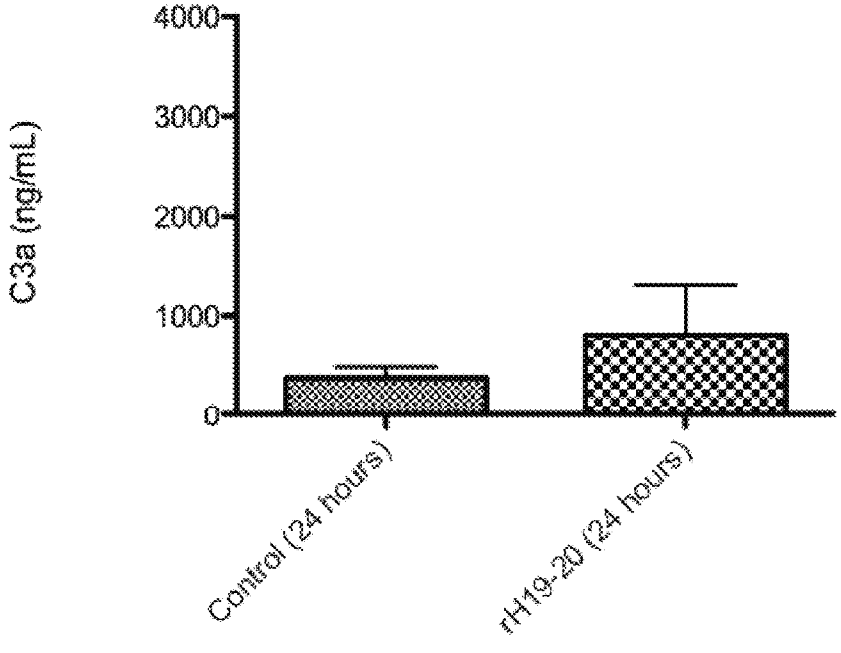
Figure 1C:
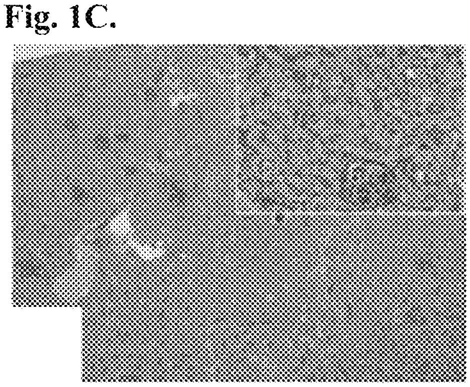
Figure 1D:
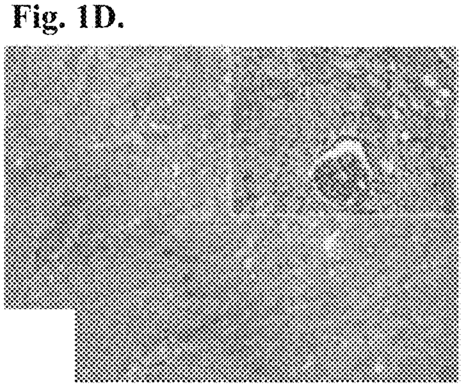
Figure 1E:
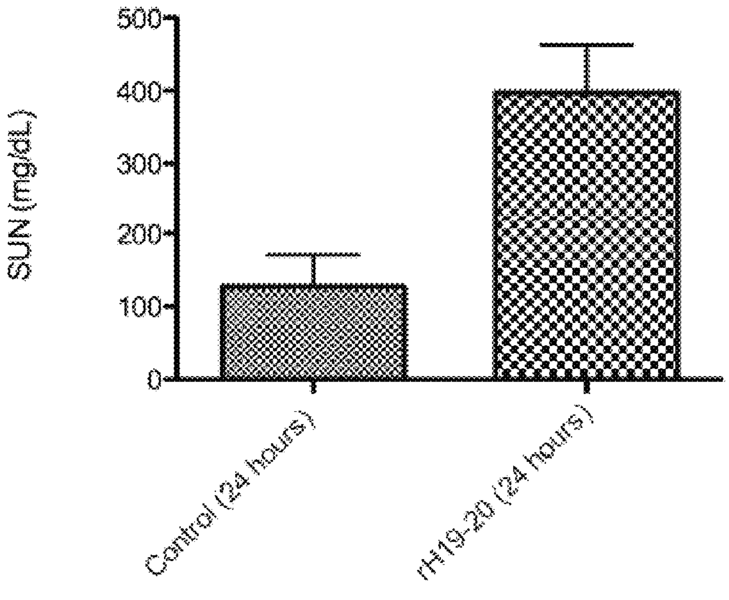

Factor H limits complement mediated injury after renal I/R. Complement protein C3 is deposited along the basolateral aspect of tubules in the outer medulla after renal I/R. J. M. Thurman et al., (2006) *J. Clin. Invest.* 116:357-368; W. Zhou et al., (2000) *J. Clin. Invest.* 105:1363-1371. To test whether circulating factor H is functionally important after renal I/R, we subjected mice to renal I/R then injected them with a recombinant protein that competitively blocks binding of factor H at the carboxy terminus. Mice injected with this protein showed greater systemic C3a than controls (FIG. 1A) after 8 hours of reperfusion. Levels were no different than control animals injected with an equal volume of PBS by 24 hours of reperfusion (FIG. 1B), suggesting that factor H is functionally blocked within 8 hours of reperfusion in this model. Renal I/R typically causes injury of the tubules in the outer medulla (FIG. 1C). In mice treated with rH19-20 the injured tubules extended into the cortex (FIG. 1D). Serum urea nitrogen (SUN) levels were also significantly higher in mice treated with rH19-20 (FIG. 1E), indicating worse functional impairment in mice treated with rH19-20. Although circulating factor H does not fully prevent complement activation in the kidney after I/R, this experiment demonstrates that it does function to limit complement-mediated injury during reperfusion.

Native factor H does not protect PTECs at baseline. PTECs were grown in primary culture. The cells were then incubated with 10% normal mouse serum in the presence or absence of rH19-20. Finally, the cells were stained with an FITC-conjugated antibody to mouse C3 protein, and complement activation on the cell surface was measured by FACS analysis. Treatment with rH19-20 did not cause increased deposition of complement protein C3.

Figure 2A:
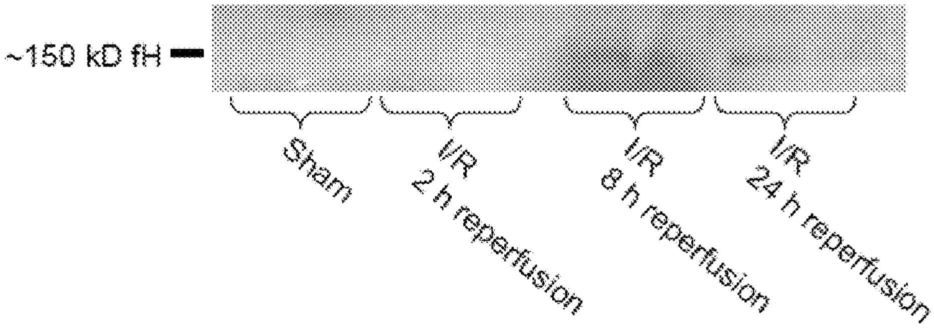
FIGS. 2A-2B. Factor H levels increase in the kidney after I/R. Mice were subjected to renal I/R and Western blot analysis was performed to measure levels of factor H within the kidney.
Figure 2B:
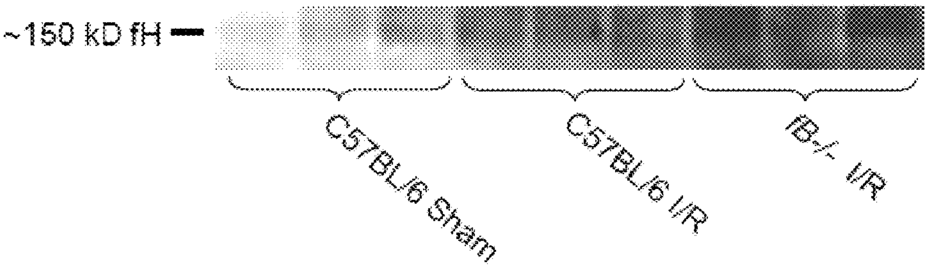
Figure 3A:
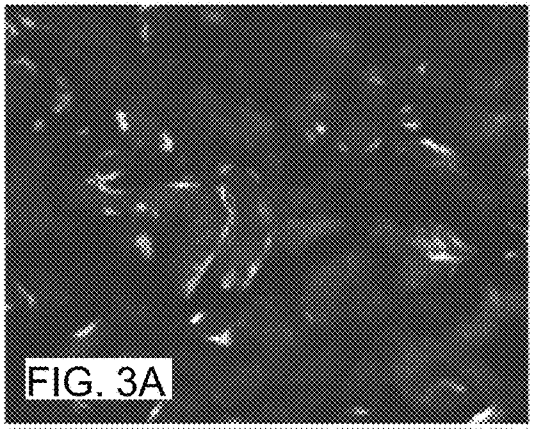
FIGS. 3A-3F. Tissue bound factor H does not co-localize with C3 deposits. Mice were subjected to renal I/R, and immunofluorescence microscopy was performed to identify factor H and C3.
Figure 3B:
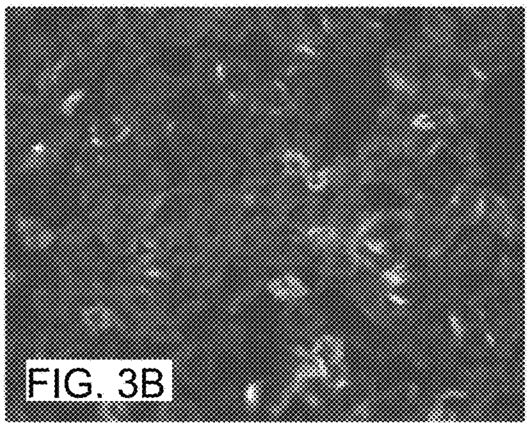
Figure 3C:
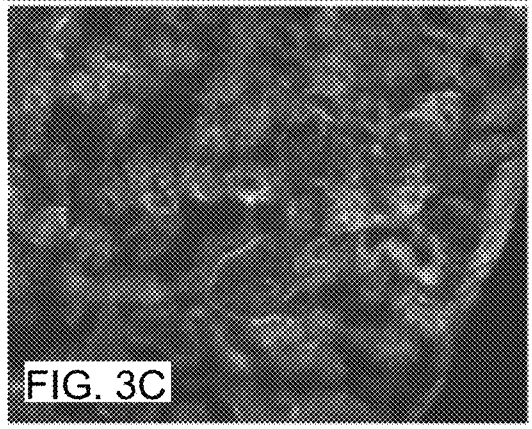
Figure 3D:
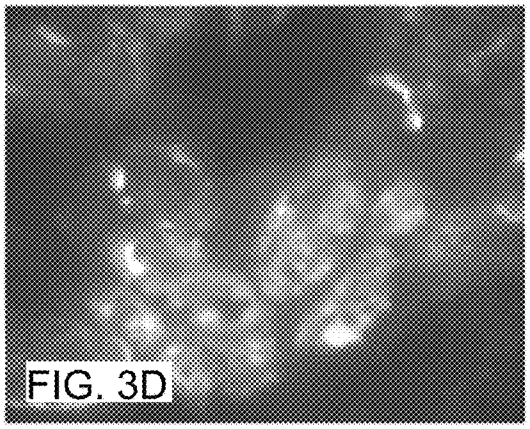
Figure 3E:
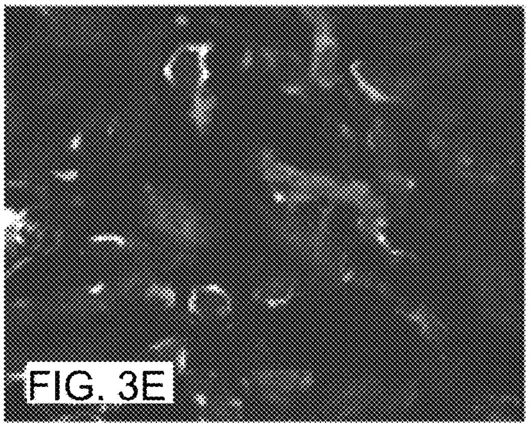
Figure 3F:
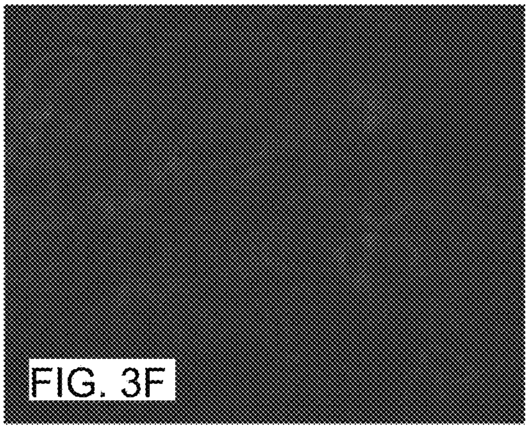

Factor H accumulates in the tubulointerstitium after I/R but does not co-localize with C3. Given the functional importance of factor H during reperfusion, we next examined the kidneys for the presence of factor H. C3 deposits are seen on injured tubules within 6 hours of I/R and peak after 24 hours of reperfusion in our model. See J. M. Thurman et al., *J. Clin. Invest.* (2006) 116:357-368. Western blot analysis of kidney lysates demonstrates that factor H levels within the kidney rise within 8 hours of reperfusion (FIG. 2A). It has been proposed that factor H binds to C3b deposited on anionic surfaces (S. Meri et al., *Proc. Nat'l Acad. Sci. USA* (1990) 87:3982-3986; S. Meri et al., *Biochem. Biophys. Res. Comm.* (1994) 198:52-59, but factor B deficient mice subjected to renal I/R [in which no C3 is deposited on the tubules after I/R (J. M. Thurman et al., *J. Immunol.* (2003) 170:1517-1523)] demonstrated factor H levels equivalent to those in wild-type mice after renal I/R (FIG. 2B). Furthermore, dual staining for factor H and C3d (FIGS. 3A-3F) demonstrated that during reperfusion the tubulointerstitial factor H does not co-localize with C3d. This may be due to the ability of the bound factor H to prevent AP activation, but it suggests that factor H does not require C3d in order to bind within post-ischemic kidney when other appropriate ligands are present.

Annexin 2 is expressed in the kidneys during reperfusion and is a binding ligand for factor H. To determine whether protein ligands may mediate the increased binding of factor H seen during reperfusion, we performed Far-Western analysis of kidney lysates using purified factor H (FIG. 4A), and found that factor H bound to proteins present in the post-ischemic lysates that were not evident in the lysates of unmanipulated kidneys. We used factor H to pull down binding partners in the lysates (FIG. 4B), and again found that new binding partners were present in the lysates of post-ischemic kidneys.

Figure 4A:
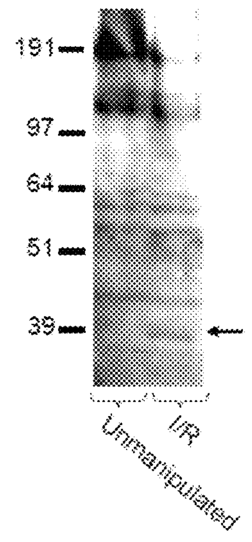
FIGS. 4A-4C. Purified factor H binds to Annexin A2 expressed in the kidney after I/R. Factor H was purified by heparin chromatography, and its purity was verified by Coomassie staining and Western blot analysis.
Figure 4B:
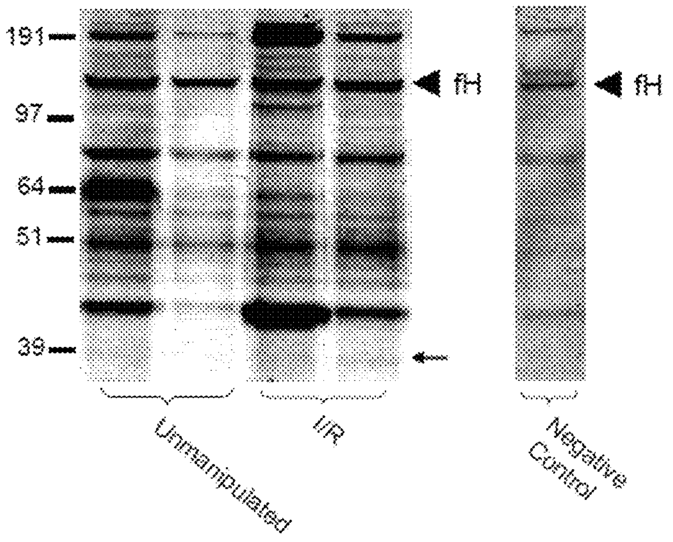
Figure 4C:
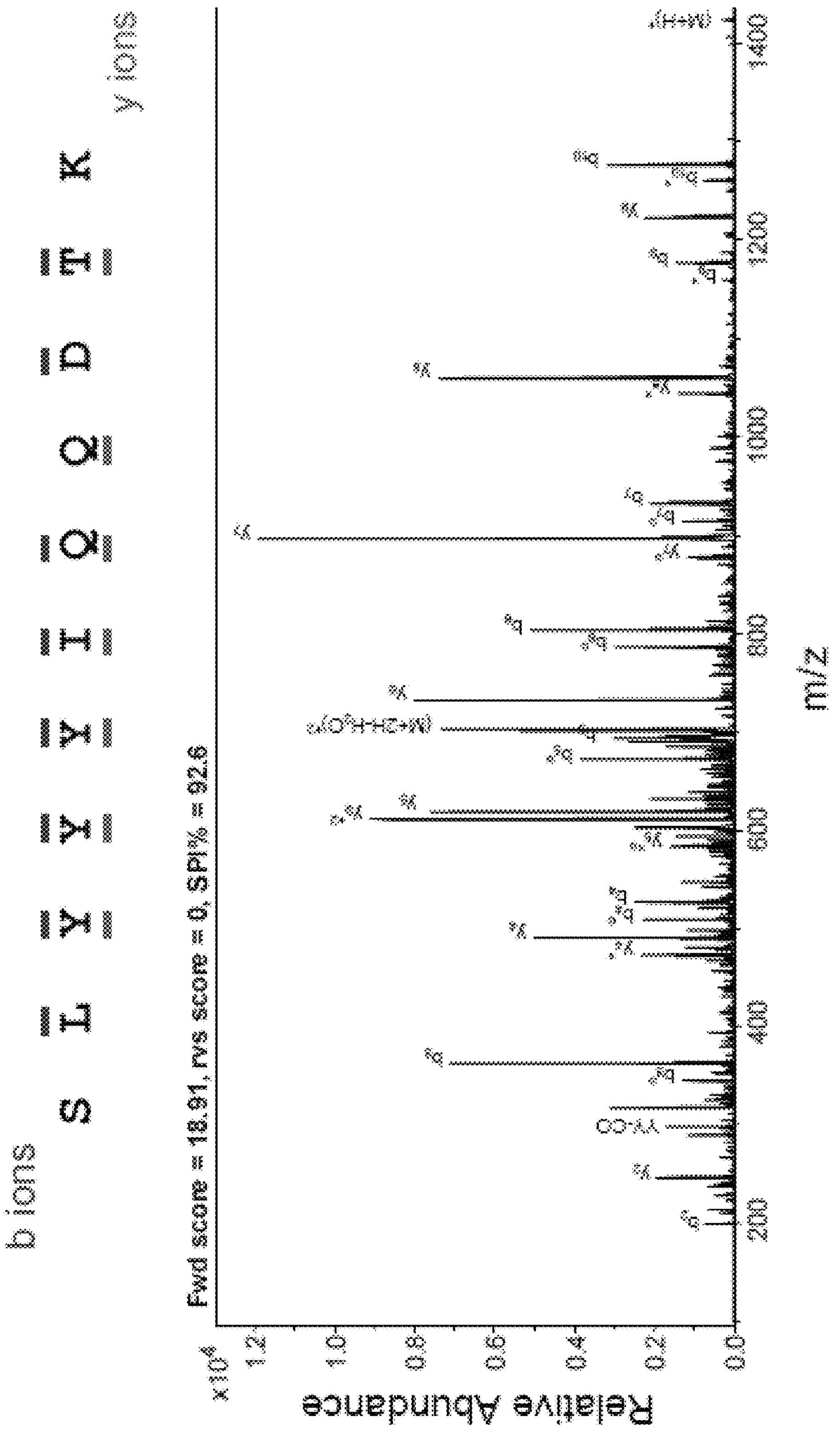

We examined the ~39 kD binding partner by tandem mass spectroscopy (FIG. 4C) and identified the protein as annexin A2. Typically, at least 2 peptide hits are sought to confirm a protein's identity. We obtained 6 unique peptides for annexin A2, and three were manually confirmed. FIG. 4C shows the MS spectrum for one of the peptides. The mass of the peptide is 1422.0527 a.m.u., and the observed peak chosen for fragmentation was at m/z 711.53, corresponding to a doubly-charged ion. The peptide sequence is shown and the b- and y-type fragment ions that were observed are indicated by a line over or under the letter representing the amino acid. The data was searched against the SwissProt database (human mouse taxonomy) using SpectrumMill from Agilent Technologies (Santa Clara, Calif.). The search score was 18.91. The data was also searched against a reverse database and that score was 0, indicating that the data is of very good quality. The single photon ionization percentage (SPI %) (a measure of how much of the ion current is accounted for by theoretically expected peaks) for this spectrum was 92.6, suggesting that the dominant ions conform to those expected for this sequence.

Figure 5A:
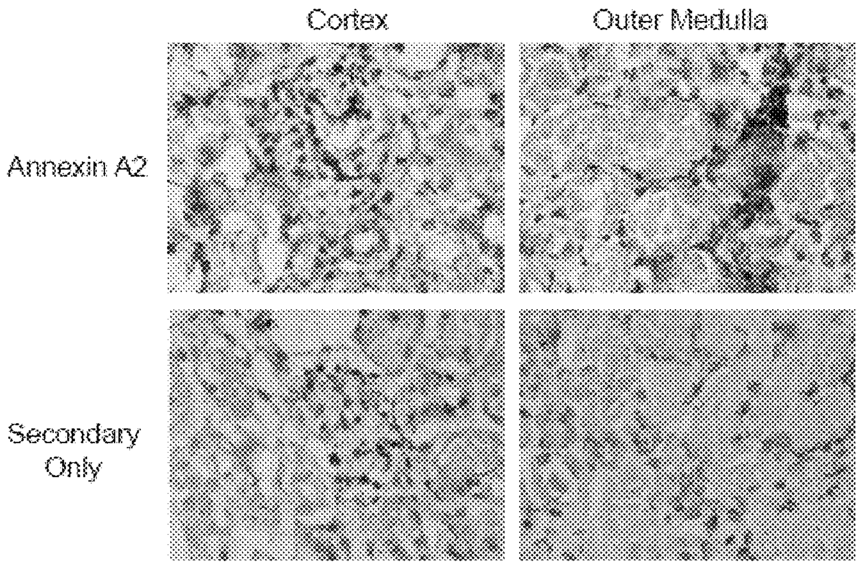
FIGS. 5A-5B. Annexin A2 is expressed on injured tubules after I/R, and factor H pulls down annexin A2 in kidney lysates. Immunohistochemistry for annexin A2 was performed on sections of kidneys subjected to I/R.
Figure 5B:
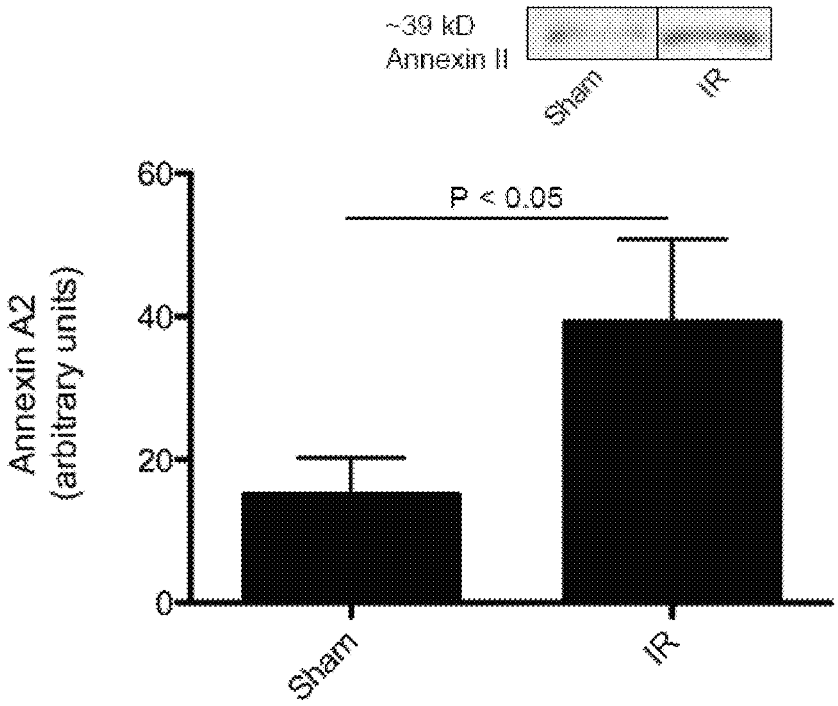
Figure 6:
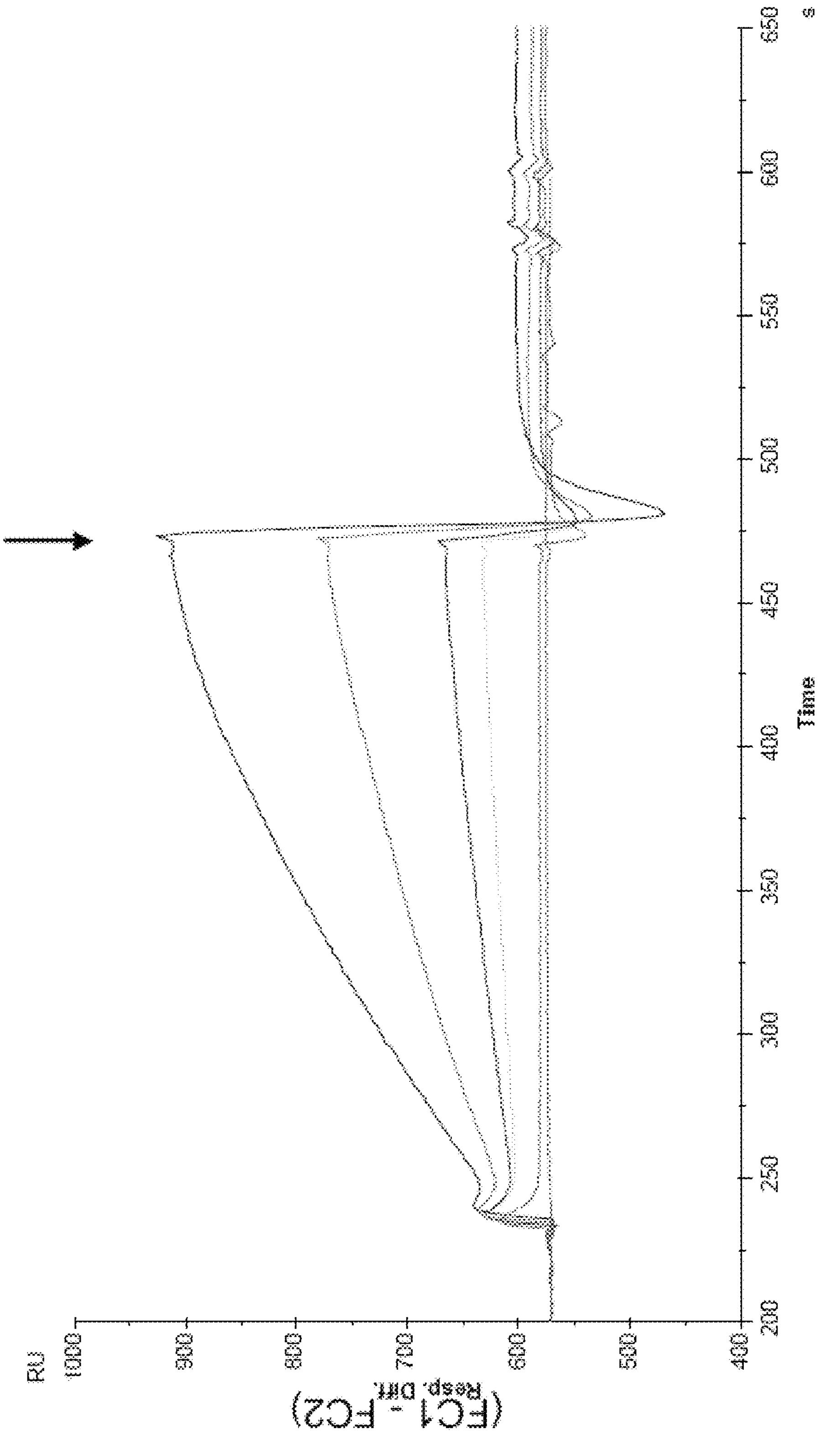
FIG. 6. Surface plasmon resonance demonstrates that annexin A2 binds to factor H with high affinity. Factor H was immobilized on a CM5 sensor chip. Bovine annexin A2 was diluted in Hank's Buffered Saline with or without 3 mM $CaCl_2$ and injected at the following concentrations: HBS alone (no protein) +3 mM $CaCl_2$ (second line from bottom—no binding); 3.7 μg/ml in HBS+3 mM $CaCl_2$ (third line from bottom); 7.5 μg/ml in HBS+3 mM $CaCl_2$ (fourth line from bottom); 15 μg/ml in HBS+3 mM $CaCl_2$ (fifth line from bottom); 30 μg/ml in HBS+3 mM $CaCl_2$ (top line); and 30 μg/ml in Hank's Buffered Saline without calcium (bottom essentially constant line—no binding). The analyte bound to the chip with high affinity (17 nm), but rapidly dissociated from the chip when calcium was removed from cell.

Annexin A2 is a $Ca^{2+}$-regulated phospholipid binding protein. See V. Gerke et al., *Physiol. Rev.* (2002) 82:331-371. Extracellular annexin A2 functions as a surface bound receptor for several different molecules, including plasminogen and tissue plasminogen activator. See K. A. Hajjar et al., *J. Biol. Chem.* (1994) 269:21191-21197. It has previously been reported that annexin A2 is expressed by regenerating tubules after toxic and ischemic injury of the kidney. See C. W. Cheng et al., *Kidney Intl* (2005) 68:2694-2703. We detected annexin A2 in the glomeruli and in injured renal tubules after I/R (FIG. 5A). Western blot analysis of proteins pulled down by purified factor H using a monoclonal antibody for annexin A2 confirmed that factor H bound to annexin A2 in the lysates of post-ischemic kidneys (FIG. 5B). When a recombinant fragment of factor H containing short consensus repeats 19 and 20 (rH 19-20) was added to the pull-down reaction it blocked the binding of factor H and annexin A2 (FIG. 5B), indicating that this protein-protein interaction involves the carboxyl-terminus of factor H.

Factor H binds directly to annexin A2 in a calcium dependent fashion. To determine whether factor H binds directly to annexin A2 or whether bridging molecules are required, surface plasmon resonance was performed. Factor H was coupled to a CMS chip, and bovine annexin A2 was introduced. The annexin A2 bound to the chip with high affinity in the presence of calcium-containing buffer. When the buffer was changed to a calcium-free buffer, the annexin A2 rapidly dissociated from the chip. Control protein (annexin A5) did not bind to the factor H-coupled chip.

Targeted factor H prevents complement activation after renal I/R. Based upon the above findings, we hypothesized that the inability of native factor H to prevent complement activation within the kidney was due to insufficient expression of binding ligands at this location. To overcome this limitation we employed a recombinant protein that targets the inhibitory region of mouse factor H specifically to sites of C3d deposition. This protein is comprised of the C3d binding region of complement receptor 2 linked to the first four SCRs (the complement inhibitory region) of factor H (referred to as "CR2-fH"), a strategy that has previously been utilized for the targeting of complement inhibitors to sites of complement activation. See H. Song et al., *J. Clin. Invest.* (2003) 111:1875-1885; C. Atkinson et al., *J. Clin. Invest.* (2005) 115:2444-2453. Since they contain the same inhibitory region, any functional superiority of the CR2-fH compared with endogenous factor H is most likely attributable to differential binding of the protein to C3d on the specific surface in question.

Several in vitro assays are used to assess alternative pathway activation. The lysis of erythrocytes by normal human serum is critically dependent on the interaction of factor H in the serum with anions on the erythrocyte surface. See V. P. Ferreira et al., *J. Immunol.* (2006) 177:6308-6316. Sheep erythrocytes, for example, are more sensitive to lysis by human serum than human erythrocytes are because of a stronger interaction of factor H with the human cells. Zymosan particles have frequently been used to activate the alternative pathway in vitro, and abundant C3 is deposited on the particles when incubated with serum. See J. M. Thurman et al., *Mol. Immunol.* (2005) 42:87-97. Although factor H present in the serum does not prevent activation of the alternative pathway on the zymosan surface (M. K. Pangburn et al., *J. Immunol.* (2000) 164:4742-4751), the CR2-targeted factor H does (FIGS. 4A-4B).

Figure 7A:
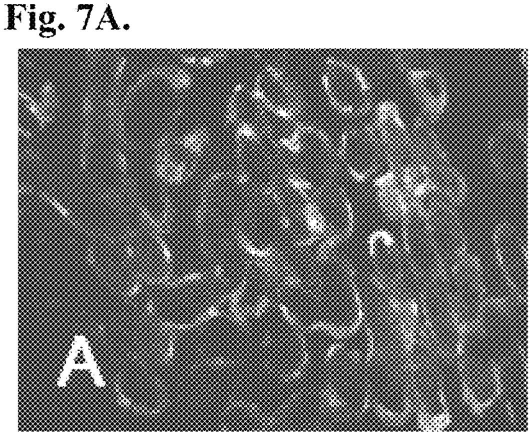
FIGS. 7A-7D. CR2-fH prevents complement activation after renal I/R. CR2-fH is a recombinant fusion protein that uses the C3d-binding region of CR2 to target the complement-inhibitory region of factor H to sites of C3d deposition. Mice were subjected to renal I/R and were then injected with vehicle or with 250 μg of CR2-fH. (A-B) Immunofluorescence microscopy for C3 revealed that mice treated with vehicle (FIG. 7A) demonstrated tubular deposition of C3, whereas only sparse areas of C3 were seen in mice treated with CR2-fH (FIG. 7B). Treatment with CR2-fH decreased tubular deposition of C3 compared to control mice treated with vehicle alone (FIG. 7C) and attenuated the development of renal injury after I/R as measured by SUN (serum urea nitrogen) levels (FIG. 7D).
Figure 7B:
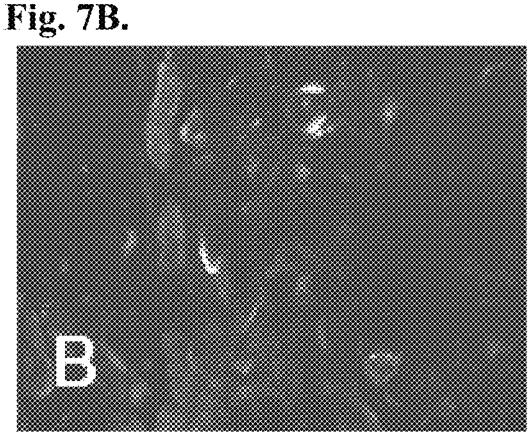
Figure 7C:
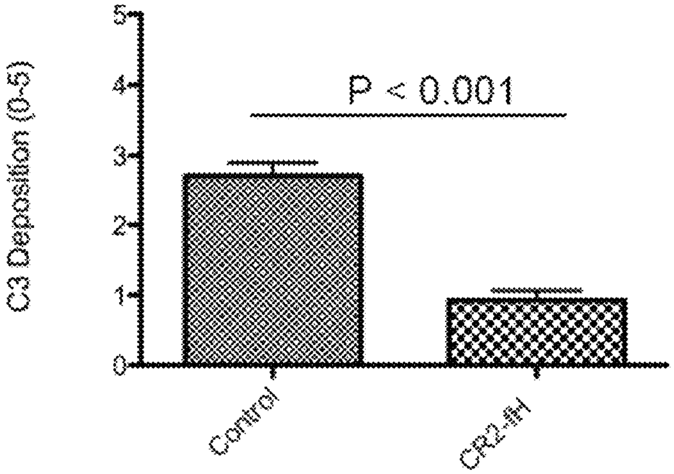
Figure 7D:
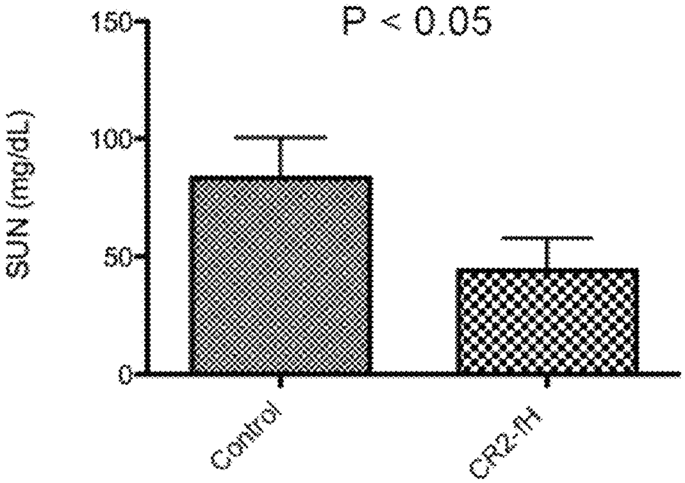

We subjected mice to renal I/R and injected them with 150 μg of CR2-targeted factor H after 15 minutes of reperfusion. We found that the CR2-targeted factor H attenuated tubulointerstitial complement activation after renal I/R (FIGS. 7A-7C) and ameliorated renal injury (FIG. 7D). Thus, the targeted factor H more effectively prevented complement activation on the post-ischemic kidney than native factor H.

Targeted factor H prevents fixation of C3 to the basolateral surface of hypoxic PTECs.

PTECs were next grown on Transwell™ filters until they formed a stable monolayer. Chemical hypoxia was induced by treating the cells with Antimycin A. See J. M. Thurman et al., *J. Am. Soc. Nephrol.* (2006) 17:707-715. The cells were then exposed to 10% serum for one hour, and lysates of the cells were prepared. Western blot analysis for complement protein C3 demonstrated that C3 degradation fragments were fixed to the cell surface in spite of the factor H in the serum. The addition of CR2-fH to the serum prevented fixation of C3 to the cells, but the addition of superphysiologic concentrations of native factor H did not.

Discussion

Circulating factor H does not prevent alternative pathway activation in the kidney after I/R. We found, however, that levels of factor H in the kidney increased during reperfusion, and that treatment with a competitive inhibitor of the binding region of factor H caused greater complement activation and greater renal injury after I/R. These results indicate that native factor H does effectively limit alternative pathway activation during reperfusion. Although factor H contains binding sites for C3d, the tissue bound factor H did not co-localize with C3d, and factor H was also accumulated in the kidneys of complement deficient mice subjected to renal I/R. Furthermore, proteomic analysis indicated that other proteins expressed in the post-ischemic kidney, such as annexin A2, can bind factor H with high affinity. Thus, factor H does not prevent complement activation in the kidney after I/R, but the generation of factor H binding ligands in post-ischemic tissue is a critical mechanism by which inflammation is limited.

We next treated mice with a recombinant protein that specifically targets factor H to sites of deposited C3d (CR2-fH). This agent almost completely prevented tubulointerstitial complement activation after renal I/R and ameliorated the development of renal injury. Thus, this agent was much more effective than endogenous factor H at preventing alternative pathway activation after renal I/R. This finding further illustrates that complement inhibition by native factor H in the kidney is limited by the protein's affinity for this surface. We specifically examined the interactions between factor H and hypoxic tubular epithelial cells because complement activation on this surface occurs predominantly through the alternative pathway. Our results, however, have several important implications regarding the general mechanisms by which the complement system is controlled.

The ability of factor H to discriminate between host cells and invasive pathogens has been attributed to binding of the factor H molecule to negatively charged molecules such as sialic acid and glycosaminoglycans that are displayed on the surface of host cells. See S. Meri et al., *Proc. Nat'l Acad. Sci. USA* (1990) 87:3982-3986. In diseases such as AMD and aHUS the anatomic restriction of disease has been attributed to: i) efficient complement inhibition by factor H on the negatively charged basement membranes in the eye and kidney, and ii) the absence of other complement regulatory proteins on these surfaces. The factor H variants that are strongly associated with the risk of these diseases demonstrate reduced affinity for polyanions (G. S. Hageman et al., *Proc. Nat'l Acad. Sci. USA* (2005) 102:7227-7232; A. P. et al., *J. Biol. Chem.* (2007) 282:10894-10900; M. C. Pickering et al., *Clin. Exp. Immunol.* (2008) 151:210-230), perhaps explaining the predisposition to disease in the eye and kidney. The onset of AMD is usually in the $6^{th}$ decade of life, however, and aHUS can be triggered by infections or other types of endothelial injury (M. C. Pickering and H. T. Cook, "Translational mini-review series on complement factor H: renal diseases associated with complement factor H—novel insights from humans and animals," *Clin. Exp. Immunol.* (2008) 151:210-230). Furthermore, aHUS is also associated with congenital mutations in MCP. These observations suggest complex interactions between factor H and host tissues.

Little, however, is known about different binding ligands for factor H expressed within these tissues. Our data indicates that surface proteins also mediate the binding of factor H to host cells, and that the cells actively modulate expression of these binding ligands. In addition to polyanions, the affinity of factor H for each tissue type may be determined by its interactions with numerous different binding ligands.

The alternative pathway of complement has emerged as an important trigger of inflammation in a number of different diseases. See J. M. Thurman et al., *J. Immunol.* (2006) 176:1305-1310. Pathologic alternative pathway activation is frequently due to congenital or acquired defects in the proteins that regulate the complement system. Cellular injury may also foster alternative pathway activation by reducing local expression of complement regulatory proteins, suggesting that complement inhibition on a given tissue or cell type is not a static characteristic of that surface, but may significantly change during injury or recovery.

Distinct tissues express different combinations of the membrane bound complement inhibitors, and factor H likely has different affinities for various cell types. Consequently, congenital defects in complement regulatory proteins may render particular organs susceptible to complement mediated injury, such as the eye (G. S. Hageman et al., *Proc. Nat'l Acad. Sci. USA* (2005) 102:7227-7232; A. P. Sjöberg et al., *J. Biol. Chem.* (2007) 282:10894-10900) and the kidney (M. C. Pickering et al., *J. Exp. Med.* (2007) 204: 1249-1256; M. C. Pickering et al., *Nature Genet.* (2002) 31(4):424-428). Based upon the results presented in the current study, a reduction or increase in the affinity expression of ligands for factor H may also underlie the activation or control of the alternative pathway in disease.

Example 2

Effect of Annexin 2 During Renal Failure

Experimental

Renal ischemia/reperfusion protocol. Eight to ten week old male C57BL/6J mice (Jackson Laboratories) mice weighing 20-25 g were anesthetized with 60 mg/kg ketamine plus 10 mg/kg xylazine (Vedco, Inc., St. Joseph, Mo.) injected intra-peritoneally. Mice were placed on a heating pad to maintain body temperature during surgery. Laparotomies were then performed and the renal pedicles were located and isolated by blunt dissection as known in the art. The pedicles were clamped with surgical clips (Miltex Instrument Company), and occlusion of blood flow was confirmed by visual inspection of the kidneys. The clamps were left in place for 24 minutes and then released. The kidneys were observed for approximately one minute to ensure blood re-flow, then fascia and skin were sutured with 4-0 silk (United States Surgical). Sham surgery was performed in an identical fashion, except that the renal pedicles were not clamped. The mice were volume resuscitated with 0.5 ml of normal saline and kept in an incubator at 29° C. to maintain body temperature. After eight or 24 hours the mice were anesthetized, and blood was obtained by cardiac puncture. Laparotomy was performed and the kidneys were harvested.

Knock-down of annexin A2 production in vivo using anti-sense oligonucleotides. In order to suppress renal production of Annexin 2 after I/R, C57BL/6 mice were injected with antisense oligodeoxynucleotides (ASOs) against Annexin 2. The mice were injected intra-peritoneally with a mixture containing 5 nmol of 3 different antisense ASOs or control ODNs. See Table 1 herein. These ODNs were designed and manufactured by Biognostik (Gottingen, Germany). Mice received injections of the ASOs two days prior to undergoing renal I/R and on the morning of renal I/R.

Measurement of C3a. Plasma C3a was measured as a marker of complement activation in mice subjected to renal I/R after treatment with ASO to Annexin A2 or with control ASO. Plasma samples were taken from mice after 8 hours of reperfusion, and C3a levels were measured by enzyme linked immunosorbent assay (ELISA) according to the manufacturer's instructions (BD Pharmingen). Briefly, ELISA platers were coated with 200 ng of capture antibody as known in the art. After blocking the plates with 1% bovine serum albumin, the plasma samples were diluted 1/50 in PBS and applied to the plates for 1 hour at room temperature. A detection antibody was then applied to the plate (100 µl of antibody diluted to 1.0 µg/mL), followed by detection with streptavidine-HRP (diluted 1:2500) and ABTS. Fluorescence was then read at 405 nm on a plate reader.

In vitro analysis of complement activation on tubular epithelial cells. To measure complement activation on the surface of renal tubular epithelial cells (TECs), murine TECs were grown to confluence. The cells were released from the plates by treatment with Accutase® (Innovative Cell Technologies, Inc.) and washed in PBS. For complement activation experiments, the cells were then incubated in 10% mouse serum at 37° C. for 20 minutes. In some experiments 10 µg of rH 19-20 or 11.2 µg of Annexin A2 was added to the reaction. The cells were then washed in PBS and incubated with a FITC conjugated antibody to mouse C3. Cells were then washed and resuspended in 500 µL of PBS, run on a FACSCalibur™ machine (BD Biosciences), and the results were analyzed with CellQuest Pro™ software (BD Biosciences). Surface fluorescence for C3 was interpreted as complement activation on the cell surface.

Results

Figure 8:
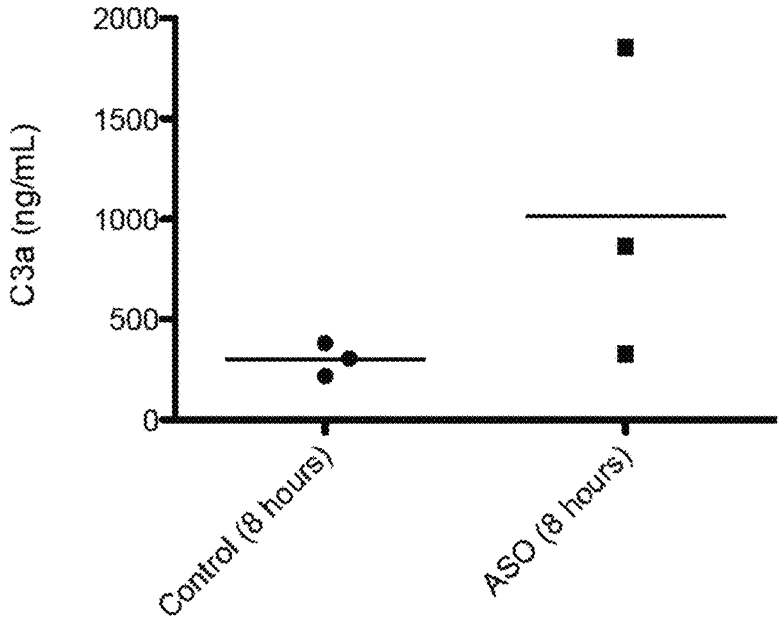
FIG. 8. Mice were treated with ASOs to Annexin A2 (Column "ASO (8 hours)" or with control ASOs (Column "Control (8 hours)"), and were then subjected to renal I/R. After eight hours of reperfusion plasma samples were obtained, and C3a was measured by ELISA, as described herein and known in the art. Levels of C3a in mice treated with ASOs to Annexin A2 were higher than those in control animals, demonstrating that Annexin A2 functions to limit complement activation after renal I/R.

As shown in FIG. 8, mice in which Annexin A2 production is blocked display greater complement activation after renal I/R. Mice were treated with ASOs to Annexin A2 or with control ASOs, and were then subjected to renal I/R. After eight hours of reperfusion plasma samples were obtained, and C3a was measured by ELISA. Levels of C3a in mice treated with ASOs to Annexin A2 were higher than those in control animals. Without wishing to be bound by any theory, these results demonstrate that Annexin A2 functions to limit complement activation after renal I/R.

Figure 9:
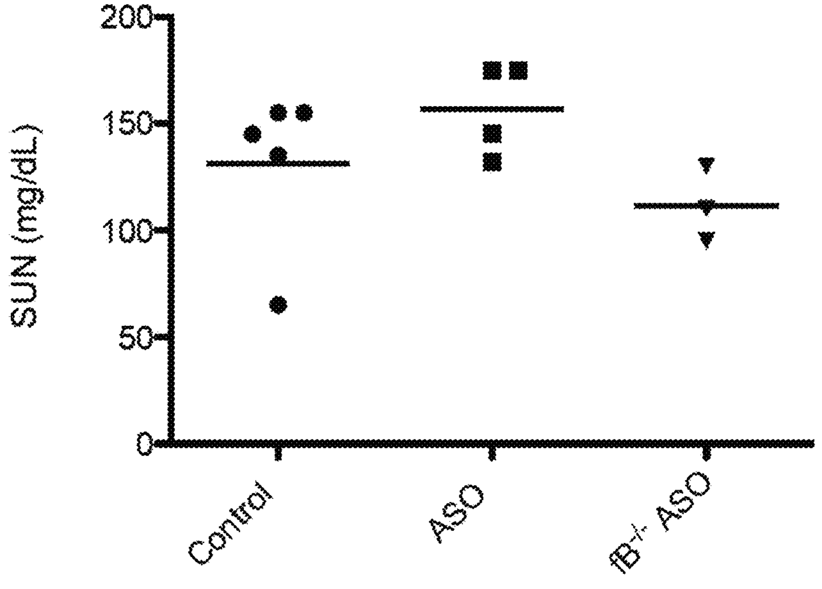
FIG. 9. Mice were treated with ASO to Annexin A2 or with control ASOs, and were then subjected to renal I/R. After twenty-four hours of reperfusion the mice were sacrificed, and serum urea nitrogen (SUN) was measured, by methods known in the art, as a marker of renal function. SUN levels in mice treated with ASOs to Annexin A2 were higher than those in control animals, demonstrating that Annexin A2 functions to limit renal injury after renal I/R. See Column "ASO.:" SUN levels in complement deficient mice (deficient in factor B, or $fB^{-/-}$ mice) that were treated with the ASOs to Annexin A2 were not higher than control mice, indicating that the ASOs to Annexin A2 require an intact complement system in order to cause renal injury after I/R. See Column "$fB^{-/-}$ ASO."

As shown in FIG. 9, mice in which Annexin A2 production is blocked display more severe renal injury after renal I/R than control mice. Mice were treated with ASO to Annexin A2 or with control ASOs, and were then subjected to renal I/R. After twenty-four hours of reperfusion the mice were sacrificed, and serum urea nitrogen (SUN) was measured as a marker of renal function. SUN levels in mice treated with ASOs to Annexin A2 were higher than those in control animals. Without wishing to be bound by any theory, the results demonstrate that Annexin A2 functions to limit renal injury after renal I/R. Furthermore, SUN levels in complement deficient mice (deficient in factor B, or fB−/− mice) that were treated with the ASOs to Annexin A2 were not higher than control mice, indicating that the ASOs to Annexin A2 require an intact complement system in order to cause renal injury after I/R.

Figure 10:
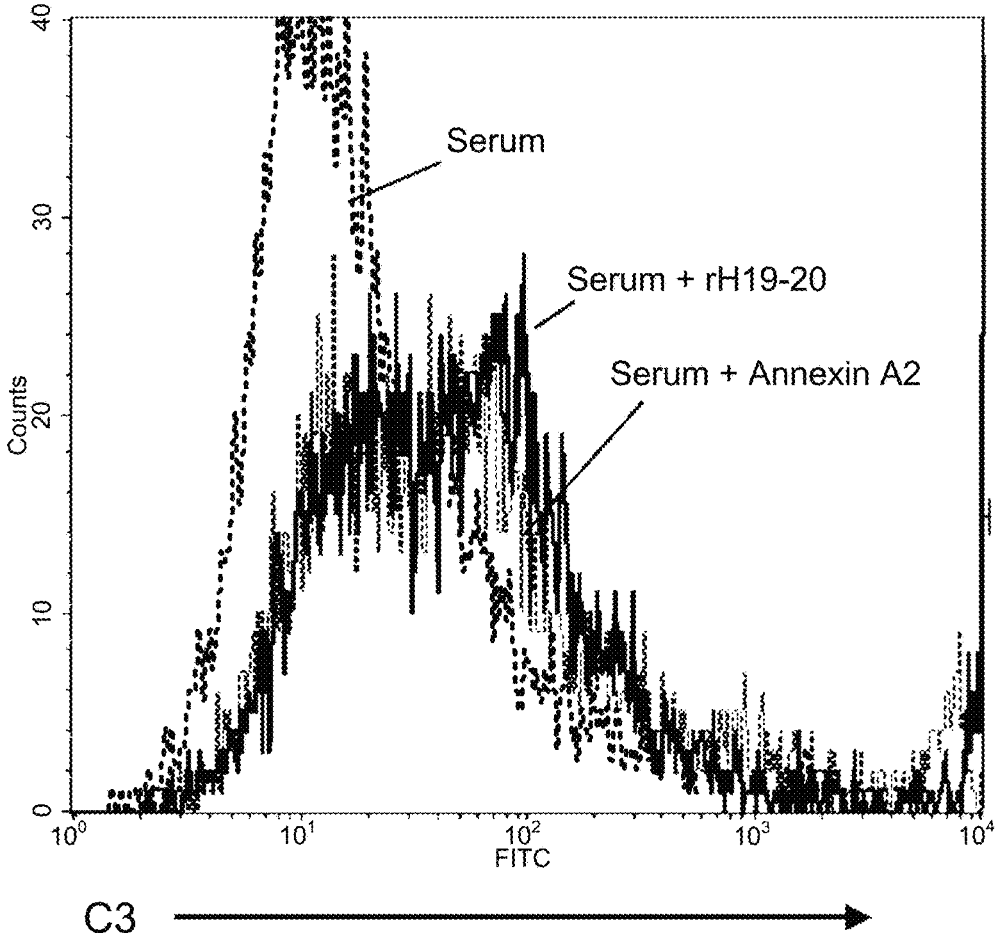
FIG. 10. Renal tubular epithelial cells were grown in culture and were then exposed to 10% mouse serum (shaded curve). Treatment of the cells with rH19-20 blocked protection of the cells by factor H present within the serum, thereby enhancing the deposition of C3 on the cell surface (black line). The addition of purified Annexin A2 to the cell supernatant had a similar effect (dashed line). The addition of both rH19-20 and Annexin A2 caused a similar degree of complement activation on the cells than was obtained with either reagent alone.

As shown in FIG. 10, purified Annexin A2 can enhance complement activation on cell surfaces by blocking the interaction of factor H with the cell surface. Renal tubular epithelial cells were grown in culture and were then exposed to 10% mouse serum (shaded curve).

Treatment of the cells with rH19-20 blocked protection of the cells by factor H present within the serum, thereby enhancing the deposition of C3 on the cell surface (solid line). The addition of purified Annexin A2 to the cell supernatant had a similar effect (dashed line). The addition of both rH19-20 and Annexin A2 caused a similar degree of complement activation on the cells than was obtained with either reagent alone. Without wishing to be bound by any theory, these data can be interpreted as reflecting a competition of factor H away from the cell surface due to Annexin A2.

Although the foregoing has been described in some detail by way of illustration and example for purposes of clarity of understanding, it is apparent to those skilled in the art that certain changes and modifications will be practiced without departing from the disclosed scope. Therefore, the description and examples should not be construed as limiting the scope provided herein.

What is claimed is:

1. A composition for modulating alternative complement activity, the composition comprising a fusion protein comprising an anti-annexin A2 antibody or an antigen-binding fragment thereof fused to a complement inhibitor selected from the group consisting of decay-accelerating factor (DAF), factor H, membrane cofactor protein (MCP), CD59, complement receptor 1(CR1), and mouse complement receptor 1-related gene/protein y (Crry protein), and a pharmaceutically acceptable carrier.

2. The composition of claim 1, wherein said modulating alternative complement activity comprises inhibiting alternative complement activity.

3. The composition of claim 1, wherein the antigen-binding fragment of an anti-annexin A2 antibody comprises an Fab, Fab', or $F(ab')_2$ fragment.

4. The composition of claim 1, wherein the complement inhibitor is DAF.

5. The composition of claim 1, wherein the complement inhibitor is factor H.

6. The composition of claim 1, wherein the complement inhibitor is MCP.

7. The composition of claim 1, wherein the complement inhibitor is CD59.

8. The composition of claim 1, wherein the complement inhibitor is CR1.

9. The composition of claim 1, wherein the complement inhibitor is mouse Crry protein.

10. A method of modulating alternative complement activity in an individual, the method comprising administering to an individual in need thereof a composition comprising the fusion protein of claim 1.

11. The method of claim 10, wherein the individual is a mammal.

12. The method of claim 10, wherein the mammal is a human, a mouse, or a rat.

13. The method of claim 10, wherein alternative complement activity is inhibited in the individual.

14. The method of claim 10, wherein the administering is orally or by injection.

15. The method of claim 10, wherein the antigen-binding fragment comprises an Fab, Fab', or $F(ab')_2$ fragment.

16. A composition comprising a fusion protein and a pharmaceutically acceptable carrier, wherein said fusion protein comprises an anti-annexin A2 antibody or an antigen-binding fragment thereof, and a biologically active fragment of human DAF, wherein said biologically active fragment of human DAF comprises at least one of a SCR domain and a O-glycosylated serine/threonine-rich domain of a full-length human DAF.

17. The composition of claim 16, wherein the biologically active fragment of human DAF comprises:

one or more of: a fragment comprising amino acids 35-96 of SEQ ID NO: 17, a fragment comprising amino acids 96-160 of SEQ ID NO: 17, a fragment comprising amino acids 161-222 of SEQ ID NO: 17, a fragment comprising amino acids 223-285 of SEQ ID NO: 17, and a fragment comprising amino acids 287-353 of SEQ ID NO: 17.

18. The composition of claim 16, wherein the biologically active fragment of human DAF comprises amino acids 35-353 of SEQ ID NO: 17.

19. The composition of claim 16, wherein the biologically active fragment of human DAF comprises amino acids 35-285 of SEQ ID NO: 17.

20. A composition that comprises a fusion protein and a pharmaceutically acceptable carrier, wherein said fusion protein comprises an anti-annexin A2 antibody or an antigen-binding fragment thereof, and a biologically active fragment of human factor H, wherein the biologically active fragment of human factor H comprises SCRs 1 to 4, SCRs 1 to 8, SCRs 1 to 18 or SCRs 19 to 20 of a full-length human factor H.

21. The composition of claim 20, wherein the biologically active fragment of human factor H comprises amino acids 21-266 of SEQ ID NO: 3.

22. The composition of claim 20, wherein the biologically active fragment of human factor H comprises amino acids 21-320 of SEQ ID NO: 3.

23. The composition of claim 20, wherein the biologically active fragment of human factor H comprises amino acids 21-509 of SEQ ID NO: 3.

24. The composition of claim 20, wherein the biologically active fragment of human factor H comprises amino acids 19-1106 of SEQ ID NO: 3.

25. The composition of claim 20, wherein the biologically active fragment of human factor H comprises the amino acid sequence of SEQ ID NO: 5.

26. The composition of claim 20, wherein the biologically active fragment of human factor H comprises the amino acid sequence of SEQ ID NO: 6.

27. The composition of claim 20, wherein the biologically active fragment of human factor H comprises the amino acid sequence of SEQ ID NO: 7.

28. The composition of claim 20, wherein the biologically active fragment of human factor H comprises the amino acid sequence of SEQ ID NO: 8.

29. A composition comprising a fusion protein and a pharmaceutically acceptable carrier, wherein said fusion protein comprises an anti-annexin A2 antibody or an antigen-binding fragment thereof fused to a biologically active fragment of human MCP, wherein the biologically active fragment of human MCP comprises:

one or more of: a fragment comprising amino acids 35-96 of SEQ ID NO: 19, a fragment comprising amino acids 97-159 of SEQ ID NO: 19, a fragment comprising amino acids 160-225 of SEQ ID NO: 19, a fragment comprising amino acids 226-285 of SEQ ID NO: 19, and a fragment comprising amino acids 302-326 of SEQ ID NO: 19.

30. The composition of claim 19, wherein the biologically active fragment of human MCP comprises amino acids 35-343 of SEQ ID NO: 19.

31. The composition claim 19, wherein the biologically active fragment of human MCP comprises amino acids 35-285 of SEQ ID NO: 19.

32. A composition comprising a fusion protein and a pharmaceutically acceptable carrier, wherein said fusion protein comprises an anti-annexin A2 antibody or an antigen-binding fragment thereof fused to a biologically active fragment of human CD59, wherein the biologically active fragment of human CD59 comprises amino acids 26-101 of SEQ ID NO: 19.

33. The composition of claim 19, wherein the biologically active fragment of human CD59 comprises amino acids 26-102 of SEQ ID NO: 21.

34. A composition comprising a fusion protein and a pharmaceutically acceptable carrier, said fusion protein comprising an anti-annexin A2 antibody or an antigen-binding fragment thereof fused to a biologically active fragment of human CR1, wherein the biologically active fragment of human CR1 comprises one or more of a fragment comprising amino acids 42-101 of SEQ ID NO: 23, a fragment comprising amino acids 102-163 of SEQ ID NO: 23, a fragment comprising amino acids 164-234 of SEQ ID NO: 23, a fragment comprising amino acids 236-295 of SEQ ID NO: 23, a fragment comprising amino acids 295-355 of SEQ ID NO: 23, a fragment comprising amino acids 356-418 of SEQ ID NO: 23, a fragment comprising amino acids 446-489 of SEQ ID NO: 23, a fragment comprising amino acids 491-551 of SEQ ID NO: 23, a fragment comprising amino acids 552-613 of SEQ ID NO: 23, a fragment comprising amino acids 614-684 of SEQ ID NO: 23, a fragment comprising amino acids 686-745 of SEQ ID NO: 23, a fragment comprising amino acids 745-805 of SEQ ID NO: 23, a fragment comprising amino acids 806-868 of SEQ ID NO: 23, a fragment comprising amino acids 869-939 of SEQ ID NO: 23, a fragment comprising amino acids 941-1001 of SEQ ID NO: 23, a fragment comprising amino acids 1002-1063 of SEQ ID NO: 23, a fragment comprising amino acids 1064-1134 of SEQ ID NO: 23, a fragment comprising amino acids 1136-1195 of SEQ ID NO: 23, a fragment comprising amino acids 1195-1255 of SEQ ID NO: 23, a fragment comprising amino acids 1256-1318 of SEQ ID NO: 23, a fragment comprising amino acids 1319-1389 of SEQ ID NO: 23, a fragment comprising amino acids 1394-1454 of SEQ ID NO: 23, a fragment comprising amino acids 1455-1516 of SEQ ID NO: 23, a fragment comprising amino acids 1517-1587 of SEQ ID NO: 23, a fragment comprising amino acids 1589-1648 of SEQ ID NO: 23, a fragment comprising amino acids 1648-1708 of SEQ ID NO: 23, a fragment comprising amino acids 1709-1771 of SEQ ID NO: 23, a fragment comprising amino acids 1772-1842 of SEQ ID NO: 23, a fragment comprising amino acids 1877-1906 of SEQ ID NO: 23, and a fragment comprising amino acids 1907-1967 of SEQ ID NO: 23.

35. The composition of claim 34, wherein the biologically active fragment of human CR1 comprises amino acids 42-295 of SEQ ID NO: 23.

36. The composition of claim 34, wherein the biologically active fragment of human CR1 comprises amino acids 491-684 of SEQ ID NO: 23.

37. The composition of claim 34, wherein the biologically active fragment of human CR1 comprises amino acids 491-1134 of SEQ ID NO: 23.

38. The composition of claim 34, wherein the biologically active fragment of human CR1 comprises amino acids 491-1842 of SEQ ID NO: 23.

39. A composition comprising a fusion protein and a pharmaceutically acceptable carrier, said fusion protein comprising an anti-annexin A2 antibody or an antigen-binding fragment thereof fused to a biologically active fragment of mouse Crry, wherein the biologically active fragment of mouse Crry comprises the extracellular domain or SCRs 1 to 5 of a full-length mouse Crry.

40. The composition of claim 39, wherein the biologically active fragment of mouse Crry comprises amino acids 41-405 of SEQ ID NO: 25.

41. The composition of claim 39, wherein the biologically active fragment of mouse Crry comprises amino acids 83-400 of SEQ ID NO: 25.

* * * * *